United States Patent
Noshi et al.

(10) Patent No.: US 11,911,394 B2
(45) Date of Patent: Feb. 27, 2024

(54) COMPOUND AND METHOD FOR THE PREVENTION OF TRANSMISSION OF INFLUENZA VIRUS

(71) Applicants: **Hoffmann-La

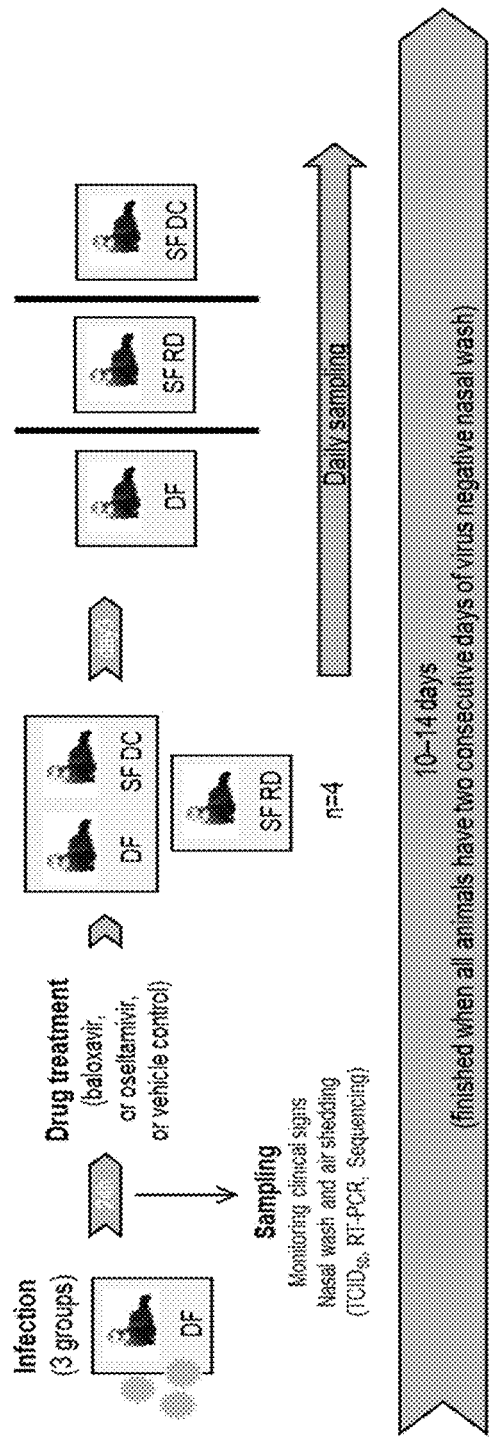
FIG. 1 Time course and study design of Example 1

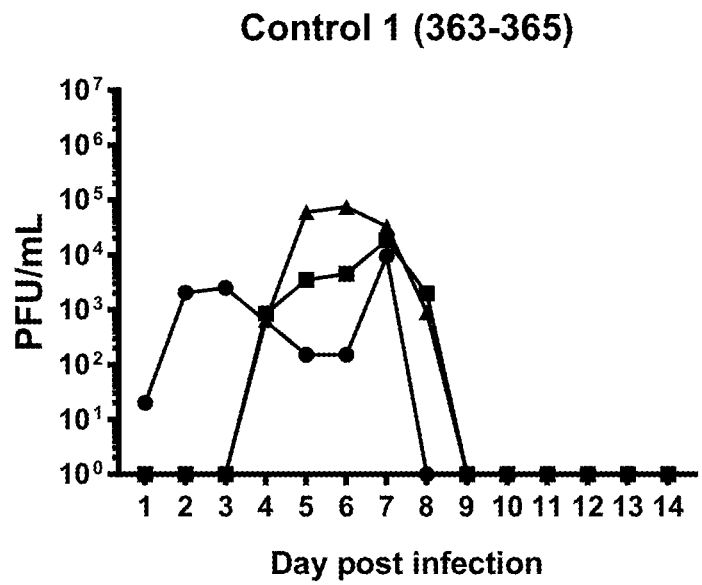
FIG. 2A Plaque assay results of Example 1, Control 1
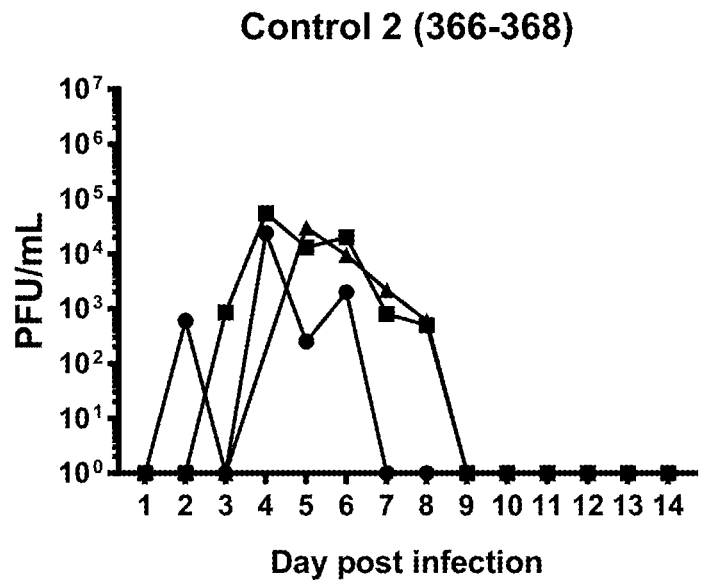
FIG. 2B Plaque assay results of Example 1, Control 2

FIG. 2C Plaque assay results of Example 1, Control 3

FIG. 2D Plaque assay results of Example 1, Control 4

—●— Donor  —■— Sentinel Direct Contact (DC)  —▲— Sentinel Respiratory Droplet (RD)

Summary: control ferrets positive for influenza as detected by the Plaque assay:

Donor: 4/4

Sentinel DC: 4/4

Sentinel RD: 3/4 (here all (4/4) were positive in the RT-PCR assay)

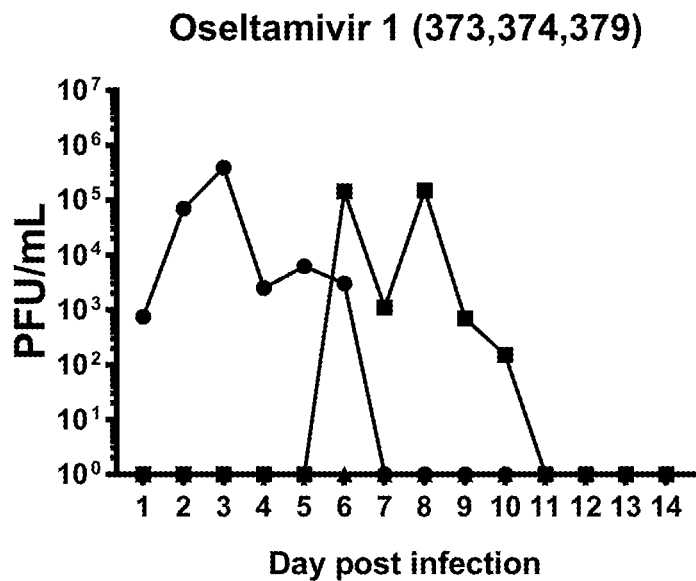
FIG. 2E Plaque assay results of Example 1, Oseltamivir 1
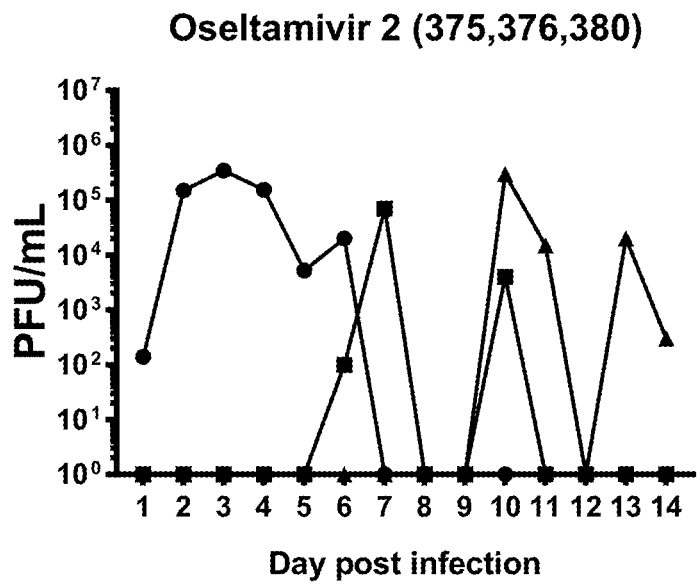
FIG. 2F Plaque assay results of Example 1, Oseltamivir 2

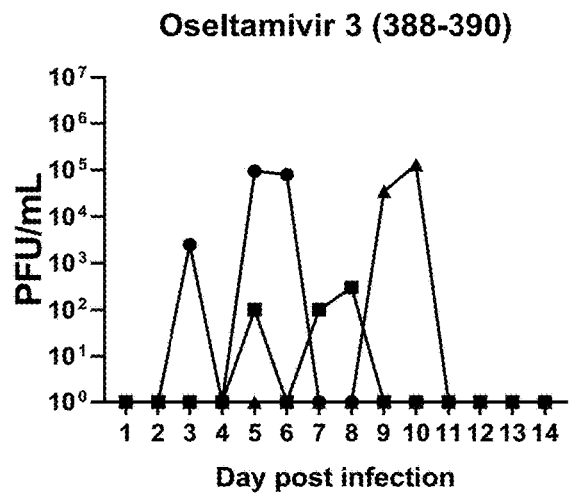
FIG. 2G Plaque assay results of Example 1, Oseltamivir 3
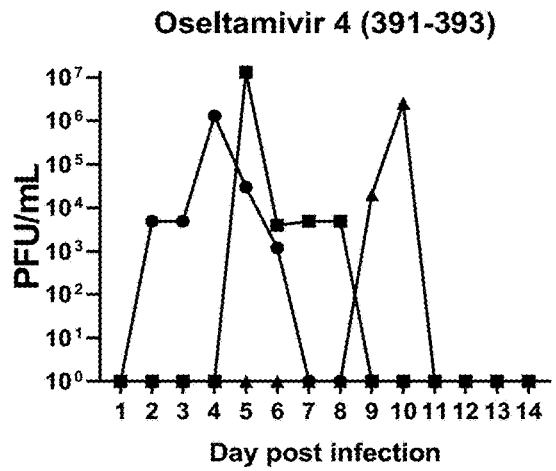
FIG. 2H Plaque assay results of Example 1, Oseltamivir 4
→ Donor  → Sentinel Direct Contact (DC)  → Sentinel Respiratory Droplet (RD)
Summary: Ferrets treated with oseltamivir positive for influenza as detected by the Plaque assay:
Donor: 4/4
Sentinel DC: 4/4
Sentinel RD: 3/4 (here all (4/4) were positive in the RT-PCR assay)

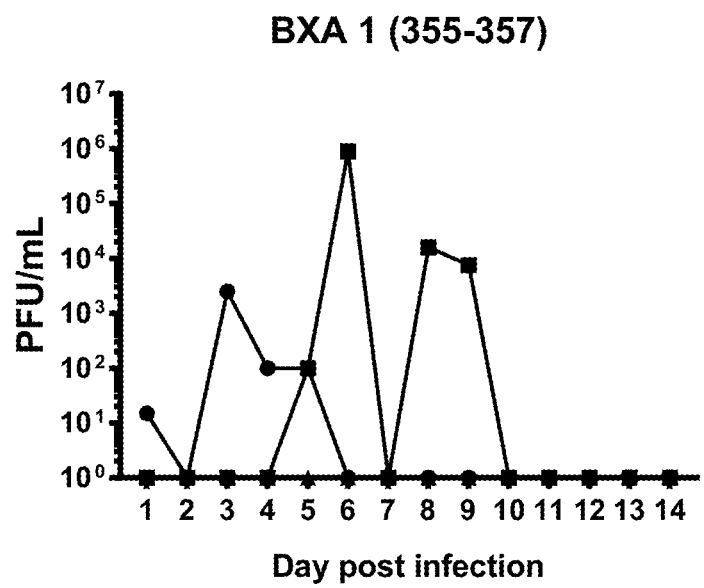
FIG. 2I Plaque assay results of Example 1, Baloxavir 1
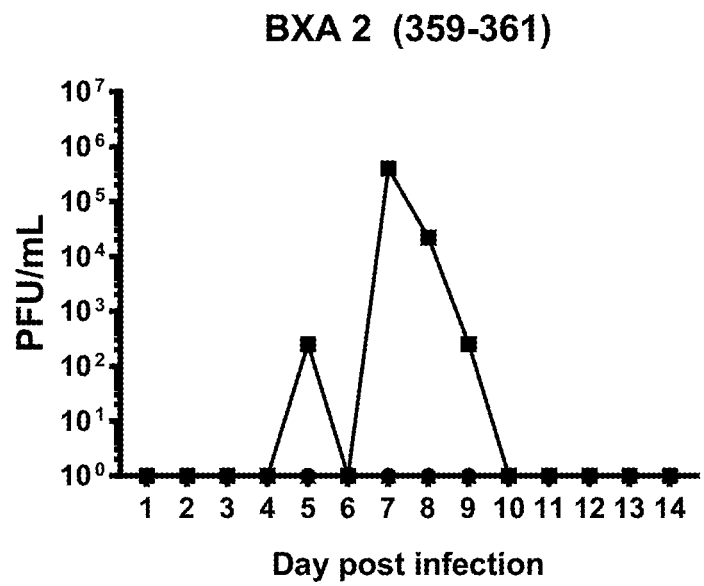
FIG. 2J Plaque assay results of Example 1, Baloxavir 2

FIG. 2K Plaque assay results of Example 1, Baloxavir 3

FIG. 2L Plaque assay results of Example 1, Baloxavir 4

— Donor　— Sentinel Direct Contact (DC)　— Sentinel Respiratory Droplet (RD)

Summary: Ferrets treated with baloxavir positive for influenza as detected by the Plaque assay:

Donor: 3/4 (here all (4/4) were positive in the RT-PCR assay)

Sentinel DC: 4/4

Sentinel RD: 1/4

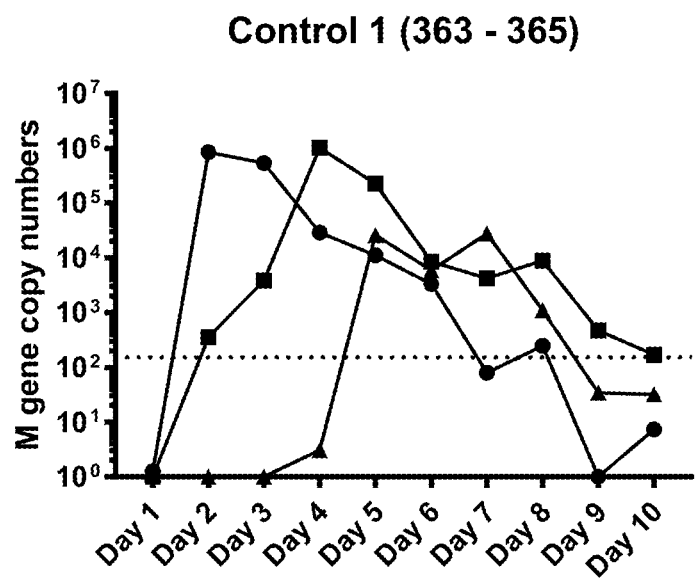
FIG. 3A qRT-PCR results of Example 1, Control 1
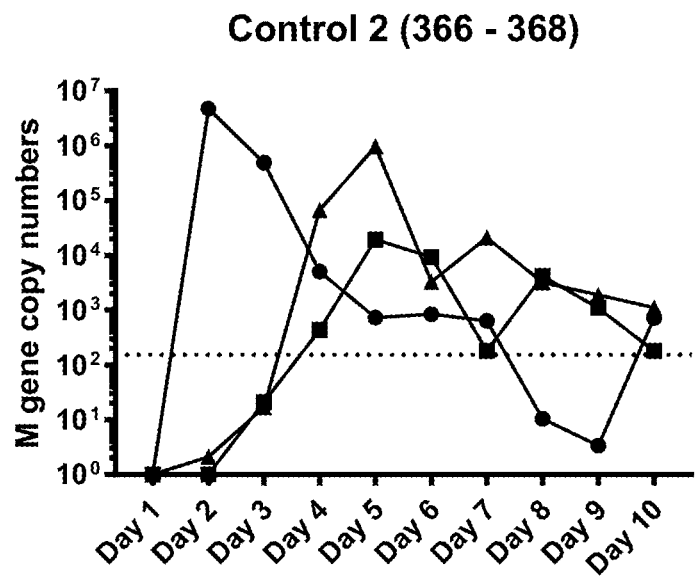
FIG. 3B qRT-PCR results of Example 1, Control 2

FIG. 3C qRT-PCR results of Example 1, Control 3

FIG. 3D qRT-PCR results of Example 1, Control 4

— ♦ — Donor    — ■ — Sentinel Direct Contact (DC)    — ▲ — Sentinel Respiratory Droplet (RD)

Summary: Control ferrets positive for influenza as detected by the qRT-PCR:

Donor: 4/4

Sentinel DC: 4/4

Sentinel RD: 4/4

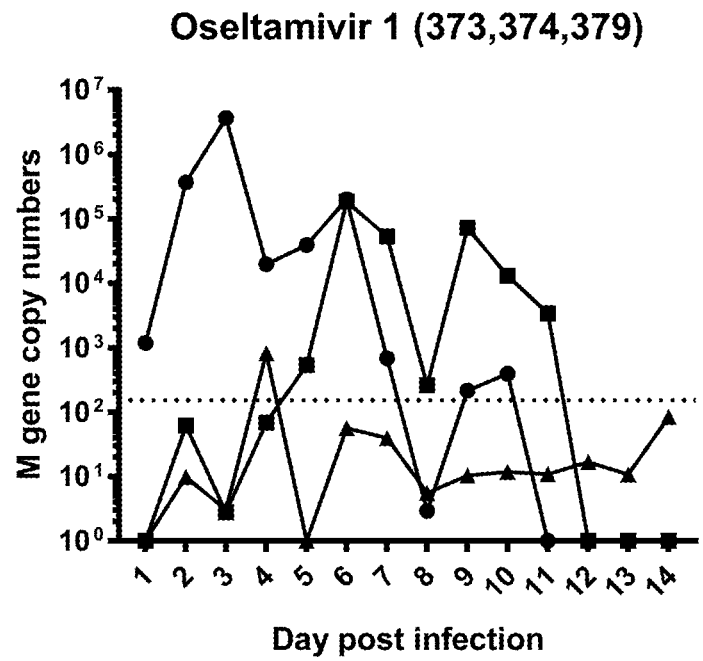
FIG. 3E qRT-PCR results of Example 1, Oseltamivir 1
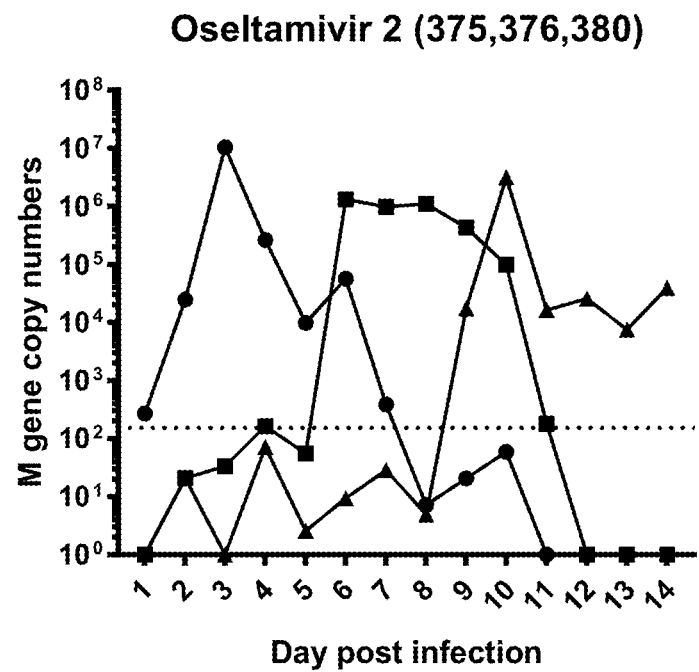
FIG. 3F qRT-PCR results of Example 1, Oseltamivir 2

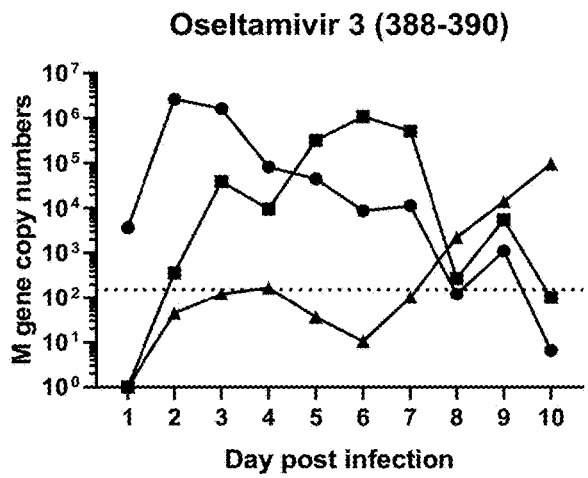
FIG. 3G qRT-PCR results of Example 1, Oseltamivir 3
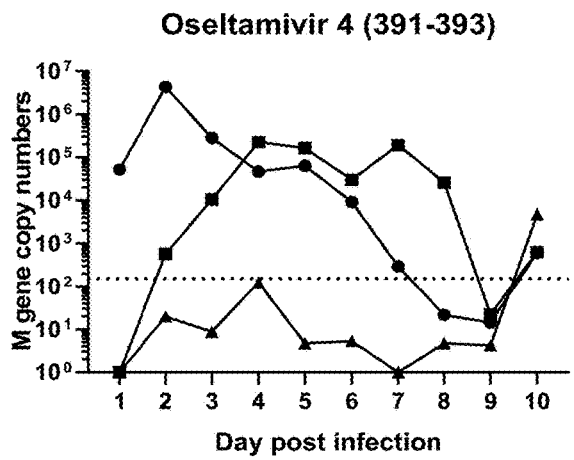
FIG. 3H qRT-PCR results of Example 1, Oseltamivir 4
→ Donor  → Sentinel Direct Contact (DC)  → Sentinel Respiratory Droplet (RD)
Summary: Ferrets treated with oseltamivir positive for influenza as detected by the qRT-PCR:
Donor: 4/4
Sentinel DC: 4/4
Sentinel RD: 4/4

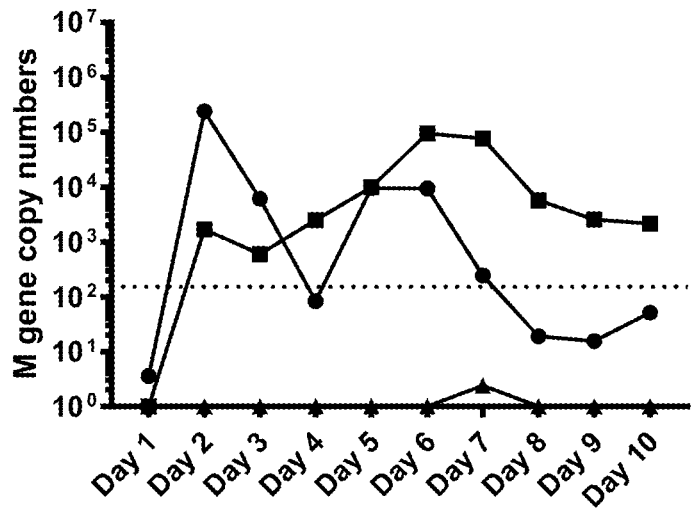
FIG. 3I qRT-PCR results of Example 1, Baloxavir 1
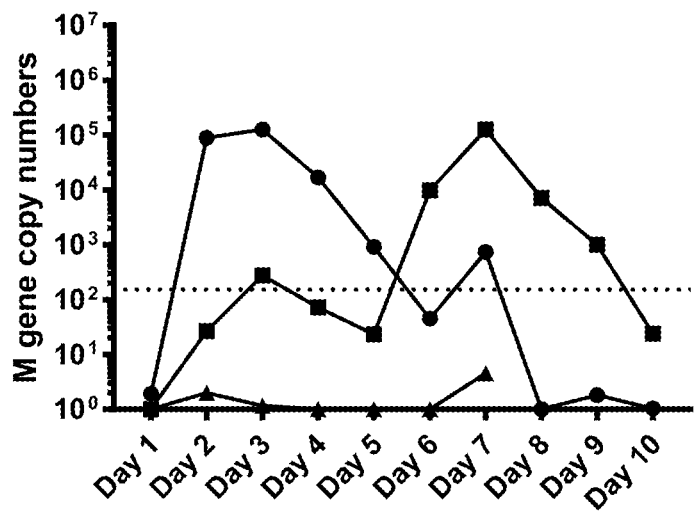
FIG. 3J qRT-PCR results of Example 1, Baloxavir 2

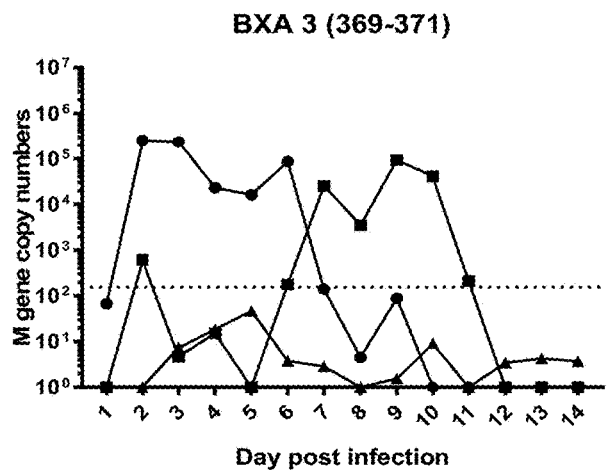
FIG. 3K qRT-PCR results of Example 1, Baloxavir 3
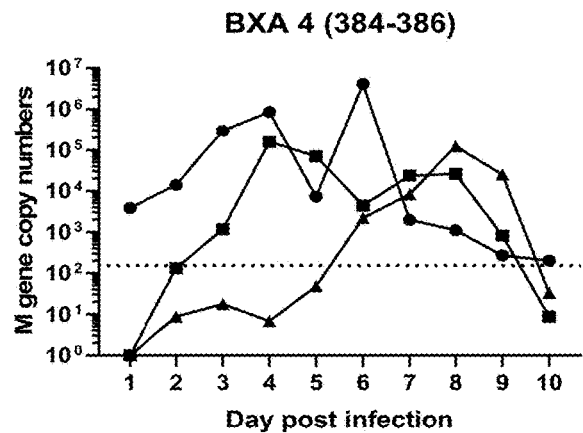
FIG. 3L qRT-PCR results of Example 1, Baloxavir 4
→ Donor   ■ Sentinel Direct Contact (DC)   ▲ Sentinel Respiratory Droplet (RD)
Summary: Ferrets treated with baloxavir positive for influenza as detected by the qRT-PCR:
Donor: 4/4
Sentinel Control: 100% transmission Oseltamivir: 100% transmission Baloxavir: 100% transmission in Direct Contact; 25% transmission by Respiratory Droplet

|  | Donor | Direct contact | Respiratory droplet |
|---|---|---|---|
| Control | 4/4 | 4/4 | 4/4 |
| Oseltamivir | 4/4 | 4/4 | 4/4 |
| Baloxavir | 4/4 | 4/4 | 1/4 |

FIG. 3M Summary of qRT-PCR results

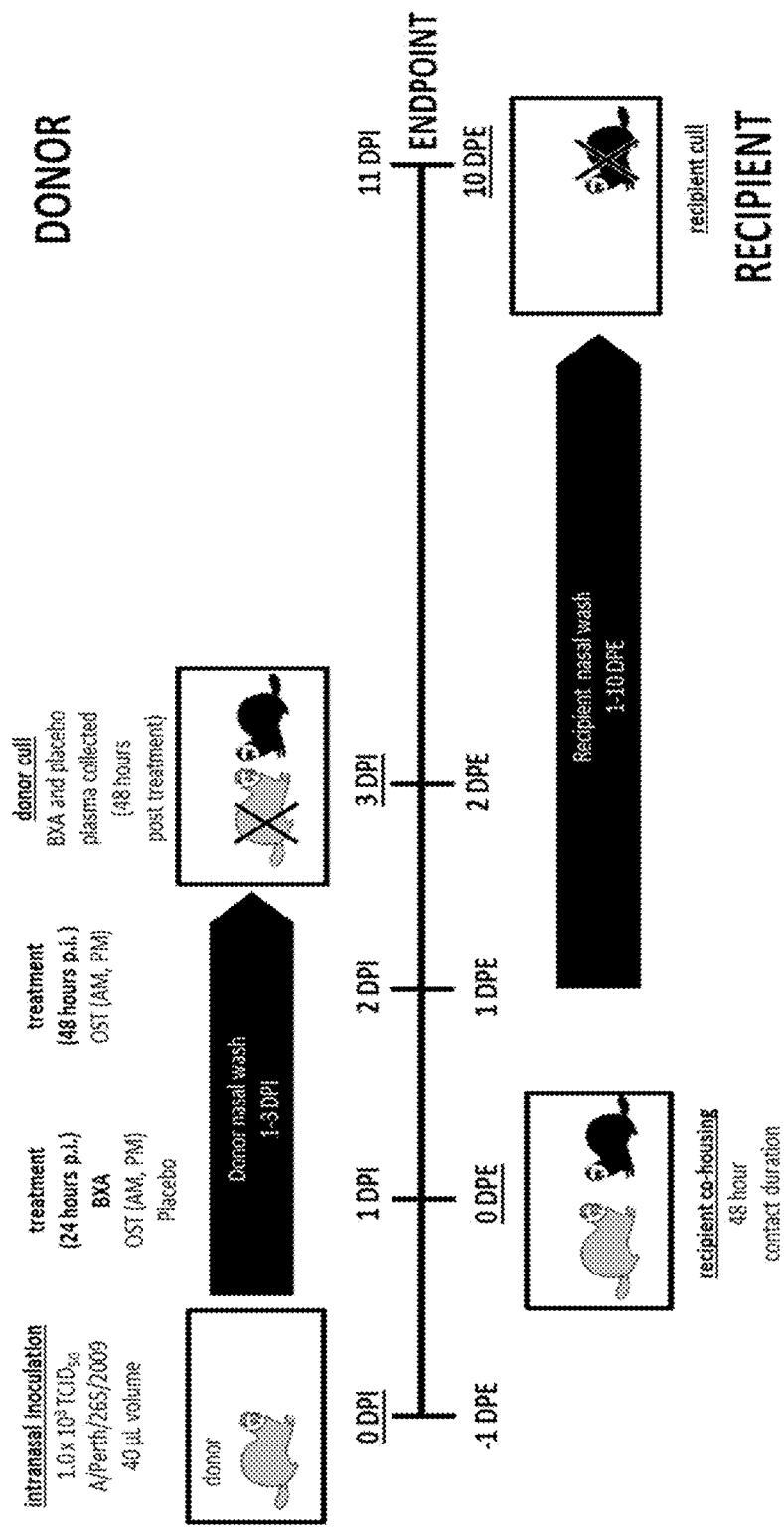
FIG. 4 Time course and of Experiment 1 of Example 2

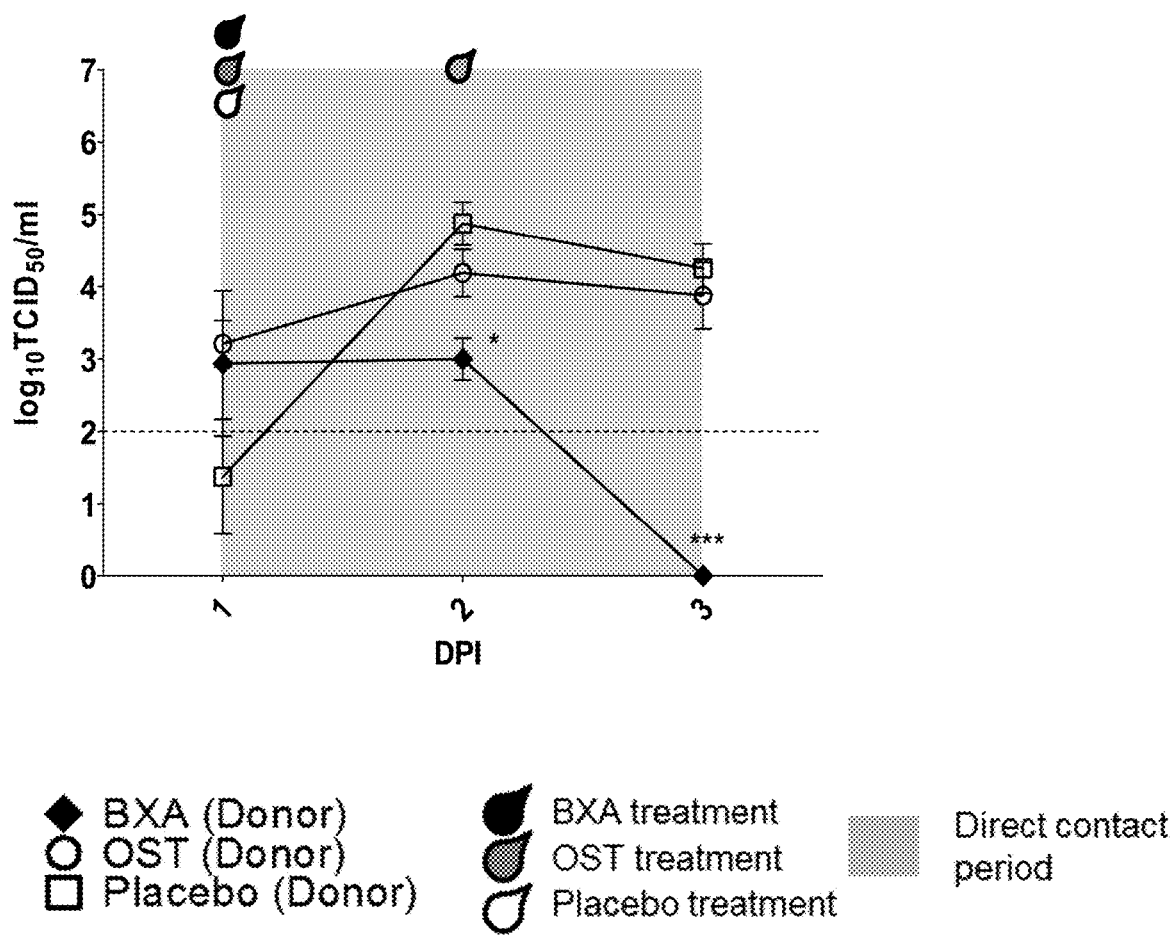
FIG. 5 TCID50 results of the donor ferrets of Experiment 1 of Example 2

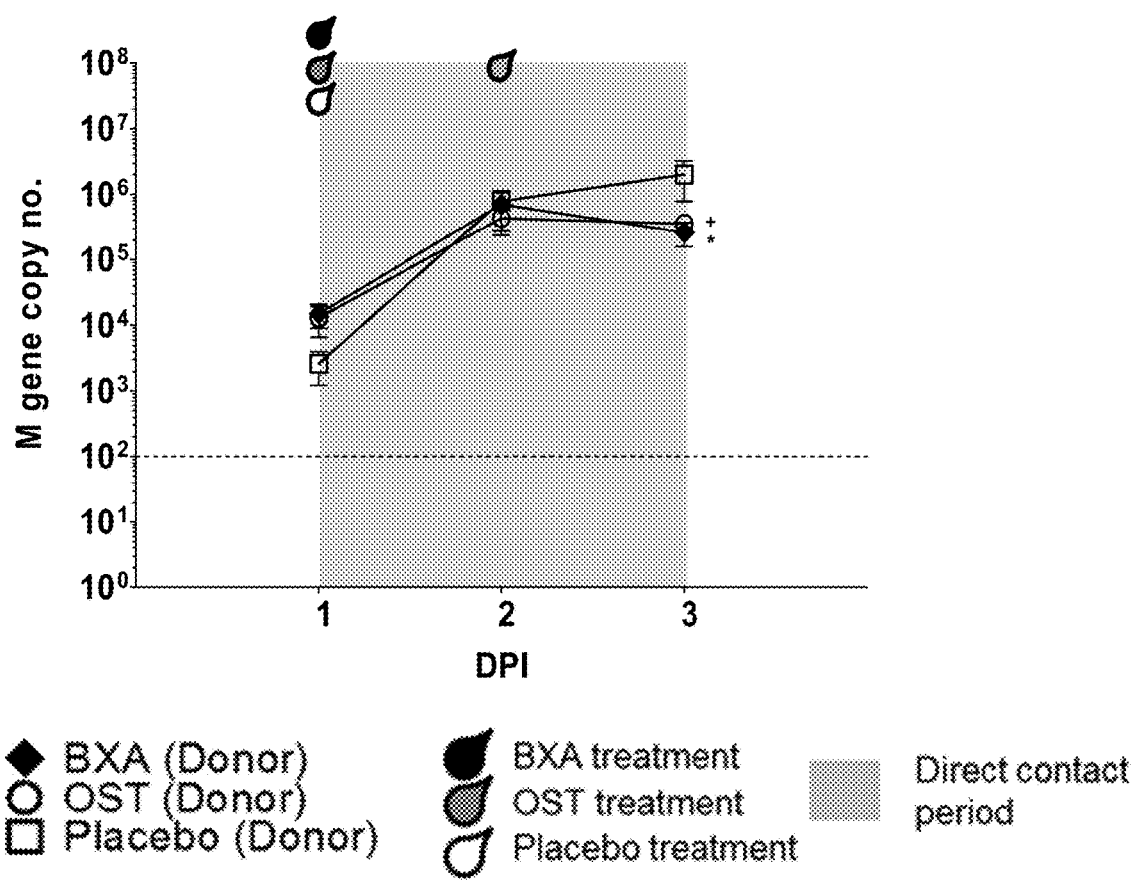
FIG. 6 qRT-PCR results of the donor ferrets of Experiment 1 of Example 2

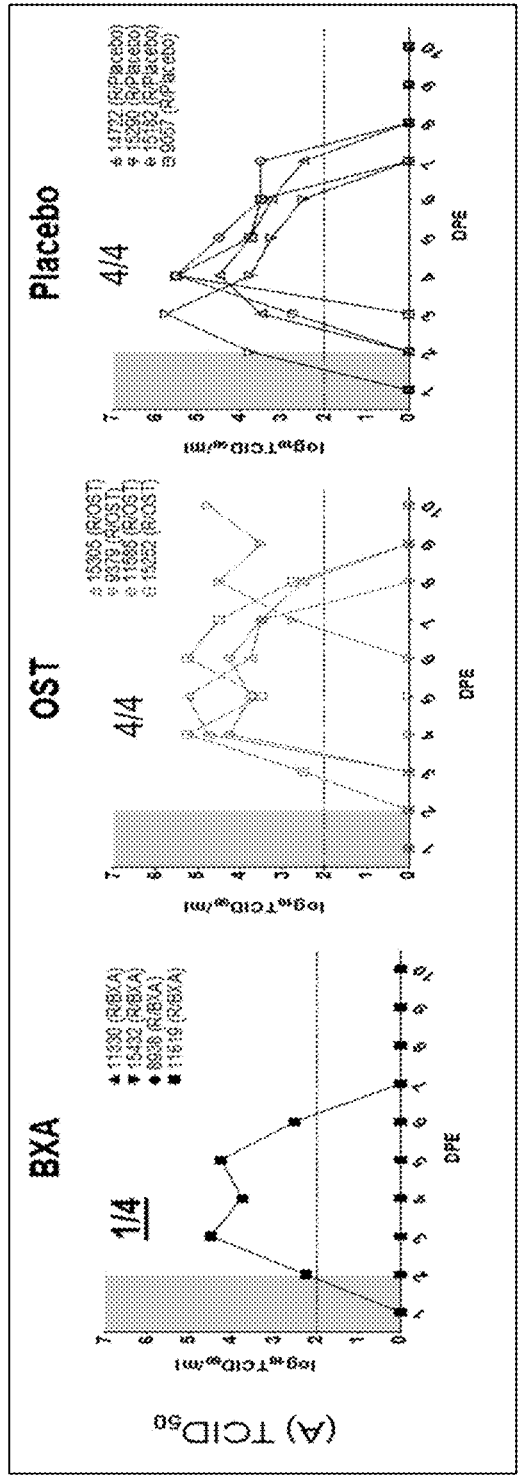
FIG. 7A $TCID_{50}$ results of the recipient ferrets of Experiment 1 of Example 2
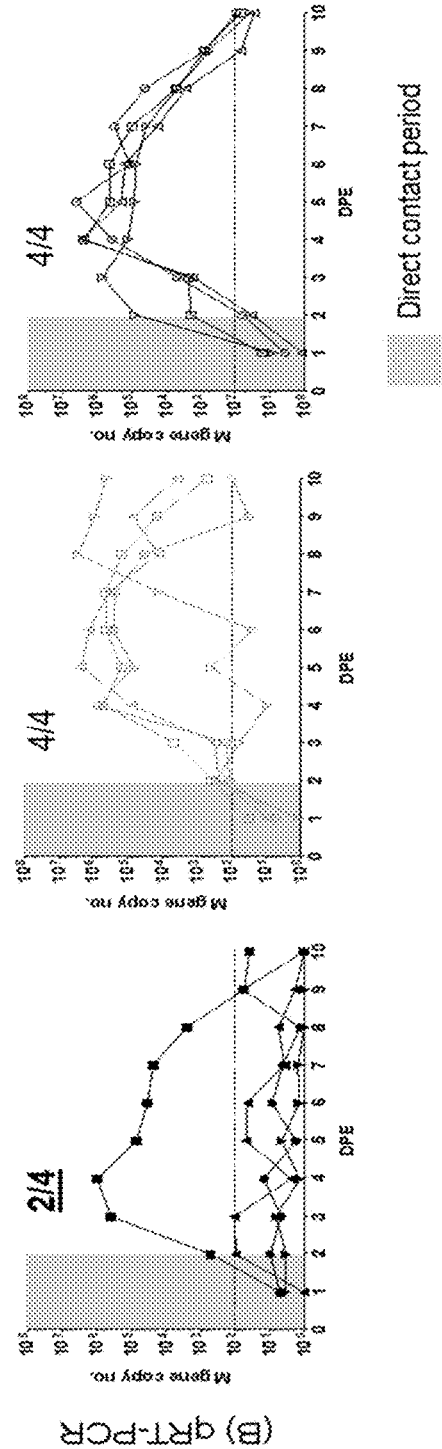
FIG. 7B qRT-PCR results of the recipient ferrets of Experiment 1 of Example 2

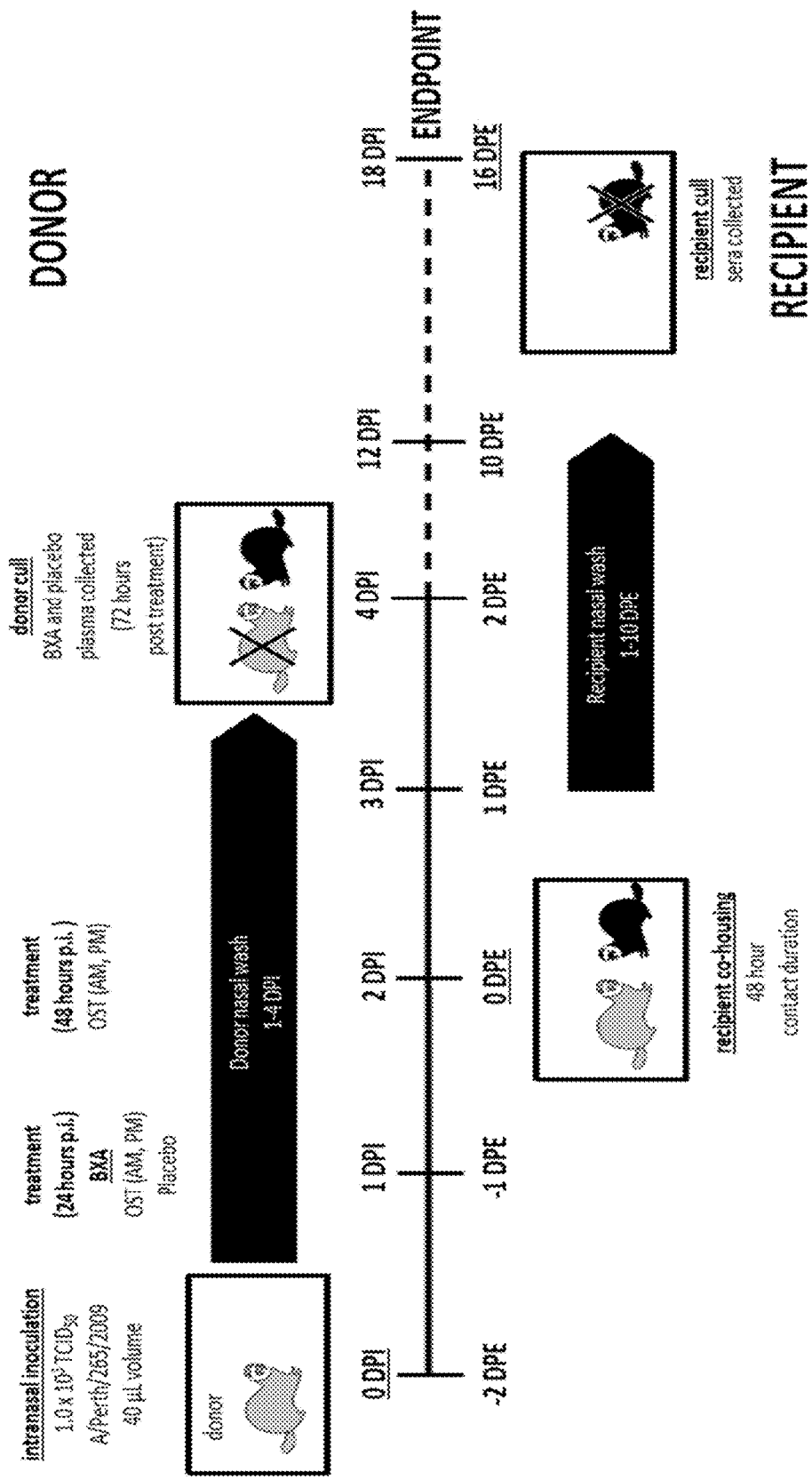
FIG. 8 Time course of Experiment 2 of Example 2

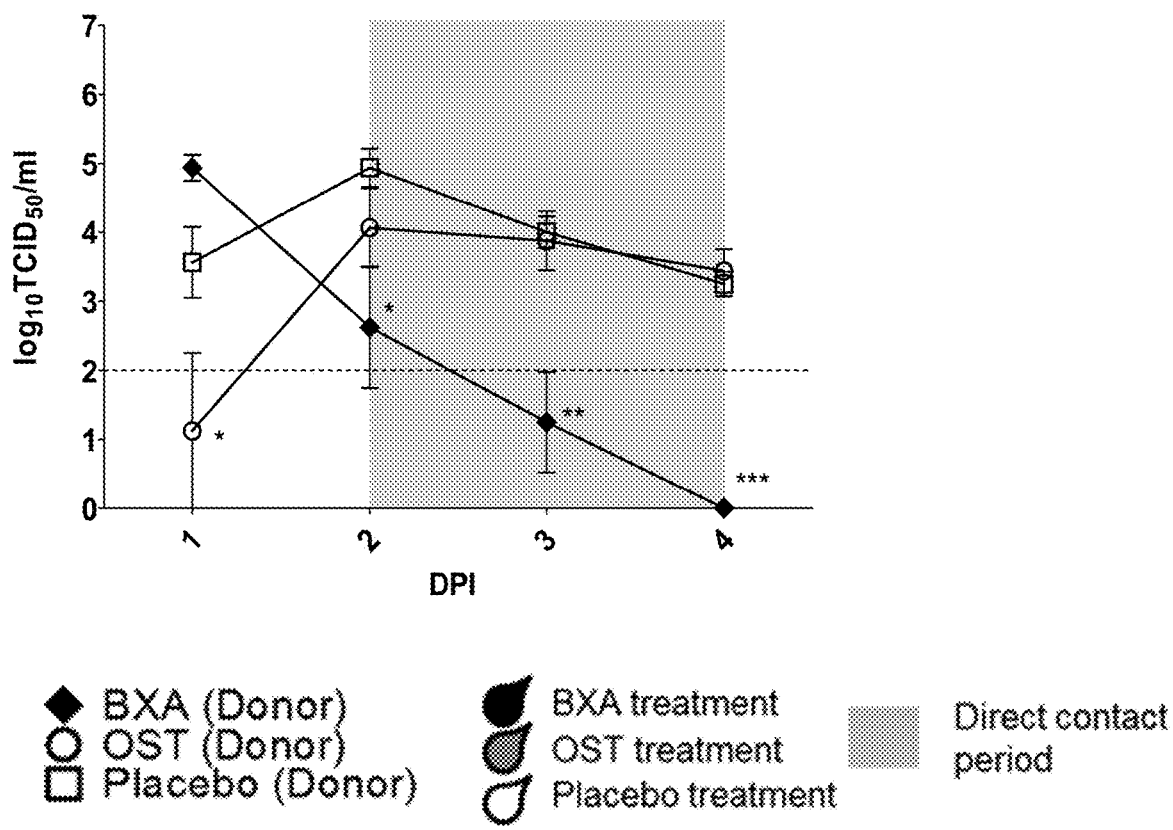
FIG. 9A TCID$_{50}$ results of the donor ferrets of Experiment 2 of Example 2

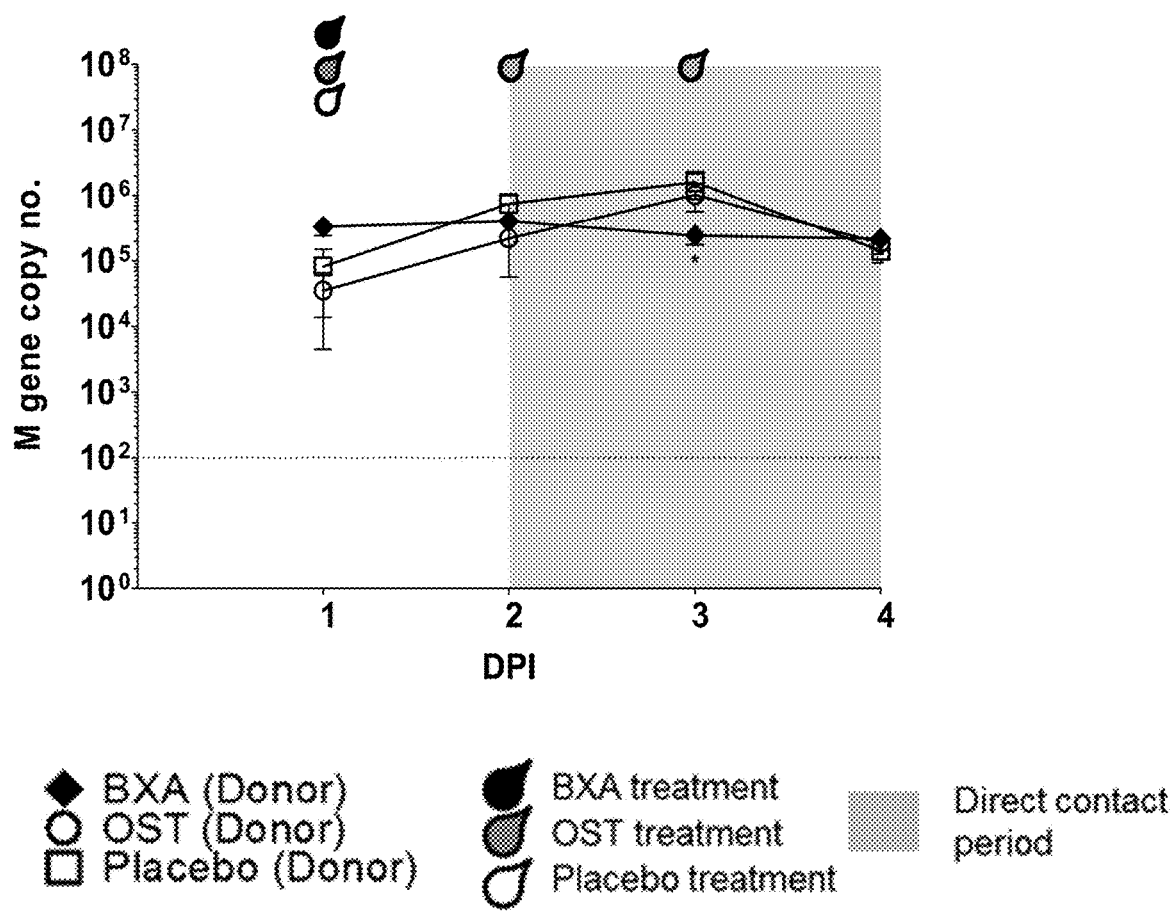
FIG. 9B qRT-PCR results of the donor ferrets of Experiment 2 of Example 2

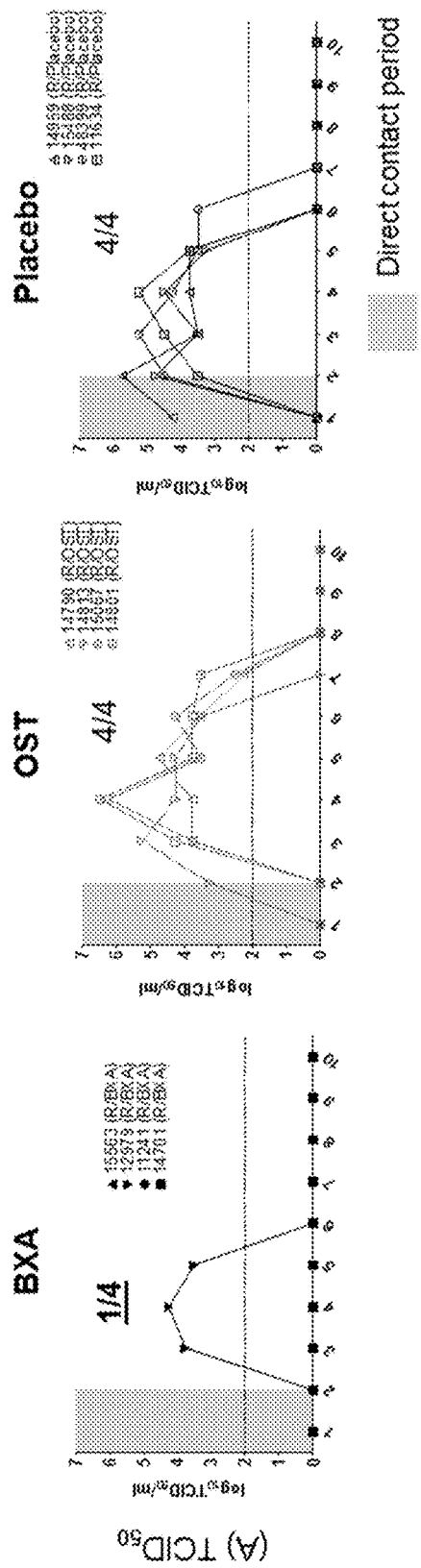
FIG. 10A $TCID_{50}$ results of the recipient ferrets of Experiment 2 of Example 2
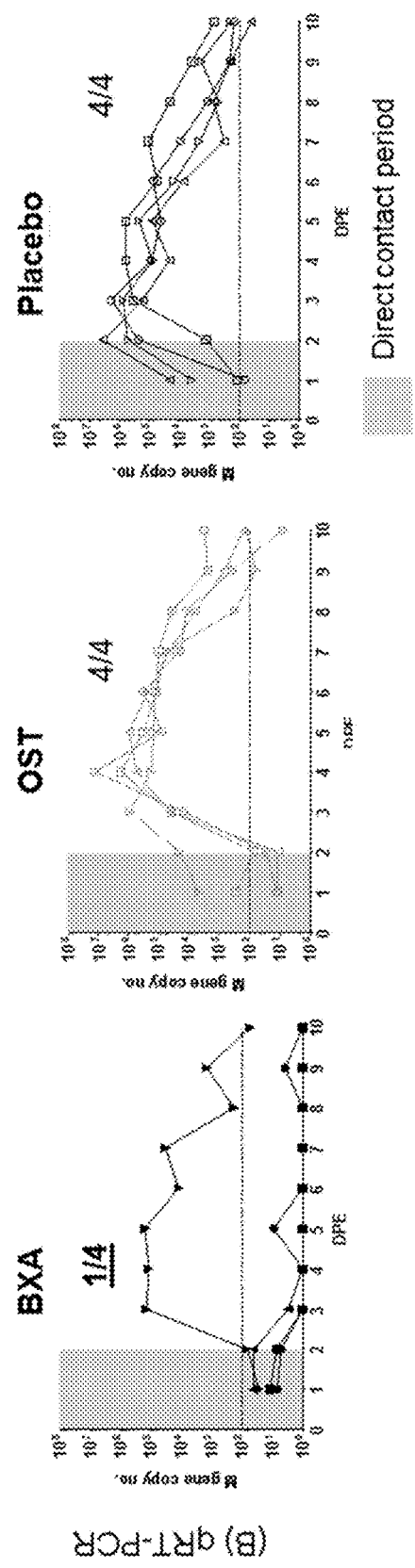
FIG. 10B qRT-PCR results of the recipient ferrets of Experiment 2 of Example 2

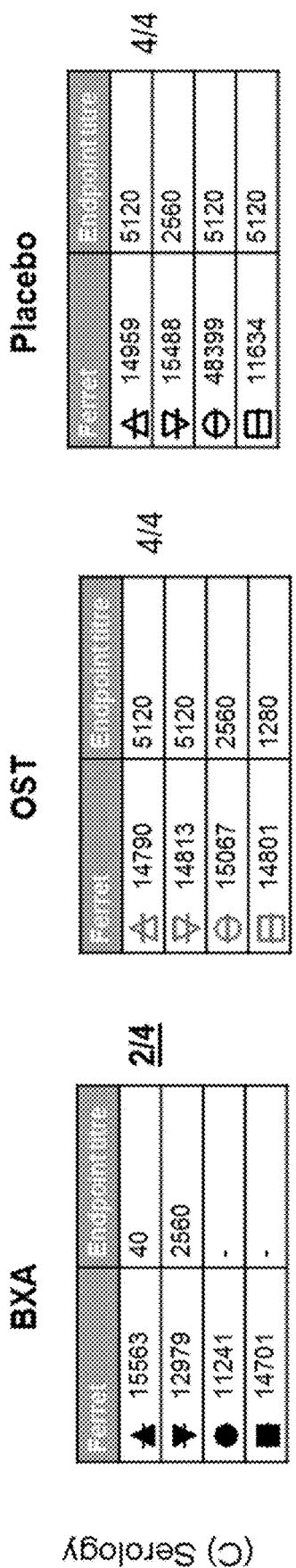
FIG. 10C Serology results of the recipient ferrets of Experiment 2 of Example 2

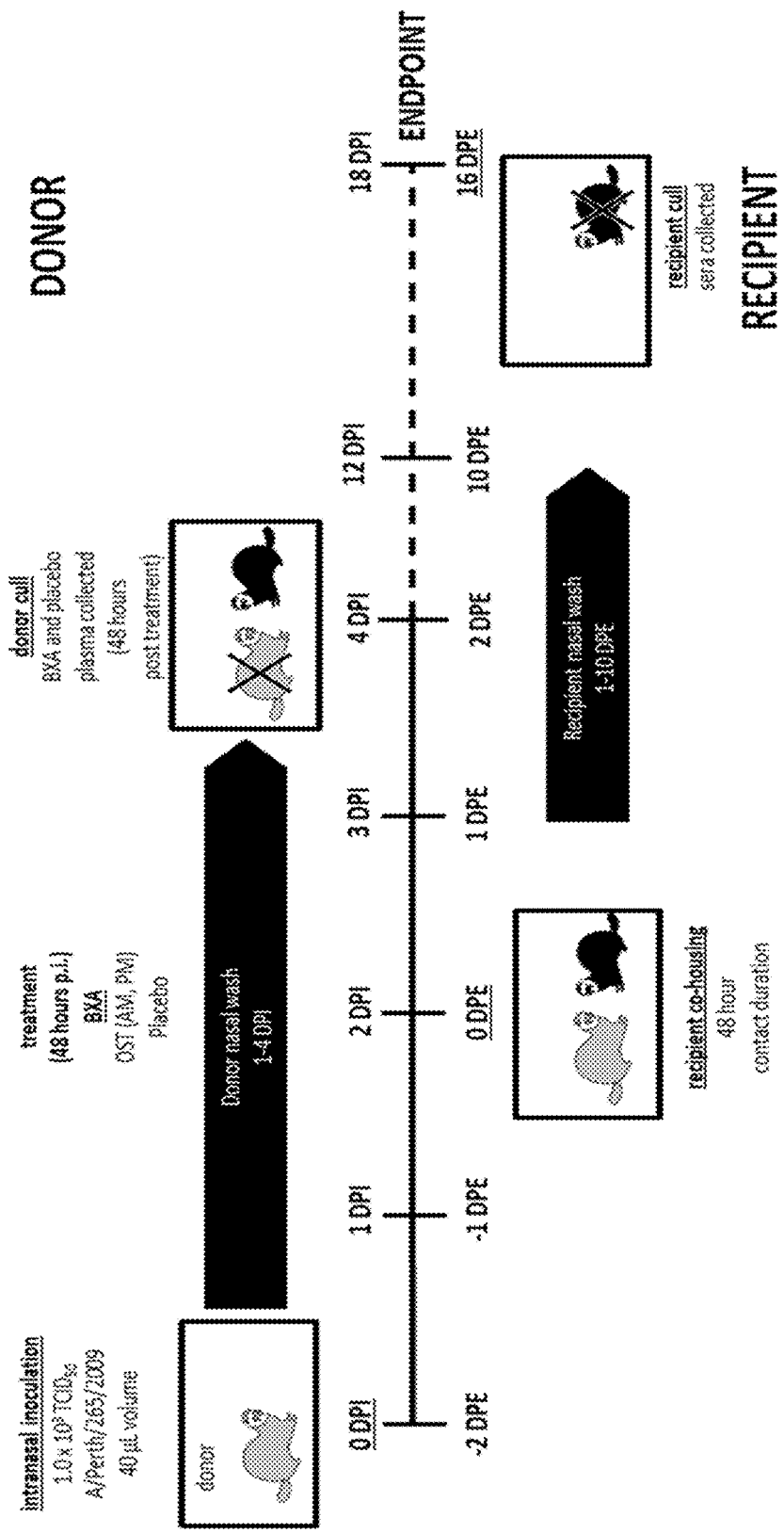
FIG. 11 Time course of Experiment 3 of Example 2

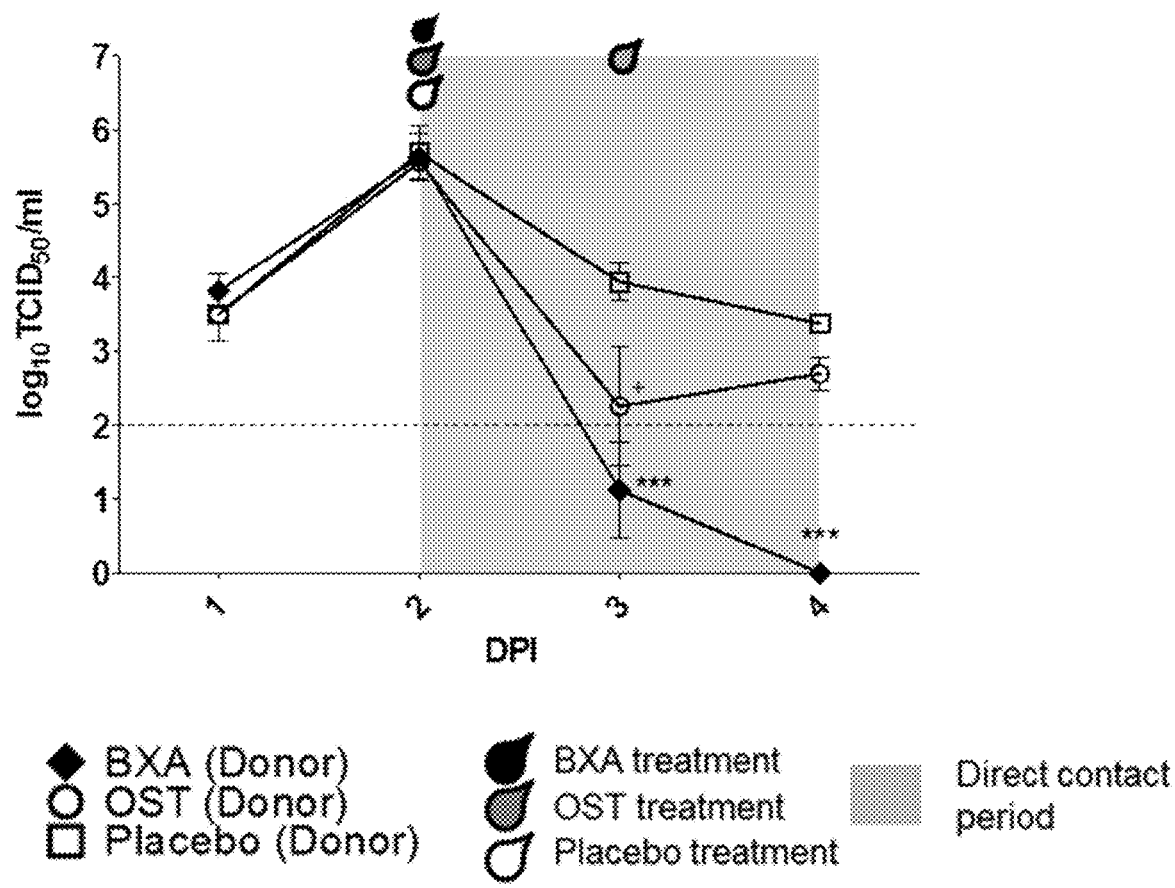
FIG. 12A TCID$_{50}$ results of the donor ferrets of Experiment 3 of Example 2

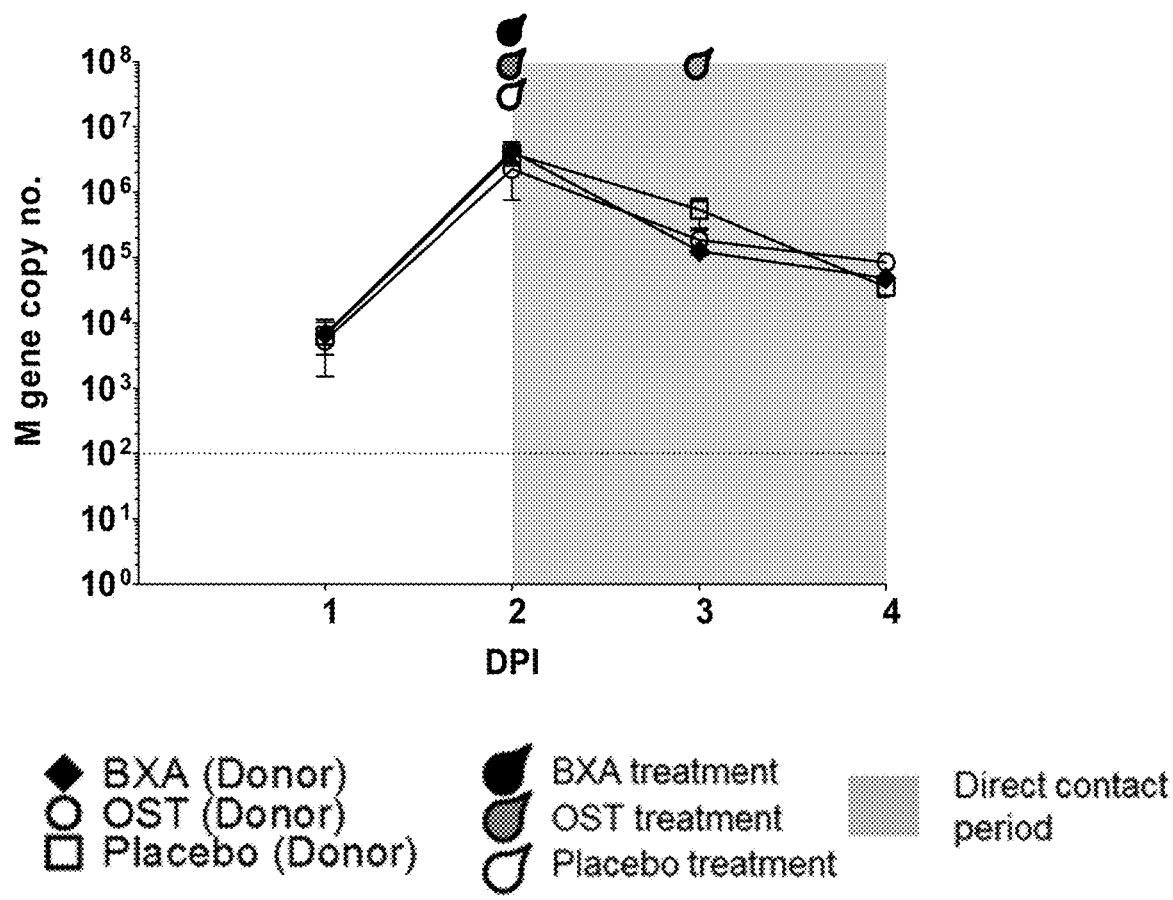
FIG. 12B qRT-PCR results of the donor ferrets of Experiment 3 of Example 2

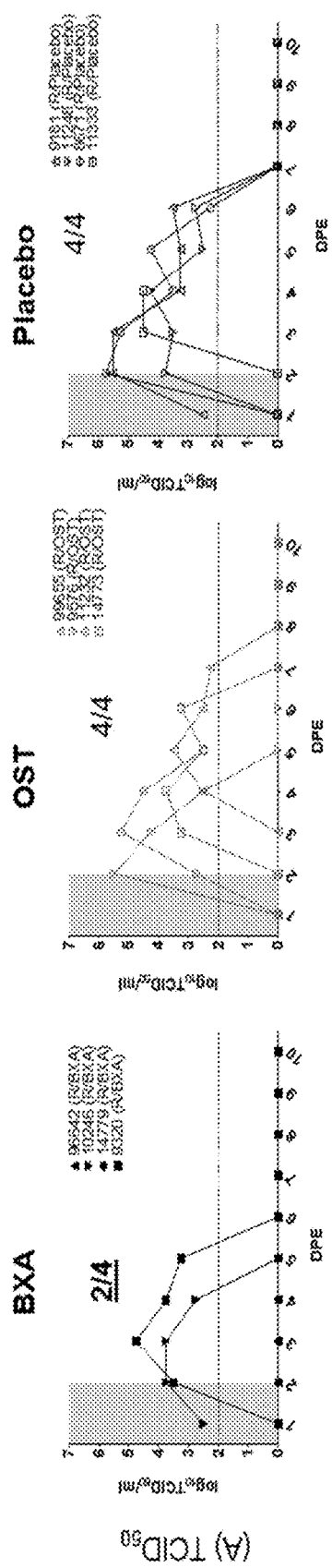
FIG. 13A TCID$_{50}$ results of the recipient ferrets of Experiment 3 of Example 2
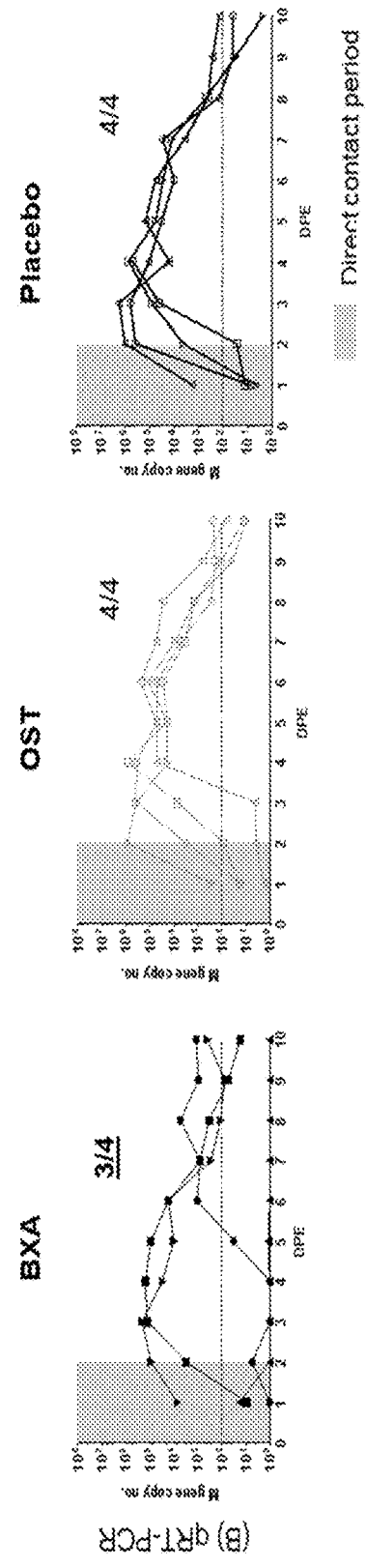
FIG. 13B qRT-PCR results of the recipient ferrets of Experiment 3 of Example 2

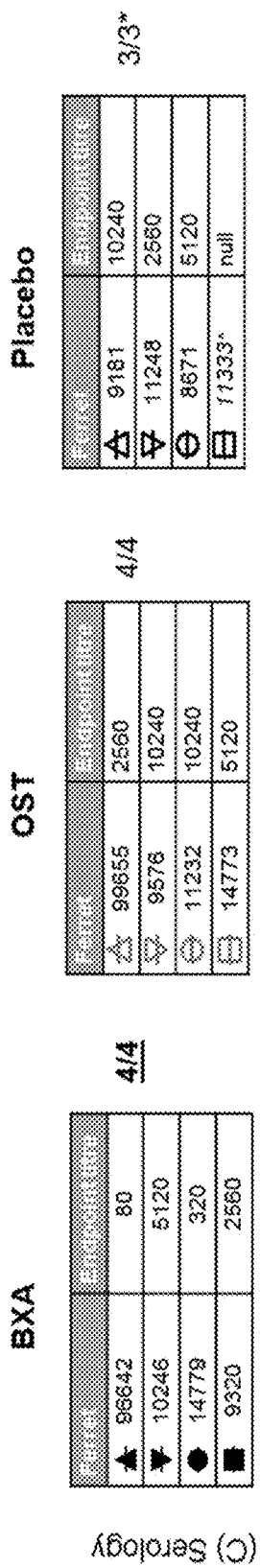
FIG. 13C Serology results of the recipient ferrets of Experiment 3 of Example 2

| Experiment conditions | Antiviral groups | %donors that were shedding infectious virus (TCID$_{50}$) at endpoint |
|---|---|---|
| LL-FER-18-07 | BXA | 0% (0/4) |
| 24h DPI treatment | OST | 100% (4/4) |
| Immediate co-housing | Placebo | 100% (4/4) |
| LL-FER-18-08 | BXA | 0% (0/4) |
| 24h DPI treatment | OST | 100% (4/4) |
| 24 h delayed co-housing | Placebo | 100% (4/4) |
| LL-FER-18-08 | BXA | 0% (0/4) |
| 48h DPI treatment | OST | 100% (4/4) |
| Immediate co-housing | Placebo | 100% (4/4) |

FIG. 14 Summary of the effect of baloxavir on donor ferrets in Experiments 1-3 of Example 2

| Antiviral group | Experiment | %recipients shedding infectious virus (TCID$_{50}$) following exposure | %recipients qRT-PCR positive following exposure | %recipients serology positive |
|---|---|---|---|---|
| LL-FER-18-07<br><br>24h DPI treatment<br><br>Immediate co-housing | BXA | 25% (1/4) | 50% (2/4) | No bleeds taken |
| | OST | 100% (4/4) | 100% (4/4) | No bleeds taken |
| | Placebo | 100% (4/4) | 100% (4/4) | No bleeds taken |
| LL-FER-18-08<br><br>24h DPI treatment<br><br>24 h delayed co-housing | BXA | 25% (1/4) | 25% (1/4) | 50% (2/4) |
| | OST | 100% (4/4) | 100% (4/4) | 100% (4/4) |
| | Placebo | 100% (4/4) | 100% (4/4) | 100% (4/4) |
| LL-FER-18-08<br><br>48h DPI treatment<br><br>Immediate co-housing | BXA | 50% (2/4) | 75% (3/4) | 100% (4/4) |
| | OST | 100% (4/4) | 100% (4/4) | 100% (4/4) |
| | Placebo | 100% (4/4) | 100% (4/4) | 100% (4/4) |

FIG. 15 Summary of the effect of baloxavir on contact transmission in Experiments 1-3 of Example 2

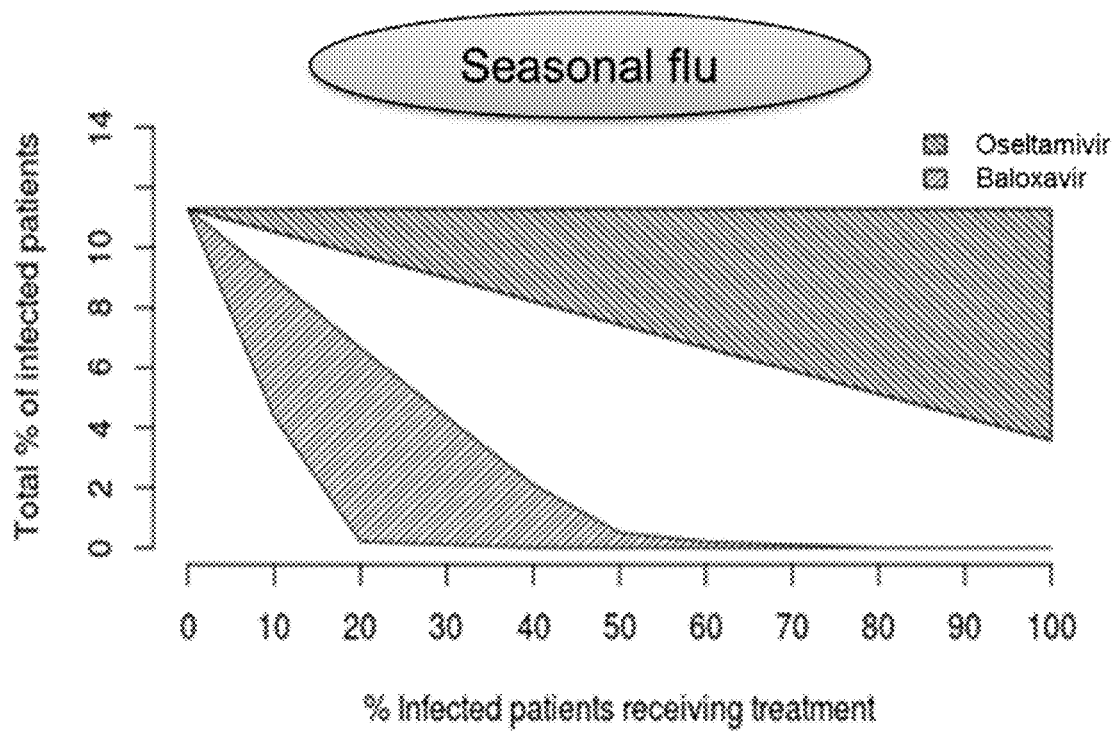
Assumptions seasonal flu:
- 1 day incubation + 1 day infectious not treated
- 5 days infectious period without treatment
- Flu Transmission: 1.35 subjects infected by 1 patient over 5 days infectious period ($\beta=0.27$)
- 20% effective vaccination, 30 % susceptible population
- Tshed 24h-48h for Baloxavir, 72h-96h for Oseltamivir
FIG. 16 Flu transmission modeling for Baloxavir (Seasonal flu)

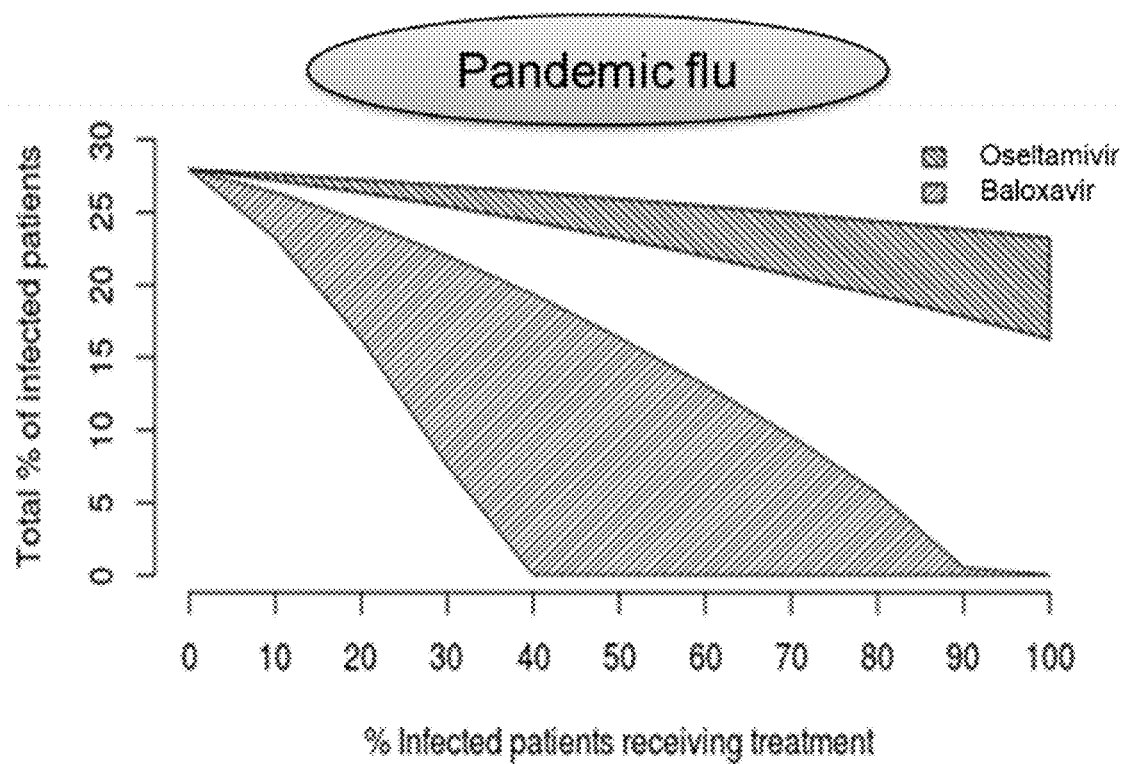
Assumptions pandemic flu:
- 1 day incubation
- 6 days infectious period without treatment
- Flu Transmission: 2.9 subjects infected by 1 patient over 6 days infectious period ($\beta=0.48$)
- No effective vaccination, 30 % susceptible population
- Tshed 24h-48h for Baloxavir, 72h-96h for Oseltamivir
FIG. 17 Flu transmission modeling for Baloxavir (Pandemic flu)

Canadian Acute Respiratory Illness and Flu Scale (CARIFS) Questionnaire

| Item | No Problem | Minor Problem | Moderate Problem | Major Problem | Don't Know/Not Applicable |
|---|---|---|---|---|---|
| 1. Poor appetite | ☐ | ☐ | ☐ | ☐ | ☐ |
| 2. Not sleeping well | ☐ | ☐ | ☐ | ☐ | ☐ |
| 3. Irritable, cranky, fussy | ☐ | ☐ | ☐ | ☐ | ☐ |
| 4. Feels unwell | ☐ | ☐ | ☐ | ☐ | ☐ |
| 5. Low energy, tired | ☐ | ☐ | ☐ | ☐ | ☐ |
| 6. Not playing well | ☐ | ☐ | ☐ | ☐ | ☐ |
| 7. Crying more than usual | ☐ | ☐ | ☐ | ☐ | ☐ |
| 8. Needing extra care | ☐ | ☐ | ☐ | ☐ | ☐ |
| 9. Clinginess | ☐ | ☐ | ☐ | ☐ | ☐ |
| 10. Headache | ☐ | ☐ | ☐ | ☐ | ☐ |
| 11. Sore throat | ☐ | ☐ | ☐ | ☐ | ☐ |
| 12. Muscle aches or pains | ☐ | ☐ | ☐ | ☐ | ☐ |
| 13. Fever | ☐ | ☐ | ☐ | ☐ | ☐ |
| 14. Cough | ☐ | ☐ | ☐ | ☐ | ☐ |
| 15. Nasal congestion, runny nose | ☐ | ☐ | ☐ | ☐ | ☐ |
| 16. Vomiting | ☐ | ☐ | ☐ | ☐ | ☐ |
| 17. Not interested in what's going on | ☐ | ☐ | ☐ | ☐ | ☐ |
| 18. Unable to get out of bed | ☐ | ☐ | ☐ | ☐ | ☐ |

Since the last assessment has the subject been able to return to day care/school, or resume their normal daily activity in the same way as performed prior to developing the flu? ☐ Yes ☐ No

This form was filled out by:
☐ Parent
☐ Carer
☐ Other

Note: The term "Carer" in this questionnaire corresponds to the term "caregiver" used throughout the protocol.

FIG. 18

COMPOUND AND METHOD FOR THE PREVENTION OF TRANSMISSION OF INFLUENZA VIRUS

CROSS-REFERENCE TO RELATED APPLICATIONS

This application is a continuation of U.S. application Ser. No. 16/830,764, filed Mar. 26, 2020, which claims the benefit of priority to EP Application No. 19 16 6228.7, filed Mar. 29, 2019, the contents of which are incorporated herein by reference in their entirety.

REFERENCE TO SEQUENCE LISTING

This application incorporates by reference a Computer Readable Form (CRF) of a Sequence Listing in ASCII text format submitted with this application, entitled "050045-555001US_sequence_listing" was created on Mar. 25, 2020, and is 7,064 bytes in size.

BACKGROUND

The present invention relates to a method for preventing transmission of influenza virus, wherein said method comprises administering an effective amount of a compound to a patient having an influenza virus infection, hereinafter referred to as "index patient", wherein the compound has one of the formulae (I) and (II), or its pharmaceutically acceptable salt. The compound to be used in the present invention reduces infectivity of the influenza virus of the index patient, and therefore, reduces the risk of the index patient to trigger an influenza epidemic or an influenza pandemic as compared to a control patient. Therefore, one aspect of the present invention relates to a method for preventing an influenza epidemic or an influenza pandemic, wherein the method comprises administering an effective amount of a compound to patients having an influenza virus infection (index patients), wherein the compound is administered to at least 10% of all influenza infected persons of a city's or country's population, and wherein the compound has one of the formulae (I) and (II), or its pharmaceutically acceptable salt.

An influenza virus infection is an acute respiratory infectious disease caused by influenza viruses and is spread mainly by airborne transmission, particularly droplet infection. Influenza A and B viruses are highly contagious (Vanderlinden, *Med Res Rev* 2014; 34(2):301-339). Therefore, influenza epidemics often arise from seasonal influenza viruses and are a major burden to global health. There are an estimated 3-5 million cases of severe disease worldwide and approximately 290-650 thousand people die from influenza annually (WHO News Release, Geneva, Switzerland, 14 Dec. 2017; WHO Fact Sheet, Geneva, Switzerland, 31 Jan. 2018; Baxter D, *Hum Vaccin Immunother.* 2016; 12(10): 2712-2717). Influenza also places significant demands on healthcare services each season, and impacts society through lost workforce productivity (WHO Fact Sheet, Geneva, Switzerland, 31 Jan. 2018).

Influenza pandemics are sudden and up to now inevitable events. They have caused several global health emergencies during the last century. The first and most severe of these is estimated to have resulted in more than 40-50 million deaths worldwide (Francis, *Am J Hyg.*, 1945, 42:1-11). Experts anticipate that the next pandemic will be associated with a high death toll and a high degree of illness requiring hospitalization, thus producing a considerable strain on health care resources. Pandemics are global by their nature, and few countries are likely to be spared. In developing countries, where health care resources are already strained and the general population is frequently weakened by poor health and nutritional status, the impact is likely to be tremendous.

Conditions surrounding the 1997 Hong Kong outbreak of "avian influenza" highlight the need for advance planning to ensure an adequate response to a health emergency that is certain to be unpredictable, complex, rapidly evolving and accompanied by considerable public alarm. Once a pandemic begins it was in the past too late to accomplish the many key activities required to minimize the impact. Therefore, planning and implementation of preparatory activities must start well in advance. Planning for pandemics will also enhance the capacity to respond to other large-scale health emergencies, including bioterrorist threats, that require mass access to prophylactic and therapeutic interventions and strong national plans which include a risk communication component to help calm public fears. The impact of pandemic influenza is likely to be far greater, by orders of magnitude, than usual bioterrorism scenarios. Unlike most other health emergencies, pandemics occur in several waves and last one to two years. Response efforts will, therefore, need to be sustained for a prolonged period. In addition, preparation for an influenza pandemic will enhance the response to influenza epidemics, which occur each year and are thought to kill every year from 500 000 to 1 million people worldwide. Investment in pandemic preparedness thus has direct and immediate utility as a measure for reducing the impact of a certain and recurring event.

Annual vaccination programs are the cornerstone of attempts to prevent influenza infections, but the effectiveness of these programs is variable due to both suboptimal uptake of vaccinations and mismatches between the vaccine and circulating influenza strains (Centers for Disease Control and Prevention "*Vaccine effectiveness—how well does the flu vaccine work?*" 3 Oct. 2017). M2 inhibitors, such as amantadine, and neuraminidase inhibitors, such as oseltamivir, are the typical drugs which are used against influenza. However, a modelling study of M2 inhibitor use in an institutional outbreak setting did not find that treatment alone significantly affected the course of the outbreak, indicating that the treatment with this anti-influenza drug does not reduce the likelihood of transmission (Stilianakis, *Journal of Infectious Diseases,* 1998, 177:863-873). There is currently no agent proven to reduce influenza transmission. Consequently, it is an important unmet medical need to identify antiviral agents which reduce transmission of the influenza virus, and therewith prevent or attenuate the outbreak of influenza epidemics during seasonal flu or of influenza pandemics.

Thus, the technical problem underlying the present invention is the provision of means and methods to safeguard health in society.

The technical problem is solved by provision of the embodiments characterized in the claims.

SUMMARY

Accordingly, the present invention relates to a method for preventing transmission of influenza, wherein said method comprises administering an effective amount of a compound to a patient having an influenza virus infection (index patient), wherein the compound has one of the following formulae I and II:

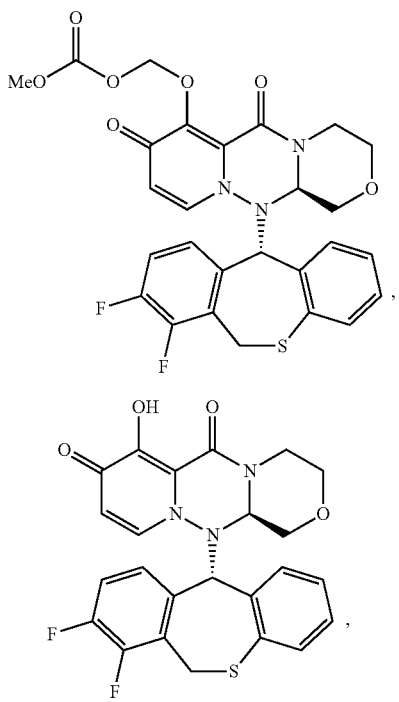

or its pharmaceutically acceptable salt.

Thus, the present invention relates to a compound for use in treating an influenza virus infection of a patient (index patient), wherein the compound has one of the formulae (I) and (II), or its pharmaceutically acceptable salt, and wherein the compound prevents (e.g. reduces) transmission of the influenza virus. Also encompassed by the present invention is a pharmaceutical composition comprising a compound which has one of the formulae (I) and (II), or its pharmaceutically acceptable salt, and optionally comprising a pharmaceutically acceptable carrier, wherein the pharmaceutical composition prevents (e.g. reduces) transmission of the influenza virus. This pharmaceutical composition is particularly useful for the treatment of an influenza-infected patient (index patient) and prevents (e.g. reduces) transmission of the influenza virus of said patient.

BRIEF DESCRIPTION OF THE DRAWINGS

The present invention is further described by reference to the following non-limiting Figures and Examples.

The Figures show:

FIG. 1. Time course and study design of Example 1. Time course of the experiment of Example 1. Baloxavir was administered once as s.c. suspension with 1 mg/kg at 4 different locations in the back of the ferret. Oseltamivir phosphate (5 mg/kg) was orally administered twice daily for 5 days. See text for details. DF, donor ferret; SF, sentinel ferret; DC, direct contact; RD, respiratory droplet.

FIGS. 2A-2L. Plaque assay results of Example 1. FIGS. 2A-2D show the control ferrets. All control ferrets were positive for influenza as detected by the plaque assay (Donor: 4/4; Sentinel DC: 4/4; Sentinel RD: 3/4, here all (4/4) were positive in the RT-PCR assay). FIGS. 2E-2H show the ferrets treated with oseltamivir. All ferrets treated with oseltamivir were positive for influenza as detected by the plaque assay (Donor: 4/4; Sentinel DC: 4/4; Sentinel RD: 3/4, here all (4/4) were positive in the RT-PCR assay). FIGS. 2I-2L show the ferrets treated with baloxavir. Only one sentinel baloxavir ferret was infected by respiratory droplet infection as detected by the plaque assay (Donor: 3/4, here all (4/4) were positive in the RT-PCR assay; Sentinel DC: 4/4; Sentinel RD: 1/4). DF, donor ferret; SF, sentinel ferret; DC, direct contact; RD, respiratory droplet.

FIGS. 3A-3M. qRT-PCR results of Example 1. FIGS. 3A-3D show the control ferrets. All control ferrets were positive for influenza as detected by the qRT-PCR (Donor: 4/4; Sentinel DC: 4/4; Sentinel RD: 4/4). FIGS. 3E-3H show the ferrets treated with oseltamivir. All ferrets treated with oseltamivir were positive for influenza as detected by the qRT-PCR (Donor: 4/4, Sentinel DC: 4/4, Sentinel RD: 4/4). FIGS. 3I-3L show the ferrets treated with baloxavir. Only one sentinel baloxavir ferret was infected by respiratory droplet infection as detected by the qRT-PCR (Donor: 4/4; Sentinel DC: 4/4; Sentinel RD: 1/4). FIG. 3M shows the summary of qRT-PCR results. Only one sentinel baloxavir ferret was infected by respiratory droplet infection as detected by the qRT-PCR. DF, donor ferret; SF, sentinel ferret; DC, direct contact; RD, respiratory droplet.

FIG. 4. Time course of Experiment 1 of Example 2. Baloxavir was administered in a single treatment consisting of 1 mg/kg s.c. injections at 4 separate locations on the back of the ferret (4 mg/kg total). Placebo (1 mL/kg suspension vehicle only) was administered in the same manner. Oseltamivir phosphate (5 mg/kg) was administered orally twice per day until endpoint (excluding final day). Treatment of donor ferrets: 24 hr post donor inoculation. Co-housing of recipient ferrets: 24 hr post donor inoculation. See text for details. BXA, baloxavir; OST, oseltamivir.

FIG. 5. $TCID_{50}$ of donor ferrets in Experiment 1 of Example 2. 0/4 baloxavir-treated donors were shedding detectable infectious virus at 3 days post infection (DPI) endpoint. The group titer of the baloxavir-group was significantly lower than of the placebo-group at 2 DPI (*$p \leq 0.05$) and 3 DPI (***$p \leq 0.001$). 4/4 oseltamivir-treated and 4/4 placebo-treated donors were shedding infectious virus at 3 DPI endpoint. There was no significant difference in group titers observed between oseltamivir-treated and placebo-treated donors. BXA, baloxavir; OST, oseltamivir.

FIG. 6. qRT-PCR results donor ferrets of Experiment 1 of Example 2. Viral RNA present in nasal wash of all animals at all sampling points. Viral copy numbers in the baloxavir-group (*) and oseltamivir-group (+) were significantly reduced compared to placebo at 3 DPI ($p \leq 0.05$). Copy no. threshold of positive detection is based on lowest RNA copy number standard to yield a Ct value <35 per assay. The pharmacokinetics (PK) of the baloxavir-group at 48 hours post treatment was 10.2±2.8 ng/mL baloxavir in plasma ±SD. BXA, baloxavir; OST, oseltamivir.

FIGS. 7A and 7B. Results of the recipient ferrets of Experiment 1 of Example 2. FIG. 7A shows the $TCID_{50}$ results. Only 1/4 baloxavir-group recipient ferrets shed detectable infectious virus following contact exposure to donor, compared to 4/4 oseltamivir-group and 4/4 placebo-group ferrets. FIG. 7B shows the qRT-PCR results. Influenza virus RNA was detected in only 2/4 baloxavir-group recipients, compared to 4/4 oseltamivir-group and 4/4 placebo-group. BXA, baloxavir; OST, oseltamivir.

FIG. 8. Time course of Experiment 2 of Example 2. Baloxavir was administered in a single treatment consisting of 1 mg/kg s.c. injections at 4 separate locations on the back of the ferret (4 mg/kg total). Placebo (1 mL/kg suspension vehicle only) was administered in the same manner. Oseltamivir phosphate (5 mg/kg) was administered orally twice per day until endpoint (excluding final day). Treatment of donor: 24 hr post donor inoculation.

Co-housing of recipient: 48 hr post donor inoculation. See text for details. BXA, baloxavir; OST, oseltamivir.

FIGS. 9A and 9B. Results of the donor ferrets of Experiment 2 of Example 2. FIG. 9A shows the $TCID_{50}$ results. 0/4 baloxavir-treated donors were shedding detectable infectious virus at 4 DPI endpoint. The baloxavir group titer was significantly lower than that of the placebo group at 2 DPI (*$p \leq 0.05$), 3 DPI ($p \leq 0.001$) and 4 DPI (*$p \leq 0.001$). The baloxavir group titer was significantly lower than that of the oseltamivir group on 3-4 DPI ($p \leq 0.01$). However, immediately before treatment (i.e. on 1 DPI) titers were significantly higher in the baloxavir group than in placebo group ($p \leq 0.001$). 4/4 oseltamivir-treated and 4/4 placebo-treated donors were shedding infectious virus at 4 DPI endpoint. The oseltamivir-group titer was significantly lower than that of the placebo-group on 1(DPI) ($p \leq 0.05$), but there was no difference on 2-4 DPI. FIG. 9B shows the qRT-PCR results. Viral RNA was present in nasal wash of all animals at all sampling points. Mean viral copy number was reduced in the baloxavir-group on 3 DPI, but no differences were observed at any other days. The pharmacokinetics (PK) of the baloxavir-group at 72 hr post treatment was 12.5±2.4 ng/mL baloxavir in plasma ±SD. XA, baloxavir; OST, oseltamivir.

FIGS. 10A-10C. Results of the recipient ferrets of Experiment 2 of Example 2. FIG. 10A shows the $TCID_{50}$ results. Only 1/4 baloxavir-group recipient ferrets shed detectable infectious virus following contact exposure to donor, compared to 4/4 oseltamivir-group and 4/4 placebo-group ferrets. FIG. 10B shows the qRT-PCR. Influenza virus RNA was detected in 1/4 baloxavir-group recipients, compared to 4/4 oseltamivir-group and 4/4 placebo-group. FIG. 10C shows the Serology results. 2/4 baloxavir-group recipients demonstrated antibody responses to donor virus, compared to 4/4 oseltamivir-group and 4/4 placebo-group ferrets. Antibody response detected in $TCID_{50}$-negative ferret was reduced (>32 fold change) compared to $TCID_{50}$-positive ferrets. '-' no antibody response observed.

FIG. 11. Time course of Experiment 3 of Example 2. Baloxavir was administered in a single treatment consisting of 1 mg/kg s.c. injections at 4 separate locations on the back of the ferret (4 mg/kg total). Placebo (1 mL/kg suspension vehicle only) was administered in the same manner. Oseltamivir phosphate (5 mg/kg) was administered orally twice per day until endpoint (excluding final day). Treatment of donor: 48 hr post donor inoculation. Co-housing of recipient: 48 hr post donor inoculation. See text for details. BXA, baloxavir; OST, oseltamivir.

FIGS. 12A and 12B. Results of the donor ferrets of Experiment 3 of Example 2. FIG. 12A shows the $TCID_{50}$ results. No (i.e. 0/4) baloxavir-treated donor was shedding infectious virus at 4 DPI endpoint. The group titer of the baloxavir-group was significantly lower than that of the placebo-group at 3 and 4 DPI (**$p \leq 0.001$), and lower than the oseltamivir-group on 4 DPI ($p \leq 0.001$). All (i.e. 4/4) oseltamivir-treated and all (i.e. 4/4) placebo-treated donors were shedding infectious virus at 4 DPI endpoint. The oseltamivir-group titer was significantly lower than the placebo-group titer on 3 DPI ($p \leq 0.05$). FIG. 12B shows the qRT-PCT results. Viral RNA present in nasal wash of all animals at all sampling points was measured. There were no significant differences between group mean copy numbers. The pharmacokinetics (PK) of the baloxavir-group at 72 hr post treatment was 24.5±4.03 ng/mL baloxavir in plasma ±SD. XA, baloxavir; OST, oseltamivir.

FIGS. 13A-13C. Results of the recipient ferrets of Experiment 3 of Example 2. FIG. 13A shows the $TCID_{50}$ results. 2/4 baloxavir-treated donors were shedding infectious virus at 4 DPI endpoint, compared to 4/4 oseltamivir-group and 4/4 placebo-group donors FIG. 13B shows the qRT-PCR results. Viral RNA was detected in 3/4 baloxavir-treated donors compared to 4/4 oseltamivir-group and 4/4 placebo-group donors FIG. 13C shows the Serology results. All recipient sera from all groups demonstrated antibody responses to donor virus. $TCID_{50}$-negative baloxavir-group recipients (2/4) demonstrated reduced antibody titres (>16 fold change) compared to $TCID_{50}$-positive ferrets. '-' no antibody response observed. *Ferret 11333 (placebo) reached humane endpoint at 4 DPE, therefore has been excluded from serology analysis.

FIG. 14. Summary of the effect of baloxavir on donor ferrets in Experiments 1-3 of Example 2. Baloxavir-treatment rapidly reduces shedding of infectious virus in the upper respiratory tract. No baloxavir-treated ferrets were shedding detectable infectious virus at donor endpoint in each experiment.

FIG. 15. Summary of the effect of baloxavir on contact transmission in Experiments 1-3 of Example 2. The placebo-group shows that the frequency of contact transmission of A/Perth/265/2009 to naïve ferrets is 100% in the used model. Oseltamivir-treatment does not reduce contact transmission to naïve ferrets. 100% of oseltamivir-recipients demonstrate evidence of infection by $TCID_{50}$, qRT-PCR and serology in all experimental conditions. Baloxavir-treatment reduces the frequency of contact transmission compared to oseltamivir or placebo. Baloxavir-treatment at 1 DPI reduces frequency of infectious viral shedding in recipients to 25%. No difference was observed when co-housing of recipients is delayed by 24 hr. Baloxavir-treatment at 2 DPI reduces the frequency of infectious viral shedding in recipients to 50%. However, viral copies and serum antibody responses were detected in baloxavir-group recipients demonstrating no evidence of infectious shedding in the upper respiratory tract (URT), indicating exposure to virus but not a productive infection.

FIG. 16. Simulation of the prevention of an influenza epidemic during a seasonal flu by baloxavir-treatment. See text for details.

FIG. 17. Simulation of the prevention of an influenza pandemic by baloxavir-treatment. See text for details.

FIG. 18. Canadian Acute Respiratory Illness and Flu Sale (CARIFS)

DETAILED DESCRIPTION

As shown in the appended Examples, the compound to be used in the present invention has the advantageous effect that it reduces transmission. Therefore, this compound reduces the probability that an influenza epidemic or pandemic arises, or reduces the expansion of an existing influenza epidemic or pandemic. The compound to be used in the present invention is also a valuable tool for weakening the effects of a bioterrorist attack which deals with an influenza virus, such as an epidemic of pandemic influenza virus. Thus, the compound is particularly useful in the treatment of a specific type of an influenza virus infection, i.e. an infection which is caused by an influenza virus strain which has epidemic or pandemic potential. The unexpected technical effect of the compound to be used in the present invention to reduce transmission of the influenza virus clearly leads to a new clinical situation. Indeed, having this advantageous technical effect in mind the attending physician will particularly treat those patients with this compound who might cause (e.g. economic or social) damage if his/her infectiousness is not reduced. Such patients are, for example, patients who have personal contact to individuals of an influenza risk group, such as individuals which are at high risk for obtaining an influenza virus infection or who have an increased risk for obtaining severe influenza-related complications (e.g. elderly, young children, severely sick or immunocompromised persons). For example, treatment with the compound to be used in the present invention is highly beneficial for influenza patients who stay at home during their influenza virus infection but have contact to household members during their influenza virus infection, e.g. to young children. In addition, due to its advantageous property to reduce influenza transmission, the compound of the present invention may be used in the treatment of persons which are essential for the functioning of the society, which would allow these essential persons to continue working during their influenza virus infection without infecting colleagues or other contact persons. For example, the compound to be used in the present invention may advantageously used for the treatment of health personnel, particularly at the beginning of influenza epidemic or pandemic situation. The compound may also be used for the treatment of a patient who will have a lot of personal contact during his/her influenza virus infection, e.g. because he/she will have to fly in an airplane. Indeed, in the past several airplanes have to be quarantined because of a sudden outbreak of a disease, particularly during long-distance flights. Thus, the means and methods provided herein advantageously reduce the social and economic implications which are associated with influenza virus infections.

It is indicated that the effect of a given drug to reduce transmission cannot be concluded from the effectiveness of the drug against influenza (e.g. from the effectiveness of the drug to reduce influenza symptoms, viral burden, virus shedding or viral RNA). Indeed, the appended Examples show that oseltamivir, which is a commonly known and effective anti-influenza drug, does not at all prevent transmission of the influenza virus. The appended Examples also show that the viral RNA present in nasal wash of influenza infected subjects is identical in subjects treated with the compound of the present invention (in particular baloxavir marboxil), oseltamivir or placebo (see, e.g., FIGS. 6, 9 and 12). However, because of an unknown reason the viral transmission was significantly reduced in the baloxavir-treated subjects as compared to the oseltamivir- or placebo-treated subjects.

The fact that an anti-influenza drug reduces the symptoms of influenza does not at all indicate that this drug is also suitable for the reduction of transmission of the influenza virus. Influenza symptoms may remain even after clearance of the virus, and burden and virus shedding, and and therefore cannot predict the effectiveness on reducing transmission unless there is well-organized non-clinical study which imitates models in human. The transmission (e.g. in a household) is influenced by many factors. Therefore, from the fact that a given drug reduces viral shedding or viral burden it cannot be directly concluded that this drug also reduces transmission.

In addition, there is not an absolute correlation between virus shedding in the nose/throat and transmission. In humans for example H5N1 viruses reach very high titers in infected patients but do not transmit through the air or between people. In the ferret model a tight window of contagiousness that did not necessarily correlate with the timing of peak virus shedding was shown (Roberts, *PLoS One* 7.8 (2012): e43303). Moreover, it has been shown by the inventors that transmission does not correlate with clinical signs, so reduction of symptoms does not make reduction of transmission obvious. Indeed there is consensus that much of influenza transmission is asymptomatic or presymptomatic (Fraser, *Proceedings of the National Academy of Sciences* 101.16 (2004): 6146-6151). Thus, the fact that a known medicament is effective in the treatment of influenza does not at all indicate that this medicament is also effective in the reduction of transmission of the influenza virus. However, in the context of the present invention it has surprisingly been found that baloxavir marboxil significantly reduces transmission of the influenza virus.

As described above, the present invention is directed to the treatment of an influenza patient whose infectivity is to be prevented or reduced. Indeed, in accordance with the present invention the term "prevents transmission" includes that the compound "reduces transmission" as compared to a control patient to whom the compound to be used in the present invention is not administered. Herein the influenza patient whose infectivity is to be prevented or reduced is referred to as "index patient" (or "patient zero"). This patient, who is further defined below, can be any person who has an influenza virus infection and whose infectivity is to be prevented or reduced for any reason.

The compound to be used in the present invention reduces infectivity of the influenza virus of the index patient. Herein the term "infectivity" means the ability of a pathogen such as an influenza virus to establish an infection in another host. Herein the terms "infectivity" and "transmissibility" have the same meaning, and define the frequency the pathogen spreads among hosts, including hosts that are in a parent-child relationship and hosts that are not in a parent-child relationship. Thus, in accordance with the present invention the compound reduces the ability of the influenza virus of the treated index patient to establish an infection in another host. Or, in other words, the compound to be used in the present invention reduces the frequency with which the influenza virus of the index patient infects other hosts.

The appended Examples surprisingly show that transmission of an influenza virus can be reduced directly after administration of the compound to be used in the present invention. Furthermore, the appended Examples also document that the infectiousness of the treated index patient decreases even more within 24 hours from administration of the compound. Therefore, it is preferred in the context of the present invention that the index patient does not have personal contact with other persons (i.e. contact persons) until 1 hour or until 2, 4, 6, 8, 10, 12, 14, 16, 18, 20, 22, 24, 26, 28, 30, or 32 hours after administration of the compound to be used in the present invention. The time spans mentioned here refer to minimum time spans. For example, the time span "2 hours after administration" also includes longer periods such as 2.5 hours after administration and so on. Indeed, the invention encompasses that the index patient does not have personal contact to contact persons until one or two days (or one day and one or two nights) after administration of the compound to be used in the present invention. For example, the index patient may stay in isolation in hospital for one day (or for one day and one or two nights), so that personal contact to other persons is prevented during this period of time.

In line with this, in one aspect of the present invention the rate of transmission of the influenza virus from the index patient is reduced within one hour to 24 hours from the Pt administration of the compound. The rate of transmission of the influenza virus from the index patient may also be reduced within 2, 4, 6, 8, 10, 12, 14, 16, 18, 20, 22, 24, 26, 28, 30, or 32 hours from the Pt administration of the compound. Accordingly, the time span can be elongated. Thus, in accordance with the present invention the rate of transmission of the influenza virus from the index patient reduces within one hour to 32 hours (e.g. within 2, 4, 6, 8, 10, 12, 14, 16, 18, 20, 22, 24, 26, 28, 30, or 32 hours) from the Pt administration of the compound.

Thus, the compound to be used in the present invention reduces the rate of transmission of the influenza virus from the treated index patient to a contact person of the treated index patient. The rate of transmission of the influenza virus from the treated index patient may be reduced to 70% or less, preferably to 50% or less, more preferably to 30% or less, as compared to the rate of transmission of the influenza virus from a control patient.

Herein the "rate of transmission" (also called "transmission rate") corresponds to the percentage of infected subjects among the contact persons of the influenza-infected patient (i.e. of the index patient or of the control patient, respectively) within a specified period of time. Thus, the "transmission rate" is the number of new cases (of an infection with an influenza virus strain which stems from the index patient or from a control patient, respectively) within a specified time period divided by the population at risk. The "population at risk" is preferably the number of persons who had personal contact to the index patient or to the control patient, respectively, during his/her influenza virus infection. An influenza virus can usually be transmitted one day before influenza symptoms arise and until the duration of the influenza symptoms and recovery of the disease. Therefore, the "population at risk" may be the number of persons who had personal contact to the index patient or to the control patient, respectively, one day before influenza symptoms arise and until the duration of the influenza symptoms. Preferably, the "population at risk" does not include the persons who received an influenza vaccination. As described herein above and below, the "rate of transmission" is reduced after administration of the compound to be used in the invention. Therefore, the effect of the compound on the rate of transmission is measured after administration of the compound. In particular, for evaluating the effect of the compound on the rate of transmission, the "population at risk" may be defined as the number of persons (e.g. persons who are not vaccinated against influenza) who had personal contact to the index patient during the period of time starting with the administration of the compound and ending with the end of the influenza symptoms. In line with this, the "population at risk" of the control patient may be defined as the number of persons (e.g. persons who are not vaccinated against influenza) who had personal contact to the control patient during the period of time starting with the administration of an anti-influenza drug other than the compound, or if no anti-influenza drug is administered starting at the corresponding time point in view of the disease process of influenza, and ending with the end of the influenza symptoms and recovery from the disease.

As described above, in accordance with the present invention the compound reduces the rate of transmission of the influenza virus of the index patient (i.e. the infectiousness of the index patient) to 70% or less, preferably to 50% or less, more preferably to 30% or less, as compared to the rate of transmission of the influenza virus of a control patient who is not treated with the compound (i.e. as compared to the infectiousness of a control patient who is not treated with the compound). In seasonal flu including influenza epidemics the influenza virus is transmitted from one patient to approximately 1.35 subjects over 5 days. Thus, if the index patient is infected with an influenza strain of a seasonal flu (including an epidemic influenza strain but not a pandemic influenza strain), then the compound reduces the amount of subjects to which the virus is transmitted on average to approximately 0.945 subjects (i.e. 70% transmission) or less over 5 days, preferably on average to approximately 0.675 subjects (i.e. 50% transmission) or less over 5 days, more preferably on average to approximately 0.405 subjects (i.e. 30% transmission) or less over 5 days. In pandemic flu the influenza virus is transmitted from one patient to approximately 2.9 subjects over 6 days. Thus, if the index patient is infected with an influenza strain of a pandemic flu, then the compound reduces the amount of subjects to which the virus is transmitted on average to approximately 2.03 subjects (i.e. 70% transmission) or less over 6 days, preferably on average to approximately 1.45 subjects (i.e. 50% transmission) or less over 6 days, more preferably on average to approximately 0.87 subjects (i.e. 30% transmission) or less over 6 days.

Most individuals with an influenza infection are advised to stay at home until they have been afebrile for at least 24 hours, which puts other household members at risk of infection (Centers for Disease Control and Prevention. The flu: what to do if you get sick. 9 Mar. 2018). Once one household member is infected with influenza, the risk of transmission to a household contact can be up to 38%, with a delay between onset in the index patient and infection of the household contact of around 3 days (Tsang, Trends Microbiol 2016; 24(2):123-133). As described above, the compound to be used in the present invention reduced the rate of transmission of the influenza virus from the treated index patient to 70% or less, preferably to 50% or less, more preferably to 30% or less. Thus, treatment of the index patient with said compound reduces the risk of transmission of the influenza virus to a household contact to approximately 27% or less (i.e. 70%), preferably to approximately 19% or less (i.e. 50%), more preferably to approximately 11.4% or less (i.e. 30%). This is a considerable advantage in the prevention of influenza epidemics or pandemics.

It is shown in the appended Examples that the compound to be used in the present invention decreases the load of virus shed into the upper respiratory tract. Thus, in accordance with the present invention the compound decreases the load of virus shed into the upper respiratory tract of the index patient as compared to the load of virus shed into the upper respiratory tract of a control patient, wherein the control patient has an influenza virus infection and has not been administered with the compound.

The control patient may be any patient who has an influenza virus infection and who is not treated with the compound to be used in the present invention. Thus, in accordance with the present invention the control patient has an influenza virus infection and has not been administered with the compound. However, the control patient may be administered with an anti-influenza drug except for the compound of formula (I) or (II) or a pharmaceutically acceptable salt thereof. For example, the control patient may be administered with oseltamivir. Thus, in one aspect of the present invention the control patient has been administered with any anti-influenza drug except for the compound of formula (I) or (II) or a pharmaceutically acceptable salt thereof. For example, the control patient may have been administered with oseltamivir. In another aspect of the present invention the control patient has not been administered with an anti-influenza drug, e.g., has not been administered with oseltamivir. Oseltamivir may be administered in a 75 mg dose twice per day over 5 days. The human dose of oseltamivir is commonly known in the art. For example, for adults and adolescents (13 years and older) 75 mg is usually given twice daily for 5 days. The dose for pediatric patients who are 1 to 12 years of age is based on weight and this dose is usually given twice daily for 5 days. The dose for pediatric patients who are 2 weeks to less than 1 year of age is usually 3 mg/kg twice daily for 5 days. The control patient has an influenza virus stain which is identical with the influenza stain of the index patient to whom the control patient is compared. For example, if the index patient has a pandemic influenza virus stain, then the control patient to whom the index patient is compared has the same pandemic influenza virus strain.

The person skilled in the art is readily in the position to recognize whether transmission of the influenza virus from the (treated) index patient or from the control patient has occurred. For example, the transmission may be occurred when at least one contact person of the treated index patient or of the control patient obtains an influenza virus infection after having personal contact to the treated index patient or to the control patient, respectively. The contact person of the treated index patient is preferably a person who:
 (i) did not have an influenza virus infection at the time point when the compound was administered to the index patient for the first time; and
 (ii) had personal contact to the treated index patient during the influenza virus infection of the index patient.

Regarding item (ii), directly above, it is preferred that the contact person had personal contact to the treated index patient within 10 days from the administration of the compound to the index patient. Thus, with regard to item (ii), directly above, it is preferred that the contact person had personal contact to the treated index patient within a period of time starting with the administration of the compound; and ending 5 to 10 days (e.g. 9 days or 5 days) after the administration of the compound.

The contact person of the control patient is preferably a person who:
 (i) did not have an influenza virus infection at the time point when the anti-influenza drug was administered to the control patient for the first time; or, if no anti-influenza drug was administered to the control patient at the corresponding time point in view of the disease process of influenza; and
 (ii) had personal contact to the control patient during the influenza virus infection of the control patient.

Regarding item (ii), directly above, it is preferred that the contact person had personal contact to the control patient within 10 days from the administration of the anti-influenza drug to the control patient; or if no anti-influenza drug was administered within the corresponding period of time in view of the disease process of influenza. Thus, with regard to item (ii), directly above, it is preferred that the contact person had personal contact to the control patient within a period of time starting with the administration of the anti-influenza drug to the control patient; or if no anti-influenza drug was administered starting at the corresponding time point in view of the disease process of influenza; and ending 5 to 10 days (e.g. 9 days or 5 days) after the administration of the anti-influenza drug; or if no anti-influenza drug is administered ending at the corresponding time point in view of the disease process of influenza.

Of course, the contact person does not need to have personal contact to the index patient or the control patient, respectively, at every day within the 10 days mentioned above. Rather, the contact person can, e.g., have personal contact to the index patient or control patient, respectively, at only one day within these 10 days. For example, the contact person may have personal contact to the index patient or to the control patient (e.g. due to a joint household) at about 7 out of 9 days.

Herein, when counting the days after administration of the compound to the index patient or the other anti-influenza drug to the control patient, the day of the administration is considered to be "day 0". Thus, day 1 (i.e. one day after administration of the compound or the other anti-influenza drug, respectively) is the day following the day of the administration and so on. Accordingly, 10 days after administration of the compound or of the other anti-influenza drug refers to the day which is approximately 240 hours from administration of the compound or of the other anti-influenza drug, respectively.

As mentioned above, in accordance with the present invention a contact person of the treated index patient or of the control patient is a person who:
 (i) with respect to the index patient: did not have an influenza virus infection at the time point when the compound was administered to the index patient for the first time; or with respect to the control patient: did not have an influenza virus infection at the time point when the anti-influenza drug was administered to the control patient for the first time; or, if no anti-influenza drug was administered to the control patient at the corresponding time point in view of the disease process of influenza; and
 (ii) with respect to the index patient: had personal contact to the treated index patient during the influenza virus infection of the index patient; or with respect to the control patient: had personal contact to the control patient during the influenza virus infection of the control patient.

In accordance with the present invention, not having an influenza virus infection preferably means being PCR-negative for an influenza virus (e.g. in the nasopharyngeal swab). Thus, it is preferred that at the time point as defined in (i), above, the contact person was PCR-negative for influenza.

The PCR detection and quantification of the influenza virus is commonly known in the art. For Example, real-time reverse transcription PCR (RT-PCR) amplification of the influenza matrix gene may be employed as the method for determining the presence or absence, or the quantity of influenza RNA. Influenza virus RNA extraction and purification is a routine technique and can, e.g., be performed by using a MagNA Pure LC 1.0 or 2.0 isolation station (Roche Applied Science, product #05197686001). To perform the test, nucleic acids are extracted from swab specimen aliquots using the MagNA Pure LC isolation station and the MagNA Pure LC nucleic acid extraction kit according to the manufacturer's instructions (Roche Applied Science). Reverse transcription and amplification reactions can be set up using Taqman Fast Virus Mastermix. During clinical analysis, a 4 point (low, middle and high) influenza A and B standard curve with known virus particles/ml can be used as control and can accompany every run. To monitor the whole process from isolation to real-time detection, a universal internal control, the Phocine Distemper Virus (PDV), may be added to each isolate. In addition, to monitor contamination in every isolation a No Amplification Control (NAC) may be included for every PCR mix that is made. The positive controls must give a positive signal that lies between specified action limits. If the value of the positive control lies outside the action limit, all samples tested with the same PCR mix need to be retested. If the negative control gives a positive signal for influenza, all samples run with the same PCR mix need to be retested. The output of the influenza RT-PCR assay is what is known as a Cycle threshold, or Ct value and a Ct value is recorded for each test. The Ct values are converted to quantitative virus particles/ml values with the standard curves ran concurrent with the samples.

For influenza A positive subjects an influenza A subtype PCR assay can also be performed. More specifically, for influenza A positive subjects, sub-typing can be performed directly from a subject's swab sample using a real time RT-PCR assay. RNA can be isolated from clinical isolates as described above using the Roche MagNA Pure Total Nucleic Acid kit, and can be amplified using a one-step RT-PCR with influenza A-subtype specific primers. Further methods for the detection of particular influenza virus subtypes including suitable primer sequences are commonly known in the art, and described, e.g., in the "WHO information of the molecular detection of influenza viruses" of July 2017.

The skilled person can easily determine the time point within an influenza virus infection which corresponds to a given influenza disease state (i.e. which corresponds to a given state within the disease process of influenza). More specifically, it is commonly known in the art that the disease process of influenza can be monitored. For example, the disease process of influenza may be monitored by monitoring the clinical symptoms and/or virology measures. The clinical symptoms may be monitored by:

(i) determining the score for cough and nasal symptoms (items 14 and 15 of the Canadian Acute Respiratory Illness and Flu Scale (CARIFS);
(ii) asking the patient or his/her caretaker whether (and when) the patient was able to return to day care/school/work, or resume his/her normal daily activity in the same way as performed prior to developing the influenza virus infection; and/or
(iii) if the patient had already returned to afebrile state (and preferably remained so for at least 21.5 hours), determining the time point when the patient first returns to afebrile state (i.e. tympanic temperature ≤37.2° C.).

The CARIFS is commonly known in the art and shown in FIG. 18.

The virology measures may be monitored, e.g., by measuring the viral titer or viral shedding.

In accordance with the present invention the personal contact between the contact person and the index patient or the control patient, respectively, is a personal contact which allows transmission of the influenza virus. For example, the personal contact may be a contact which allows airborne transmission and/or direct contact transmission, preferably only airborne transmission. Contact transmission refers to direct virus transfer from an infected person to a susceptible individual, e.g. via contaminated hands (direct contact transmission) or indirect virus transfer via intermediate objects (fomites, indirect contact transmission). Transmission of virus through the air (i.e. airborne transmission) can occur via droplets or aerosols. The commonly accepted cut-off size between the large droplets and small aerosols is 5 μm (Kutter, *Current opinion in virology*, 28 (2018): 142-151). Droplets generated during coughing, sneezing or talking do not remain suspended in air. They usually remain <17 min in air and travel less than 1 m before settling on the mucosa of close contacts (i.e. persons who have personal contact to the infected patient) or on environmental surfaces. Aerosols have a slow settling velocity, thus they remain suspended in the air longer and can travel long distances which are longer than 1 m (Kutter, *Current opinion in virology*, 28 (2018): 142-151). In studies for analyzing transmissibility of the influenza virus, influenza virus RNA was detected in the air up to 3.7 m away from patients with the majority of viral RNA contained in aerosols (<5 μm) (Kutter, *Current opinion in virology*, 28 (2018): 142-151).

Thus, in accordance with the present invention the personal contact which allows direct contact transmission is body contact between the influenza-infected patient (i.e. the index patient or the control patient, respectively) and the contact person, e.g. hand shake etc. It has been shown that influenza A viruses survive up to 3 days when they are inoculated on banknotes (Thomas, *Appl. Environ. Microbiol.* 74.10 (2008): 3002-3007). The same inoculum in the presence of respiratory mucus showed a striking increase in survival time (up to 17 days, Thomas, *Appl. Environ. Microbiol.* 74.10 (2008): 3002-3007). When nasopharyngeal secretions of naturally infected children were used, influenza virus survived for at least 48 h in one-third of the cases (Thomas, *Appl. Environ. Microbiol.* 74.10 (2008): 3002-3007). Accordingly, in the context of the present invention the personal contact between the influenza-infected patient (i.e. the index patient or the control patient) may allow indirect contact transmission. Said personal contact which allows indirect contact transmission may be body contact of the contact person to a fomite after an influenza-infected patient (i.e. the index patient or the control patient) had personal contact to the fomite. For example, the influenza-infected patient may have touched the fomite by his/her hands or may have breathed on the fomite. The time span between the personal contact of the influenza-infected patient and the fomite and the personal contact of the contact person and the fomite may be 3 days or less, preferably 48 hours or less.

Respiratory viruses like the influenza virus replicate in the respiratory tract from where they are subsequently shed and transmitted via respiratory secretions by airborne transmission. In the present invention the personal contact which allows airborne transmission is a distance between the influenza-infected patient (i.e. the index patient or the control patient, respectively) and the contact person which is up to 3.7 meter. Influenza is mainly transmitted via respiratory droplet transmission. Therefore, it is preferred that during the personal contact of the contact person and the index patient or the control patient, respectively, these persons (i.e. the contact person and the index patient or the control patient, respectively) have a distance of up to 1 meter, and more preferably less than 1 meter.

With enhanced equipment transmission of the influenza virus can be detected immediately after transmission. Usually, transmission is detected one day after the transmission occured. In one aspect of the present invention transmission from the treated index patient has occurred when an influenza virus can be detected in at least one contact person of the treated index patient. In a preferred aspect of the invention transmission from the treated index patient has occurred if an influenza virus can be detected in at least one contact person of the treated index patient within 15 days from the administration of the compound. In one aspect of the invention, transmission from the treated index patient has occurred if an influenza virus can be detected in at least one contact person of the treated index patient within 10 days from the administration of the compound to the index patient. If transmission occurred, the influenza virus may be detected in the contact person even within a longer period of time, e.g. within 15 days from the administration of the compound to the index patient. An even longer course of the disease, e.g. up to three weeks or longer, is particularly expected if the virus mutates.

In one aspect of the present invention transmission from the control patient has occurred if an influenza virus can be detected in at least one contact person of the control patient. In a preferred aspect of the invention transmission from the control patient has occurred if an influenza virus can be detected in at least one contact person of the control patient within 15 days from the administration of the other anti-influenza drug to the control patient; or, if no anti-influenza drug was administered to the control patient within the corresponding period of time in view of the disease process of influenza. In one aspect of the invention, transmission from the control patient has occurred if an influenza virus can be detected in at least one contact person of the control patient within 10 days from the administration of the other anti-influenza drug; or, if no anti-influenza drug was administered to the control patient within the corresponding period of time in view of the disease process of influenza. As mentioned above, if transmission occurred, the influenza virus may be detected in the contact person even within a longer period of time, e.g. within 15 days from the administration of the other anti-influenza drug to the control patient; or, if no anti-influenza drug was administered to the control patient within the corresponding period of time in view of the disease process of influenza. As also mentioned, an even longer course of the disease, e.g., up to three weeks or longer, is particularly expected if the virus mutates.

In the context of the present invention the rate of transmission may be measured by testing at least one contact person of the treated index patient or of the control patient, respectively, for an influenza virus infection. The rate of transmission may be measured by testing at least one contact person of the treated index patient or of the control patient, respectively, for an influenza virus infection within 10 days from the administration of the compound to the treated index patient, or within 10 days from the administration of the other anti-influenza drug to the control patient, or, if no anti-influenza drug was administered to the control patient within 10 days from the corresponding time point in view of the disease process of influenza.

Influenza is a severe disease and recovery can take several days to weeks. Therefore, in accordance with the present invention the rate of transmission may also be measured by testing at least one (e.g. at least 2) contact person(s) of the treated index patient or of the control patient, respectively, for an influenza virus infection within 20 days from the administration of the compound to the treated index patient, or within 20 days from the administration of the other anti-influenza drug to the control patient, or, if no anti-influenza drug was administered to the control patient within 20 days from the corresponding time point in view of the disease process of influenza. For example, the rate of transmission may be measured by testing several contact persons (e.g. at least 2) of the index patient and of the control patient, respectively, for an influenza virus infection. For example, the contact persons may be tested for an influenza virus infection at various time points, e.g., about 3 days, 5 days, 10 days, 15 days and/or 20 days after administration of the compound to the index patient, or after administration of the other anti-influenza drug to the control patient, or if no anti-influenza drug was administered to the control patient at the corresponding time point(s) in view of the disease process of influenza.

In one aspect of the present invention an influenza virus infection is present if the influenza virus can be detected (e.g. in a contact person of the index patient or of the control patient, respectively). The influenza virus may be detected via PCR. In addition or alternatively the influenza virus may be detected by using an influenza test kit. For example, a Rapid Influenza Diagnostic Tests (RIDT) may be used for detecting the influenza virus. RIDTs are immunoassays that can identify the presence of influenza A or B viral nucleoprotein antigens in respiratory specimens, and display the result in a qualitative way (positive vs. negative) (Ali T, *Clin Infect Dis.* 2004 Mar. 1; 38(5):760-2). RIDT assays are ELISA based assays which are less accurate than PCR, but have the advantage that they are cheaper and faster, which is a considerable benefit in particular in an epidemic or pandemic situation.

The influenza virus may further be detected by using the Roche Cobas® Liat® point of care (POC) polymerase chain reaction (PCR) system (Chen, *Eur J Microbiol Immunol (Bp).* 2015; 5(4):236-245). The Cobas® Liat® system enables rapid and accurate diagnosis of influenza A or B nasopharyngeal swab specimens. The system comprises the Cobas® Liat® Analyzer and the Cobas® Influenza A/B assay. The detection of the influenza virus may also be carried out by using a PCR-based molecular test (Prodesse ProFlu+ assay, Chen, *Eur J Microbiol Immunol (Bp).* 2015; 5(4):236-245) or the Alere i Influenza A & B rapid PCR system (Merckx, *Ann Intern Med.* 2017; 167(6):394-409).

The detection of the influenza virus may further be performed by testing whether infectious virus particles are present, e.g. by measuring the virus titer and/or virus shedding. The virus titer (e.g. in the nasal mucosa) can be determined by the plaque assay (e.g. as performed in the appended Examples and as described below).

The determination of the infectious titer of virus is commonly known in the art. For example, the infectious virus titer can be measured by a quantitative culture assay, i.e. the "plaque assay". In particular, the infectious titer of viruses may be determined with a quantitative culture assay that expresses the amount of virus present as a median tissue culture infective dose ($TCID_{50}$) per milliliter. In order to determine the infectious titer of a given sample, clinical specimens may be serially diluted and incubated on MDCK cells. The primary read out for this assay exploits the ability of influenza viruses to bind sialylated glycans on red blood cells causing agglutination. The measurement of agglutination mediated by adding red blood cells to a dilution series of influenza virus can then be used to quantify the viral titer. For circulating virus isolates that have lost the capacity to agglutinate red blood cells (e.g. current isolates of the respective season), an ELISA based read out of influenza nucleoprotein (NP) can be applied. The $TCID_{50}$ assay method may be performed as a unified protocol that allows for the NP-ELISA to be performed using the same assay plate if the virus is a non-agglutinating strain. For clinical studies, assay analysis using the red blood cell agglutination read out can be followed by NP-ELISA read out for influenza virus subtypes (e.g. H3) (and non-typable viruses). Negative controls should be negative and positive controls should be positive for a plate to be valid. The Karber method (Karber, G., 1931, Beitrag zur kollektiven Behandlung Pharmakologischer Reihenversuche, Archiv für Experimentelle Pathologie and Pharmakologie, 162, 480-487) may be used to calculate the virus titer ($TCID_{50}$).

For example, in order to determine the infectious virus titer the virus may first be grown from a nasal wash sample, and subsequently, the infectious virus titer may be measured as described in the following:

Growth of virus from nasal wash sample may be performed as follows. MDCK cells may be maintained in cell culture medium until use. 1 day prior to assay, MDCK cells may be seeded in 96-well flat-bottom plates at $3.5 \times 10^4$ cells per well in cell culture medium. Trypsin-EDTA may be required to detach cells from culture flask. 24 h incubation at 37° C., 5% CO2 results in cell monolayers at 80-100% confluency. In triplicate, 20 μL of thawed nasal wash sample may be added to 180 μL of infection medium to perform a 10-fold serial dilution. MDCK monolayers can then be washed twice with PBS, and 100 μL of diluted samples added to the cells for 2 h incubation at 37° C., 5% CO2. The final row of the plate may be left without sample to act as negative control. Following this, the virus inoculum may be removed and replaced with 200 μL of fresh infection medium. The plates can then be incubated at 37° C., 5% CO2 for 96 hours.

Measurement of viral titers in nasal wash may be performed as follows: Following 96 hour incubation, viral titers of nasal wash samples cultured in MDCK plates may be read by haemagglutination assay. Twenty-five μL of MDCK supernatant from each well may be transferred to corresponding wells of a new 96-well U-bottom plate, and mixed with 25 μL of 1% (v/v) turkey red blood cells by gentle tapping. Plates may be incubated at room temperature for 30 min, and the pattern of agglutination recorded. Virus titers can be calculated using the method described by Reed and Muench (Reed, L. J. and H. Muench, *American Journal of Epidemiology*, 1938. 27(3): p. 493-497), and can be expressed as $\log_{10}$ $TCID_{50}$/mL.

Also the presence of at least one symptom of influenza indicates that an influenza virus infection is present. Therefore, in accordance with the present invention an influenza virus infection is present if:
  (i) the influenza virus can be detected; and/or
  (ii) at least one symptom of an influenza virus infection is present.

In one aspect of the present invention an influenza virus infection is present if both features apply, i.e. the influenza virus can be detected, and at least one symptom of an influenza virus infection is present. Thus, the rate of transmission (i.e. infectiousness) of the treated index patient or of the control patient may be measured by testing whether the influenza virus can be detected, and optionally further testing whether influenza symptoms are present in person(s) who had personal contact to the treated index patient or to the control patient, respectively. For example, it may be tested whether at least one symptom of an influenza virus infection is present. Said at least one symptom of an influenza virus infection may be a sudden onset of fever, chills, headache, muscle and/or joint pain, cough, fatigue, sore throat and/or nasal congestion. It may also be tested whether the body temperature reaches 38° C. to 40° C. within 24 hours from the onset of influenza symptoms (Wright, Fields Virology. 5th ed. (2). Wolters Kluwer Health/Lippincott Williams & Wilkins; 2007. P. 1691-1740; Monto, Arch Intern Med. 2000; 160:3243-3247). Based on these symptoms, influenza virus infection tends to be a severe illness and can be discriminated from the common cold.

Herein the onset of influenza symptoms may be defined as either:
  (i) the time point of the first increase in body temperature (an increase of at least 1° C. from normal body temperature); or
  (ii) the time point when the patient experiences at least one general or respiratory symptom. Preferably, the time point of the onset of influenza symptoms is confirmed by verifying that within 24 hours from the time point of (i) and (ii) above, the body temperature reaches 38° C. to 40° C.

In addition or alternatively, the diagnosis of influenza may be confirmed by all of the following:
  (i) Fever ≥38° C. (axillary) in the predose examinations or >4 hours after dosing of antipyretics if they were taken.
  (ii) At least one of the following general systemic symptoms associated with influenza with a severity of moderate or greater:
    (ii)-1 Headache;
    (ii)-2 Feverishness or chills;
    (ii)-3 Muscle or joint pain;
    (ii)-4 Fatigue.
  (iii) At least one of the following respiratory symptoms associated with influenza with a severity of moderate or greater:
    (iii)-1 Cough;
    (iii)-2 Sore throat;
    (iii)-3 Nasal congestion.
    (iii)-4 Influenza A or B infection confirmed by POC PCR testing.

Transmission of the influenza virus from the index patient or the control patient to the contact person may be verified by different means. For example, it can be assumed that transmission occurred if an influenza virus is detected in the contact person (e.g. via PCR), and the index patient or the control patient was the first (or even only) influenza infected person to whom the contact person had personal contact directly before the identification of the influenza virus in the contact person, e.g. within the last four weeks (preferably within the last two weeks, or more preferably within the last 7 days) directly before the identification of the influenza virus in the contact person. In one aspect of the present invention the transmission from the treated index patient has occurred when an influenza virus strain can be detected in at least one contact person of the treated index patient, and when said influenza virus strain is identical with the influenza virus strain of the treated index patient, and the transmission from the control patient has occurred when an influenza virus strain can be detected in at least one contact person of the control patient, and when said influenza virus strain is identical with the influenza virus strain of the control patient. Thus, in one aspect of the present invention, the transmission from the treated index patient has occurred when at least one contact person of the treated index patient has an influenza virus infection with an influenza virus strain which is identical with the influenza virus strain of the treated index patient, and the transmission from the control patient has occurred when at least one contact person of the control patient has an influenza virus infection with an influenza virus strain which is identical with the influenza virus strain of the control patient.

For example, if a contact person (e.g. a household contact) develops PCR-confirmed influenza A or B, nasopharyngeal swab of the contact person may be used to sequence the viral genome in order to test whether the influenza virus stems from (i.e. descends from) the index patient or the control patient, respectively. Methods for sequencing the viral genome are commonly known in the art and also described below. The skilled person is easily in the position to determine whether an influenza virus stems from the index patient or the control patient, respectively. For example, the skilled person will recognize that transmission has occurred if the viral genome of the influenza virus of the contact person is identical with the viral genome of the influenza virus of the index patient or the control patient, respectively. However, the influenza virus may also mutate during or after transmission from the index patient or the control patient to the contact patient. Therefore, transmission has also occurred if the viral genome of the influenza virus of the contact person is identical with the viral genome of the influenza virus of the index patient or the control patient, respectively, beside one to several nucleotide differences (i.e. point mutations).

In order to determine whether transmission of an influenza virus of an index patient to a contact person or of a control patient to a contact person has occurred, phylogenetic trees and genetic distance measurement may be conducted. More specifically, in order to determine whether transmission has occurred the methods as described in Example 4 may be used.

For example, a phylogenetic analysis (whole genome tree with bootstrap support of tree topology or clustering) and/or measurement of genetic distance between paired populations (e.g. L1-Norm) can be conducted for identifying transmission paris. Two factors influence the outcome of the analysis: first, the amount of available sequence data. To maximize this whole genome next-generation sequencing (WGNGS) can be conducted to increase granularity and discriminatory power (compared to Sanger sequencing and/or single gene sequencing). Second, the diversity in the community/meta-population sampled, such that the assessment that viruses from within household pairs are more similar to each other compared to an outgroup can be done with high confidence. More sequences obtained from a community increase diversity in this group and thus facilitate identification of real transmission pairs.

For example, $\geq 15$ index patients (IP), preferably at least 30-40 index patients (IP) may be used to develop a community distribution of pair wise distances, reflecting the community diversity, such that one can infer true transmission events (e.g. household transmission events) with sequence data, e.g., as described in McCrone, John T., et al. "Stochastic processes constrain the within and between host evolution of influenza virus." *Elife* 7 (2018): e35962. The methods as described in McCrone (*Elife* 7 (2018): e35962), such as the method which is described therein for the sequencing may be used. In the context of the present invention the analysis is preferably focused on the analysis of influenza A virus samples.

Both epidemiologic linkage and the genetic relatedness of viruses (e.g. in households) may be used to define transmission pairs and to exclude confounding from the background diversity in the community. A pair of individuals (e.g. within a household) may be considered an epidemiologically linked transmission pair if they had personal contact and are both positive for the same subtype of influenza virus within 7 days of each other. For example, all individuals who had personal contact to each other (e.g. in a household) with symptom onset within a 7 day window may be considered to be epidemiologically linked. The donor in each putative pair may be defined as the individual with the earlier onset of symptoms. A transmission event may be disregarded if there were multiple possible donors with the same day of symptom onset. Donor and recipients may not be allowed to have symptom onset on the same day, unless the individuals were both index patients (e.g. for the analyzed household).

Next, sequence data may be used to determine which of the epidemiologically linked pairs represent true transmission events as opposed to coincident community-acquired infections. The genetic distance between influenza populations from each putative transmission pair may be measured by L1-norm and these distances may be compared to those of randomly assigned community pairs within each season. Only individuals may be considered to be a true transmission pair if they have a genetic distance below the 5th percentile of the community distribution of randomly assigned pairs.

As mentioned above, the influenza virus is mainly transmitted by airborne transmission, particularly droplet infection. Therefore, in one aspect of the present invention the transmission of the influenza virus is direct contact transmission and/or airborne transmission, preferably airborne transmission. More preferably, the transmission is droplet infection.

As provided herein the compound to be used in the present invention has the advantageous property that it considerably reduces transmission of the influenza virus. Thus, said compound is particularly useful for the treatment of particular influenza infected patients, whose infectiousness is to be reduced. For example, it is particularly important to reduce the infectiousness of patients who might cause significant (e.g. social or economical) damage due to the transmission of their influenza virus. In one aspect of the present invention the treated index patient has personal contact to at least one person of an influenza risk group or to at least one person who is essential for the functioning of the society after administration of the compound to the index patient and during his/her influenza virus infection. The at least one person of an influenza risk group may be at least one person having an increased risk for obtaining an influenza virus infection or having an increased risk for obtaining an influenza-related complication. Said influenza-related complication may be at least one complication selected from the group consisting of hospitalization, sinusitis, otitis media, bronchitis and pneumonia. Said at least one person having an increased risk for obtaining an influenza-related complication may have an increased risk for dying because of the influenza virus infection. In one aspect of the present invention said at least one person having an increased risk for obtaining an influenza-related complication is an individual:

(i) having a chronic cardiovascular disease, a chronic pulmonary disease, a chronic metabolic disease a chronic renal disease, a cardiopulmonary disorder, and/or which is immunocompromised; and/or (ii) which is at least 65 years old, or younger than 5 years old.

In addition or alternatively, the at least one person having an increased risk for obtaining an influenza-related complication may be a seriously ill (e.g. hospitalized) patient.

As mentioned above, in one aspect of the present invention the treated index patient has personal contact to at least one person of an influenza risk group after administration of the compound to the index patient and during his/her influenza virus infection, wherein said person of an influenza risk group may be at least one person having an increased risk for obtaining an influenza virus infection. In the context of the present invention said at least one person having an increased risk for obtaining an influenza virus infection may be an individual for whom influenza vaccination is contraindicated. Said at least one person having an increased risk for obtaining an influenza virus infection may also be a person having a major health threat, a young child (e.g. a child which is younger than 5 years), an elderly person (e.g. a person being 65 years or older), or an immunocompromised person.

As mentioned above, the contact person of the index patient may be at least one person who is essential for the functioning of the society. Such a person who is essential for the functioning of the society may be a person who is essential for the functioning of the city or state. In accordance with the present invention said at least one person who is essential for the functioning of the society may be working as an essential service provider including a person who belongs to the fire personnel, police personnel, health care personnel, the personnel of an emergency response service, military, or government.

Staying at home during an influenza virus infection can be detrimental if the infected patient is an essential service provider. This particularly applies during an emergency situation. Therefore, the index patient himself/herself may be a person who is essential for the functioning of the society. Treatment of such an index patient with the compound to be used in the present invention will reduce (or even prevent) that the virus is transmitted from the index patient to other persons, so that the index patient will not necessarily have to stay at home during his/her influenza virus infection. For example, the index patient may be working as an essential service provider, e.g., may be a person belonging to the fire personnel, police personnel, health care personnel, or to the personnel of an emergency response service.

The index patient may be a person within an influenza epidemic or an influenza pandemic situation. The index patient may also be a person within a bioterrorist threat or bioterrorist attack situation, wherein an influenza virus plays a role in the bioterrorist threat or bioterrorist attack, respectively. Indeed, the impact of pandemic influenza is likely to be far greater, by orders of magnitude, than usual bioterrorism scenarios. Therefore, preventing or reducing influenza transmission would be major advantage during an epidemic, pandemic or bioterrorist situation. As mentioned above, experts anticipate that the next influenza pandemic will be associated with a high death toll and a high degree of illness requiring hospitalization, thus producing a considerable strain on health care resources. Thus, the index patient may be belonging to the health care personnel and the treatment of said index patient with the compound may be during an influenza epidemic or during an influenza pandemic. As also mentioned above, in developing countries, where health care resources are already strained and the general population is frequently weakened by poor health and nutritional status, the impact of influenza pandemics is likely to be greatest. Therefore, the index patient may belong to the population of a developing country.

Of course, reducing the rate of transmission is particularly advantageous (or even necessary) if the influenza-infected index patient has or will have personal contact to a lot of persons. Preferably, the index patient has personal contact to a lot of persons after administration of the compound to be used in the present invention. In one aspect of the present invention the treated index patient has personal contact to a lot of persons, e.g. to more than 10 persons, after administration of the compound (to the index patient) and during his/her influenza virus infection. For example, the index patient may have personal contact to a lot of persons in his/her household or in his/her job. In one aspect of the present invention the treated index patient visits a care facility (such as a nursing home, a nursery, or a hospital), an educational facility (such as a school or university), a public institution, a transportation facility, a vehicle, an aircraft and/or a shop, and has personal contact to a lot of persons, e.g. to more than 10 persons, after administration of the compound to the index patient and during his/her influenza virus infection.

Preferably, the transmission rate of the influenza virus from the treated index patient to household contacts is reduced. Accordingly, it is preferred that the treated index patient has household contacts. For example, the treated index patient may live in one household with children (preferably children which are not older than 5 years). In addition or alternatively, the treated index patient may have a job with a lot of human contact. It is preferred that at least one person of the household contact(s) and/or job contact(s) of the treated index patient is not vaccinated against influenza.

As mentioned above the treated index patient may have personal contact to a lot of persons, e.g., more than 10 persons (preferably more than 30, more preferably more than 50, even more preferably more than 100 persons) after administration of the compound and during his/her influenza virus infection. The appended Examples show that the rate of transmission is reduced in the treated subject directly after administration of the compound to be used in the present invention. In accordance with the present invention the compound may administered at least one hour prior to said personal contact. In one aspect of the present invention the compound is administered at least 2, 4, 6, 8, 10, 12, 14, 16, 18, 20, 22, 24, 26, 28, 30, or 32 hours prior to said personal contact. In this regard the longer time intervals are preferred over the shorter ones. In the context with the present invention the compound may be administered within 48 hours from influenza symptom onset, preferably within 24 hours from influenza symptom onset.

The present invention is not limited to any particular dosage of the compound of the present invention. The effective amount of the compound may be selected and/or adjusted by the attending physician according to his/her experience and applicable guidelines. However, the compound is preferably administered one time as single treatment. The compound can be administered to the patient at a suitable dose. The compound can be administered in a dose range varying depending on the patient's body weight, age, gender, health condition, diet, administration time, administration method, excretion rate and disease severity. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. However, the effective amount of the compound to be used in the present invention is preferably about 40 mg for patients <80 kg and about 80 mg for patients ≥80 kg. The dosing of baloxavir marboxil in pediatric patients may be as follows. In a patient that is younger than 1 year: (a) if the patient is younger than 4 weeks, then the effective amount may be about 1 mg/kg body weight; (b) if the patient is 4 weeks or older but younger than 3 months, then the effective amount may be about 1 mg/kg body weight; (c) if the patient is 3 months or older but younger than 12 months, then the effective amount may be about 2 mg/kg body weight. In a patient that is 1 year or older but younger than 12 years the dosing may be based on body weight. Two phase III clinical trials have been conducted in pediatric patients from 6 months to 12 years of age in Japan (studies 1618T0822 and 1705T0833). In the first study 1618T0822 a single tablet of baloxavir marboxil was administered to paediatric subjects aged 6 months to <12 years with influenza. Dosing of baloxavir marboxil was as follows: ≥40 kg: 40 mg dose, 20 kg-40 kg: 20 mg dose, 10 kg-20 kg: 10 mg dose, 5 kg-<10 kg: 5 mg. This dosage may also be used for paediatric index patients.

The invention is also not limited to any specific route of administration of the compound. All possible routes of administration that the attending physician deems useful or necessary are within the scope of the present invention. For example, the compound may be administered oral, rectal, nasal, topical, intradermal, as aerosol, vaginal, or parenteral, such as intramuscular, intravenous, subcutaneous, intraarterial, or intracardial. It is preferred that the compound is orally administered. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems. However, it is preferred that the compound to be used in the present invention is administered in the form of a tablet, more preferably a tablet for oral use. For example, the compound to be used in the present invention may be administered as 20 mg tablet and/or 40 mg tablet. The compound to be used in the present invention may also be administered in the form of granules. Granules are particularly advantageous if the compound is administered to persons who are not able to swallow tablets, e.g. children or persons having a nasogastric tube. Thus, a person having a body weight of <80 kg may receive two 20 mg tablets or one 40 mg tablet as single oral dose. A patient having a body weight of ≥80 kg may receive four 20 mg tablets or two 40 mg tablets as single oral dose.

The index patient may be any human subject having an influenza virus infection. It is preferred that the index patient is at least 2 years old. It is more preferred that the index patient is at least 12 years old. For example, the index patient may be a human patient which is preferably aged ≥12 to ≤64 years. The treated index patient is preferably healthy beside the influenza virus infection. As mentioned above, it is preferred that the treated index patient has at least one contact person (e.g. a household contact) which is not vaccinated against influenza. Even more preferably, the treated index patient has at least two contact persons (e.g. household contacts) which are not vaccinated against influenza. Said contact persons may be ≥2 years old.

The control patient is an influenza-infected patient who is as similar as possible to the index patient beside that control patient is not treated with the compound to be used in the present invention. Thus, the control patient has an identical or at least similar (i.e. comparable) age and health status as the index patient and the control patient and the index patient are infected with the same influenza virus strain.

Influenza viruses cause seasonal epidemics and, very occasionally, global pandemics. The word pandemic (from the Greek pan meaning all and demos meaning people) describes an epidemic that affects the whole population. The compound to be used in the present invention has the advantage that it reduces the transmission of an influenza virus, and therefore, can reduce the risk of a treated index patient to lead (or contribute) to the development of an influenza epidemic or influenza pandemic. Thus, in one aspect of the present invention the treatment (of the index patient) has the effect that the treated index patient has a reduced risk to trigger an influenza epidemic or an influenza pandemic as compared to a control patient. Thus, in accordance with the present invention the treated index patient has a reduced risk to trigger an influenza epidemic or an influenza pandemic as compared to a control patient.

Herein an "influenza pandemic" is a global epidemic caused by an influenza virus to which there is little or no pre-existing immunity in the human population. A pandemic is defined as an epidemic occurring worldwide, or over a very wide area such as over the whole country. A pandemic is often crossing international boundaries and is usually affecting a large number of people". A true influenza pandemic occurs when almost simultaneous transmission takes place, e.g. worldwide. Simultaneous worldwide transmission of influenza is sufficient to define an influenza pandemic and is consistent with the classical definition of "an epidemic occurring worldwide". For example, a pandemic may be caused by a newly developed Influenza virus, which is the result of changes within an existing influenza virus. Such changes are discussed below in more detail. Pandemics can be relatively mild or may cause severe disease or death. Severe disease may occur in certain risk groups, which may correspond to those at risk of severe disease due to seasonal influenza. However, healthy persons are also likely to experience more serious disease than that caused by seasonal influenza.

An "influenza epidemic" is a sudden increase in the number of cases of influenza virus infection above what is normally expected. An "influenza epidemic" is a widespread occurrence of influenza in a community at a particular time. An epidemic is an event in which a disease is actively spreading. In contrast, the term pandemic relates to geographic spread and is used to describe a disease that affects a whole country or the entire world.

There are three types of influenza viruses: A, B, and C. Types A and B cause widespread outbreaks of influenzal illness nearly every year. Influenza C is associated with sporadic, often asymptomatic infection with little or no mortality and therefore is not of public health concern. Pandemic influenza occurs only with influenza A viruses. However, influenza B viruses can cause an influenza epidemic. Indeed, influenza B is part of the seasonal flu epidemics. Thus, in accordance with the present invention the influenza virus may be an influenza A virus or an influenza B virus, preferably an influenza A virus. It is preferred that the influenza virus is an epidemic influenza virus strain or a pandemic influenza virus strain.

Pandemics and epidemics of influenza in humans arise as a result in changes in the surface glycoproteins known as 'antigenic shift' and 'antigenic drift'.

In particular, one way influenza viruses change is called "antigenic drift." An "antigenic drift" are small changes in the genes of influenza viruses that happen continually over time as the virus replicates. These small genetic changes usually produce viruses that are pretty closely related to one another, which can be illustrated by their location close together on a phylogenetic tree. Viruses that are closely related to each other usually share the same antigenic properties and an immune system exposed to a similar virus will usually recognize it and respond (this is sometimes called cross-protection). But these small genetic changes can accumulate over time and result in viruses that are antigenically different (i.e. further away on the phylogenetic tree). When this happens, the body's immune system may not recognize those viruses which may result in an influenza epidemic.

Another type of change of an influenza virus is called "antigenic shift." Pandemic influenza is the outcome of antigenic shift and occurs only with influenza A virus.

Antigenic shift is an abrupt major change in the influenza A virus, resulting in new hemagglutinin (HA) and/or new HA and neuraminidase (NA) proteins in the influenza virus. Thus, antigenic shift results in a new influenza A subtype or a virus with a hemagglutinin (HA) or a hemagglutinin (HA) and neuraminidase (NA) combination that has emerged from an animal population that is so different from the same subtype in humans that most people do not have immunity to the new virus. Such a "shift" occurred in the spring of 2009, when an H1N1 virus with a new combination of genes emerged to infect people and quickly spread, causing a pandemic. When shift happens, most people have little or no protection against the new virus. Thus, antigenic shift involves an abrupt change in the HA and possibly NA antigens, which are totally different from those circulating in humans for many years before. Antigenic shift results in an entirely novel virus that is serologically distinct from earlier viruses and could not have arisen from them by mutation. A pandemic is likely when large sections of the population around the world lack immunity to the new virus (i.e., have no or little antibody to the HA of the novel virus), and it is readily transmissible from person to person, causing serious disease. A pandemic is considered imminent when the new virus spreads rapidly beyond the community in which it was first identified. While influenza viruses are changing by antigenic drift all the time, antigenic shift happens only occasionally. Type A viruses undergo both kinds of changes; influenza type B viruses change only by the more gradual process of antigenic drift.

As mentioned above, Influenza pandemics are usually the result of antigenic "shift", and influenza epidemics are usually the result of antigenic "drift". Therefore, in the context of the present invention the influenza virus is antigenically different as compared to the parent influenza virus strain as a result of antigenic drift and/or antigenic shift, preferably antigenic shift or both.

A person skilled in the art can easily determine whether a given influenza virus is the result of antigenic drift or antigenic shift. As described above, antigenic shift is an abrupt, major change in the influenza A viruses, resulting in new hemagglutinin and neuraminidase proteins combinations in influenza A viruses that infect humans. Thus, in order to determine whether an influenza A virus which infects humans is the result of antigenic shift, the hemagglutinin (HA) and neuraminidase (NA) protein combination of said influenza A virus may be compared to the hemagglutinin (HA) and neuraminidase (NA) protein combinations of known influenza A viruses which infect humans. If the hemagglutinin (HA) and neuraminidase (NA) protein combination of the influenza A virus at issue is not present in the known human-infecting influenza A viruses, then the influenza A virus at issue is the result of antigenic shift.

Antigenic drift are point mutations within the genome of the virus. The skilled person can easily determine whether a given influenza virus is the result of antigenic drift by sequencing the genome of this influenza virus and comparing the resulting sequence to the viral genome sequences of known influenza viruses. Accordingly, in order to determine whether an influenza virus which infects humans is the result of antigenic drift, the viral genome sequence of said influenza virus may be compared to the viral genome sequence of known influenza viruses which infect humans. If the viral genome sequence of the influenza virus at issue comprises nucleotide changes (i.e. point mutations) as compared to the known human-infecting influenza viruses, then the influenza virus at issue is the result of antigenic drift.

Antigenic drift is the normal evolutionary process when virus genomes mutate (slowly compared to antigenit shift) due to error prone polymerases. These mutations can change functional features of the virus, e.g. resistance of enzymes against specific drugs. Therefore, in order to determine whether a virus is the result of antigenic drift, the functional features of the virus may be determined.

Beside antigenic shift viruses with pandemic potential can also emerge through virus re-cycling. More specifically, examining blood samples from people of varying ages, it can be shown whether a particular subtype of influenza circulated previously and, if so, approximately when it ceased to circulate. This analysis, termed seroarchaeology, supports the theory of virus recycling. Seroarchaeology has established beyond reasonable doubt that H2 and H3 subtypes recycled in human beings during the 19th and 20th centuries. In addition, the H1 subtype, which circulated in mankind during the period 1918 to 1957, re-emerged or 'recycled' in 1978. *Analysis of the RNAs of viruses isolated during the 1977-78 epidemic showed that the virus was more closely related to viruses isolated in 1950 than to strains isolated after that time. Because of antigenic drift, it was speculated that the H1N1 virus must have re-emerged from the frozen state in nature or elsewhere. However, there is evidence that influenza viruses can remain invariant for prolonged periods in swine, which may serve as a reservoir for human infection. Thus, in the context of the present invention the influenza strain may be a recycling virus which had caused an epidemic or pandemic in the past. For example, virus strains which may recycle are A/Hong Kong/97 (H5N1), A/New Jersey/8/76 (H1N1), A/USSR/90/77 (H1N1), A/Hong Kong/68 (H3N2), A/Hong Kong/68 (H3N2), A/Hong Kong/68 (H3N2), A/Hong Kong/68 (H3N2), A/USSR/77 (H1N1), A/USSR/77 (H1N1), or A/USSR/77 (H1N1).

As mentioned above, in accordance with the present invention the influenza virus may be an influenza A virus or an influenza B virus (e.g. B/Minnesota/23/2015). The appended Examples surprisingly show that the compound to be used in the present invention can reduce the transmission of the influenza virus strains influenza A/Perth/265/2009 (H1N1pdm09) and A/England/195/2009. Thus, in accordance with the present invention the influenza virus strain is preferably an influenza A virus, more preferably an influenza A strain from the H1N1 subtype (e.g. A/Perth/265/2009 (H1N1pdm09) or A/England/195/2009). However, the influenza A virus may also be of the H2N2, H3N2, H5N1 or H7N9 subtype.

In a preferred aspect of the present invention the influenza virus strain does not carry an I38X mutation including a I38T mutation. Thus, it is preferred that the influenza virus stain does not carry an I38T mutation. The I38T substitution is a mutation within the viral acidic polymerase (PA) protein of some mutated influenza A strains. The sequence of the PA protein of an influenza A virus having the I38T mutation is shown in SEQ ID NO:4. Thus, in a preferred aspect of the present invention the influenza virus strain does not comprise a PA protein having the sequence of SEQ ID NO:4. It is also preferred that the influenza virus strain does not comprise a PA protein having a sequence which has at least 80%, preferably at least 90%, more preferably at least 95%, at least 96%, at least 97%, at least 98%, or at least 99% sequence identity to the sequence of SEQ ID NO:4 and comprising a T at the position corresponding to position 38 of SEQ ID NO:4. A fraction of the PA protein of an influenza A virus comprising the I38T mutation is shown in SEQ ID NO:5. Thus, in a preferred aspect of the present invention the influenza virus strain does not comprise a PA protein comprising the sequence as shown in SEQ ID NO:5.

As mentioned above, the compound to be used in the present invention can be used to prevent an influenza epidemic or an influenza pandemic. Thus, the invention relates to a method for preventing an influenza epidemic or an influenza pandemic, wherein the method comprises administering an effective amount of a compound to patients having an influenza virus infection (index patients), wherein the compound is administered to at least 10% of all influenza infected persons of a city's or country's population, and wherein the compound has one of the following formulae I and II:

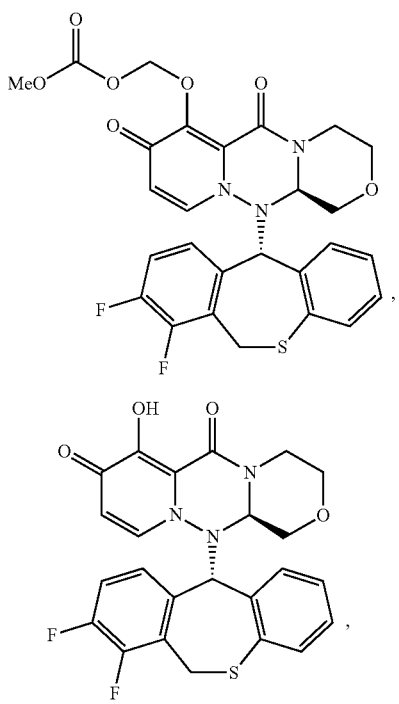

or its pharmaceutically acceptable salt.

Thus, the present invention relates to a compound for use in treating patients having an influenza virus infection (index patients), wherein the compound is to be administered to at least 10% of all influenza infected persons of a city's or country's population, wherein the compound prevents an influenza epidemic or an influenza pandemic, and wherein the compound has one of the following formulae I and II:

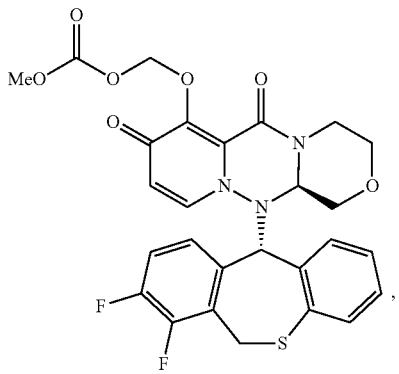

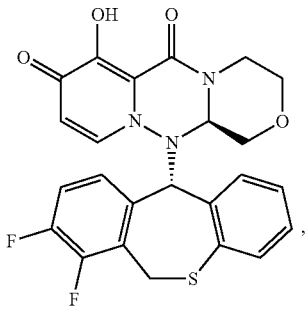

or its pharmaceutically acceptable salt.

Herein "prevent" an influenza epidemic or an influenza pandemic also means to reduce an outbreak of an influenza epidemic or of an influenza pandemic, e.g. to reduce the consequences of an outbreak of an influenza epidemic or an influenza pandemic.

The appended Examples provide a simulation which demonstrates that treating 15% or 30% of the population with baloxavir marboxil would prevent an influenza epidemic or pandemic, respectively. It is also demonstrated in the appended Examples that the compound to be used in the present invention has the advantageous effect that it reduces transmission, and therefore reduces the probability that an epidemic or pandemic arises. Thus, the means and methods provided herein advantageously reduce the economic implications which are associated with influenza infections.

As described above, conditions surrounding the 1997 Hong Kong outbreak of the pandemic "chicken influenza" highlight the need for advance planning to ensure an adequate response to a health emergency that is certain to be unpredictable, complex, rapidly evolving and accompanied by considerable public alarm. Once a pandemic begins it was in the past too late to accomplish the many key activities required to minimize the impact. Therefore, planning and implementation of preparatory activities must start well in advance. Accordingly, in order to prevent an influenza pandemic it is necessary to treat infected patients with the compound to be used in the present invention at an early stage. Thus, in accordance with the present invention it is envisaged that even an influenza epidemic is prevented by treating several (e.g. at least 10% of the) influenza infected persons during a seasonal flu. In one aspect of the present invention the above described method (i.e. the method for preventing an influenza epidemic or an influenza pandemic) is for preventing an influenza epidemic and at least 10%, preferably at least 15%, more preferably at least 20% of all influenza infected persons of a city's or a country's population (preferably a city's population) are treated with the compound. In line with this, in one aspect of the present invention the above described compound (i.e. the compound which prevents an influenza epidemic or an influenza pandemic) prevents an influenza epidemic and at least 10%, preferably at least 15%, and more preferably at least 20% of all influenza infected persons of a city's or a country's population (preferably a city's population) is to be treated with the compound. For example, the compound to be used in the present invention may be used to prevent an influenza epidemic (e.g. during a seasonal flu) if at least 20% of the population have an effective vaccination and if the amount of susceptible persons is not more than 30% of the population Of course the effect of the compound to be used in the present invention to prevent an epidemic (e.g. during a seasonal flu) or a pandemic increases with the percentage of influenza infected persons who are treated with the compound. Therefore, in order to prevent an influenza epidemic (e.g. during a seasonal flu) at least 30%, at least 40% or at least 50% of the infected persons of a city's or a country's population (preferably a city's population) may be treated with the compound.

In one aspect of the invention, the above described method (i.e. the method for preventing an influenza epidemic or an influenza pandemic) is for preventing an influenza pandemic and at least 25%, preferably at least 30%, and more preferably at least 35% of all influenza infected persons of a country's population is treated with the compound. In line with this, in one aspect of the invention, the above described compound (i.e. the compound which prevents an influenza epidemic or an influenza pandemic) is for preventing an influenza pandemic and at least 25%, preferably at least 30%, and more preferably at least 35% of all influenza infected persons of a country's population is to be treated with the compound For example, the compound to be used in the present invention may be used to prevent an influenza pandemic if there is no effective vaccination available and if the amount of susceptible persons is not more than 30% of the population. As mentioned above, the effect of the compound to be used in the present invention to prevent a pandemic increases with the percentage of influenza infected persons who are treated with the compound. Therefore, in order to prevent an influenza pandemic at least 45%, at least 55% or at least 65% of the infected persons of a city's or a country's population may be treated with the compound.

The means and methods provided herein are particularly advantageous if the influenza virus strain does not have a resistance against the compound to be used in the present invention. However, the influenza virus strain may have a resistance against other anti-viral drugs (such as peramivir, laninamivir, oseltamivir, zanamivir, rimantadine, umifenovir or amantadine). Tests for determining whether a given virus has a resistance against one or more drugs are commonly known in the art and comprise, e.g., the phenotypic resistance assay and the NA-Star assay, which are both described below.

The phenotypic resistance assay may be performed as described in the following: Phenotypic resistance assays (spot/focus reduction assay) can be performed by using the sensitive Virospot detection technology which combines classic virus culture in multi-well microtiter plates and virus-specific immunostaining with automated imaging, detection of infected cells using a CTL Immunospot UV analyzer equipped with Biospot analysis software. The Virospot technology platform determines sensitivity of virus isolates to antiviral drugs measuring $IC_{50}/IC_{90}$. In brief, the method is based on inoculation of infectious virus on MDCK cell monolayers in 96-well plates in the presence of a drug concentration range. After incubation the cells are fixed and immunostained with virus-specific antibodies followed with TrueBlue substrate and image capture using the UV Analyzer.

The NA-Star assay is particularly useful for determining phenotypic resistance to neuraminidase inhibitors (such as, e.g. oseltamivir), and can be performed as follows: This assay uses a chemiluminescent substrate for highly sensitive detection of neuraminidase enzyme activity. Neuraminidase activity yields a luminescent compound which is quantified by using a reader. Virus neuraminidase activity is determined in the presence of serial dilutions of the neuraminidase inhibitor. Sensitivity to neuraminidase inhibitor is expressed as $IC_{50}/IC_{90}$ values.

The compound to be used in accordance with the present invention may be combined with other anti-influenza drugs. Four antiviral drugs are currently approved in the EU for the prevention and treatment of influenza: the M2 ion-channel inhibitor amantadine and the NAIs oseltamivir phosphate, zanamivir and peramivir. A second M2 inhibitor, rimantadine, holds marketing authorisations in the Czech Republic, France and Poland but is not marketed in these countries. Therefore, the compound to be used in the present invention may be administered as co-therapy with amantadine, oseltamivir phosphate, zanamivir, peramivir, and/or rimantadine. Neuraminidase inhibitors (NAIs) are the mainstay of treatment for influenza infections. Therefore, if the compound to be used in the present invention is administered as co-therapy, then it is preferably combined with oseltamivir phosphate or zanamivir. Both oseltamivir phosphate and zanamivir are administered twice daily for 5 days.

As described above, the present invention provides means and method for reducing the transmission of an influenza virus, i.e. for reducing the infectiousness of an influenza-infected patient (i.e. the index patient). In line with this, the invention also relates to the following aspects. All explanations, definitions and preferred aspects which are explained above also relate, mutatis mutandis, to the inventive aspects described below.

The invention also relates to a method for treating an influenza virus infection, wherein said method comprises administering an effective amount of a compound to a patient having an influenza virus infection (index patient), wherein the compound has one of the formulae (I) and (II) or its pharmaceutically acceptable salt, and wherein the compound reduces transmission. Also encompassed by the present invention is a method for treating influenza, comprising: reading a dosage instruction on a package insert or in a package for a pharmaceutical formulation comprising a compound having one of the formulae (I) and (II)) or being a pharmaceutically salt thereof; and administering an effective amount of the compound to an influenza-infected patient (index patient) whose infectiousness is to be reduced. The invention also relates the use of a compound which has one of the formulae (I) and (II), or its pharmaceutically acceptable salt, for the preparation of a medicament for treating an influenza-infected patient (index patient) whose infectiousness is to be reduced. Also provided by the present invention is a package comprising a pharmaceutical formulation comprising a compound which has one of the formulae (I) and (II), or its a pharmaceutically salt, and further comprising a dosage instruction for administering an effective amount of the compound to an influenza-infected patient (index patient) whose infectiousness is to be reduced.

As explained above, the index patient is preferably healthy beside the influenza virus infection. It is preferred that the index patient is not treated with any medicament beside the compound to be used in the present invention. For example, it is preferred that the index patient is not treated with an investigational therapy, a systemic antiviral drug (e.g. peramivir, laninamivir, oseltamivir, zanamivir, rimantadine, umifenovir or amantadine), immunosuppressants, corticosteroids, antifungal drugs, or a drug which is administered to the eyes, nose or ears, or by inhalation.

The meaning of the term "influenza virus infection" or variations thereof is commonly known in the art and refers to a disease which is caused by the influenza virus. More specifically, an influenza virus infection is an acute respiratory infectious disease caused by a virus of the orthomyxovirus family. Two forms are known to principally infect humans and to cause disease in humans, the influenza A virus and the influenza B virus. The influenza viruses have a segmented, negative-sense, single-stranded, lipid encapsulated ribonucleic acid (RNA) genome; they range between 80 and 100 nm in size. Subtypes are defined according to haemagglutinin (HA) and neuraminidase (NA) glycoproteins present in the viral lipid coat. Influenza viruses enter the respiratory epithelial cell by attachment of the viral HA to sialic acid-containing receptors on the cell membrane, followed by internalisation of the virus into an acidic endosome. In the acidic environment of the endosome, the HA undergoes a conformational change that liberates a fusion peptide and results in fusion of the viral envelope with the endosomal membrane. At the same time the matrix-2 (M2) protein acts as an ion channel allowing hydrogen ions to enter the virion from the endosome. This allows the viral gene segments to leave the virion and enter the cytoplasm, a process known as uncoating. Viral gene segments are transported to the nucleus where the viral polymerase complex, composed of the proteins polymerase basic protein 1 (PB1), polymerase basic protein 2 (PB2), and polymerase acidic protein (PA), directs the synthesis of the plus-sense messenger RNA (mRNA) as well as, via a plus-sense full length complementary RNA, synthesis of negative-sense full length copies that will serve as progeny genomic RNA. The polymerase proteins also play a role in disruption of host cell protein synthesis. Assembly of progeny virions occurs at the plasma membrane, and the viral NA protein plays a role in release of virus from the cell surface by cleavage of surface sialic acid.

The "compound" to be used in the present invention is a compound which has one of the following formulae I and II:

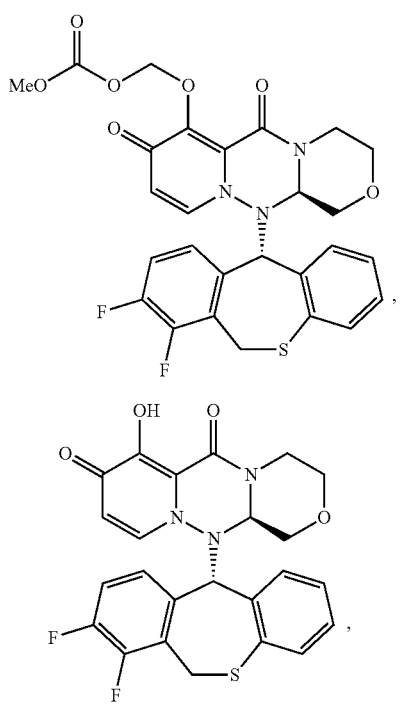

or its pharmaceutically acceptable salt (i.e. of the compound having a formula of (I) or (II)). The compound to be used in the present invention is also referred to herein as "compound", "compound for use", "compound to be used (herein/in the present invention)" or "compound of the present invention".

The compound to be used in the present invention acts as a selective cap-dependent endonuclease (CEN) inhibitor, inhibiting the 'cap-snatching' function of the PA subunit of the influenza polymerase, which is used to cleave 5' cap structures from host cell mRNAs, which are used as primers for viral mRNA transcription. By inhibiting this essential function, the compound as used herein suppresses the replication of influenza viruses.

The compound to be used in the present invention has a broad spectrum of activity against seasonal (e.g. A/H1N1, A/H3N2, and B) and highly pathogenic avian (e.g. A/H5N1, A/H7N9) influenza viruses, with more potent antiviral activity (lower half maximal inhibitory concentration [$IC_{50}$]) compared with other common anti-influenza drugs such as oseltamivir, zanamivir, or peramivir. The compound's ability to be efficacious as a single dose administration simplifies treatment and improves patient compliance compared to neuraminidase inhibitors (NAIs). Preferably, the compound has the formula of (I) or (II), most preferably of (I). The compound of formula (I) can also be displayed as follows:

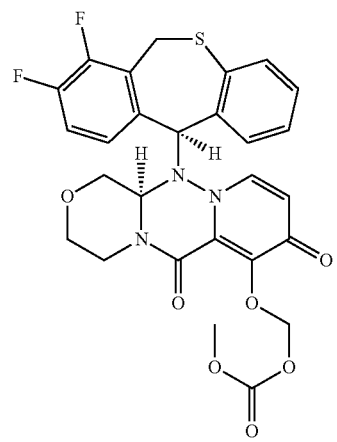

Baloxavir marboxil (BXM)

This compound (i.e. the compound of formula (I)) has a molecular formula of $C27H23F2N3O7S$. This compound is a pro-drug which is known as baloxavir marboxil. Baloxavir marboxil is known in the art and described, e.g., in Noshi, *Antiviral research* 160 (2018): 109-117.

Baloxavir marboxil (i.e. the compound of formula (I)) is an anti-influenza virus drug with a novel mechanism of action. It was discovered and is being developed by Shionogi & Co., Ltd. and F. Hoffman-La Roche, Ltd. Baloxavir marboxil (S-033188) is a pro-drug and is converted to an active form (S-033447) through metabolism (hydrolysis). The active form is shown herein as formula (II). The active form (S-033447) selectively inhibits cap-dependent endonuclease (CEN) activity necessary for replication of influenza viruses (Omoto, *Sci Rep.* 2018; 8(1): 9633). A broad spectrum of activity against seasonal influenza viruses and on alleviating effects of influenza symptoms were shown in nonclinical efficacy studies and clinical studies in patients with influenza, including the Phase 2 proof of concept and dose-finding study, the Phase 3 double-blind study in otherwise healthy patients (Portsmouth S, Kawaguchi K, Arai M, Tsuchiya K, Uehara T. Cap-dependent endonuclease inhibitor S-033188 for the treatment of influenza: results from a phase 3, randomized, double-blind, placebo- and active-controlled study in otherwise healthy adolescents and adults with seasonal influenza. Abstract LB-2. Oral presentation at ID Week 2017, October 4-8 2017, San Diego, CA, USA.), and the Phase 3 open-label study in otherwise healthy pediatric patients.

The compound as shown in formula (II) is the active form of baloxavir marboxil (i.e. of the pro-drug of formula (I)). The compound of formula (I) can also be displayed as follows:

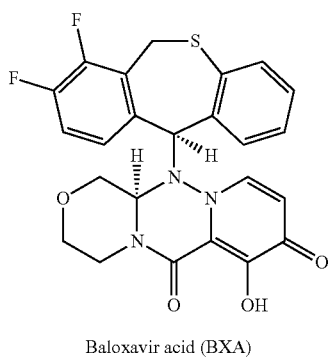 [SMILES: O=C1c2c(O)c(=O)ccn2N([C@@H]2c3ccccc3SCc3c2ccc(F)c3F)[C@@H]2COCCN12]

Baloxavir acid (BXA)

The compound of formula (II) is also known as baloxavir acid. Baloxavir acid is known in the art and described, e.g., in Noshi, *Antiviral research* 160 (2018): 109-117.

The pharmaceutically acceptable salts of the compounds used in the present invention include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with sodium, potassium, calcium, magnesium, iron and the like are included. These salts can be formed by the usual methods.

The production of the compound of the present invention is well known in the art. For example, the compound of the present invention can be prepared with the methods described in the patent application PCT/JP2016/063139, which is published as WO 2016/175224A1.

As mentioned above, in accordance with the present invention, it is preferred that the influenza virus strain does not comprise a PA protein having a sequence which has at least 80%, preferably at least 90%, more preferably at least 95%, at least 96%, at least 97%, at least 98%, or at least 99% sequence identity to the sequence of SEQ ID NO:4 and comprising a T at the position corresponding to position 38 of SEQ ID NO:4. In particular, FASTA sequences of two sequences of viral PA proteins can be generated and aligned in order to evaluate the degree of identity between the two viral PA proteins. To determine the percent identity of two sequences, the sequences are aligned for optimal comparison purposes (e.g., gaps can be introduced in one or both of a first and a second amino acid sequence for optimal alignment and non-homologous sequences can be disregarded for comparison purposes). The percent identity between the two sequences is a function of the number of identical positions shared by the sequences, taking into account the number of gaps, and the length of each gap, which need to be introduced for optimal alignment of the two sequences. Percent identity between two polypeptides/amino acid sequences is determined in various ways which are known by the skilled person, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482 489 (1981)) as incorporated into GeneMatcher Plus™, Schwarz and Dayhof (1979), Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. Preferably, the viral PA protein sequences are compared over their entire lengths. For purposes of the present invention, the comparison of sequences and determination of percent identity between two sequences can be accomplished using a Blossum 62 scoring matrix (with a gap penalty of 12, a gap extend penalty of 4, and a frameshift gap penalty of 5).

As mentioned above, one aspect of the present invention relates to a pharmaceutical composition comprising a compound which has one of the formulae (I) and (II), or its pharmaceutically acceptable salt, and optionally comprising a pharmaceutically acceptable carrier, wherein the pharmaceutical composition prevents (e.g. reduces) transmission of the influenza virus. The pharmaceutical compositions can be formulated with a pharmaceutically acceptable carrier by known methods. For example, the compositions can be formulated by appropriately combining the ingredients with a pharmaceutically acceptable carrier or a medium, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such. The content of the active ingredient in such a formulation is adjusted so that an appropriate dose within the required range can be obtained.

The pharmaceutical composition may optionally comprise one or more pharmaceutically acceptable excipients, such as carriers, diluents, fillers, disintegrants, lubricating agents, binders, colorants, pigments, stabilizers, preservatives, antioxidants, or solubility enhancers. Also, the pharmaceutical compositions may comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions are not limited to the means and methods described herein. The skilled person can use his/her knowledge available in the art in order to construct a suitable composition. Specifically, the pharmaceutical compositions can be formulated by techniques known to the person skilled in the art such as the techniques published in *Remington's Pharmaceutical Sciences,* 20th Edition.

The content of all documents cited herein above and below is incorporated by reference in its entirety.

The Examples illustrate the invention.

Example 1: Baloxavir Marboxil Prevents Respiratory Droplet Transmission

Study Design

The study design of this experiment is shown in FIG. 1. In this experiment baloxavir was administered once to ferrets as s.c. suspension with 1 mg/kg at 4 different locations in the back. Oseltamivir phosphate (5 mg/kg) was orally administered twice daily for 5 days.

The experiment is designed with 3 arms, baloxavir, oseltamivir and no drug. For each arm there were 4 groups of animals. In each group there were donor animals and sentinel animals who are exposed to infected donors either by a direct contact or a respiratory droplet route.

The experiment was performed as follows:

Day 0:

All animals were implanted with a temperature monitoring and identity chip. Four ferrets (donors) were infected with influenza A virus. Wild type (RG) A/England/195/2009 at a dose of $10^4$ pfu was given intranasally under light anaesthetic (ketamine/xyalzine) in a total volume of 200 microlitres.

Day 1:

24 hours post infection, the 4 infected ferrets were nasal washed. Nasal washes were assayed immediately by plaquing on fresh MDCK cells for infectious virus and carrying out RT-PCR for viral RNA load. Each donor ferret was then treated with either baloxavir, oseltamivir phosphate or vehicle only. Baloxavir was administered once subcutaneously in 4 locations on the back with 1 mg/l mL/kg per injection (total 4 mg/4 mL/kg). After dosing of baloxavir blood samples (minimum 200 μl) were collected from the donor animals at 48 h and 144 h, respectively, for pharmacokinetics (PK) analysis.

A 5 mg/kg dose of oseltamivir phosphate was orally administered twice daily for 5 days, which is considered to be equivalent to the standard human adult dose of 75 mg for treatment (*J Antimicrob Chemother* 2014; 69: 2458-2469). After drug administration on day 1 one sentinel animal was introduced into same cage as each infected donor (DC animal) and one sentinel animal was introduced into adjacent cage (RD animal). Sentinel animals were not treated with any drug.

Day 2:

All ferrets were nasal washed on day 2 and every subsequent day until experiment end starting with RD animals, then DC animals, and finishing with donors. Plaque assay was performed immediately on nasal wash. Virus RNA was also monitored by RT-PCR. Daily observation of clinical signs including temperature, weight loss and respiratory signs was performed. In addition, virus exhaled in breath from the 4 donor animals was monitored by placing them in a chamber for 10 minutes and sampling air using sentinel MDCK cells.

Day 4:

In the morning, the 4 DC and 4 RD animals were removed and housed separately. Thus, the sentinels had been exposed from day 1-4 post infection of donor (72 hours).

The experiment was finished when all animals had two consecutive days of virus negative nasal wash.

Materials and Methods

Animal Studies

Female ferrets (20-24 weeks old) weighing 750-1000 g were used. After acclimatization, sera were obtained and tested by HAI for antibodies against A/England/195/09, pandemic H1N1. All ferrets were negative for influenza antibodies at the start of the experiments. Body weight was measured daily. Strict procedures were followed to prevent aberrant cross-contamination between animals. Sentinel animals were handled before inoculated animals, and work surfaces and handlers' gloves were decontaminated between animals. For inoculation, ferrets were lightly anaesthetized with ketamine (22 mg $kg^{-1}$) and xylazine (0.9 mg $kg^{-1}$) and inoculated intranasally with virus diluted in PBS (0.1 ml per nostril). All animals were nasal washed daily, while conscious, by instilling 2 ml PBS into the nostrils, and the expectorate was collected in modified 250 ml centrifuge tubes. The nasal wash expectorate was used for virus titration by plaque assay. The limit of virus detection in the plaque assays was 10 p.f.u. $ml^{-1}$.

Ferret Monitoring and Activity Measurement

Ferrets were weighed daily post infection. Body temperature was measured daily via subcutaneous IPTT-300 transponder (Plexx B.V, Netherlands). Ferret activity was scored manually at the same time every day. This scoring was based on a previous publication Oh D Y, Barr I G, Hurt A C (2015) PLoS ONE 10(3): e0118780. Ferrets were observed whilst in their cages, at least 4 hours post nasal washing in order to minimize disruption to their activity.

Cells

MDCK cells were maintained in Dulbecco's modified Eagle's medium (DMEM; Gibco, Invitrogen) supplemented with 10% FBS and 1% penicillin/streptomycin (Sigma-Aldrich).

Plaque Assay

Plaque assays were performed using MDCK cells. Cell layers inoculated with 100 μl serially diluted samples were overlaid with 0.6% agarose (Oxoid) in supplemented DMEM with 2 μg trypsin (Worthington) $ml^{-1}$ and incubated at 37° C. for 3 days.

Sample Preparation for Real-Time PCR

140 μl of ferret nasal wash was used to extract RNA using the Qiagen Viral RNA mini kit (Cat No./ID: 52904), according to manufacturer's instructions.

Real-Time PCR

Real-time PCR was performed using 7500 Real Time PCR system (ABI) in 20 µl reactions using AgPath-ID™ One-Step RT-PCR Reagents 10 µl RT-PCR buffer (2×) (Thermo Fisher, Cat. No. 4387391), 4 µl of RNA, 0.8 µl forward (5'GACCRATCCTGTCACCTCTGA 3', SEQ ID NO:1) and reverse primers (5' AGGGCAT-TYTGGACAAAKCGTCTA3', SEQ ID NO:2) and 0.4 µl probe (5' FAM-TCGAGTCCTCGCTCACTGGGCACG-BHQ1 3', SEQ ID NO:3). Reverse transcription was carried out at 45° C. for 10 min. PCR amplification conditions consisted of 95° C. for 15 s and 60° C. for 1 min after an initial denaturation step at 95° C. for 10 min. In total 40 cycles were performed. For each sample, the Ct value for the target M gene was determined. M gene is an influenza gene encoding the 2 Matrix proteins M1 and M2. The M gene is detected in PCR and can be used to quantify the influenza virus. Based on the standard curves, absolute copy numbers were calculated to establish if the ferret was positive for influenza A.

Ethics Statement

All work performed was approved by the local genetic manipulation (GM) safety committee of Imperial College London, St. Mary's Campus (center number GM77), and the Health and Safety Executive of the United Kingdom. All animal research described in this study was carried out under a United Kingdom Home Office License, P48DAD9B4.

All above described methods are commonly known in the art, and described, e.g., in the document "*Contact transmission of influenza virus between ferrets imposes a looser bottleneck than respiratory droplet transmission allowing propagation of antiviral resistance.*" Frise R, Bradley K, van Doremalen N, Galiano M, Elderfield R A, Stilwell P, Ashcroft J W, Fernandez-Alonso M, Miah S, Lackenby A, Roberts K L, Donnelly C A, Barclay W S. *Sci Rep.* 2016 Jul. 19; 6:29793. doi: 10.1038/5rep29793.PMID:27430528.

Results and Discussion

The results of Example 1 are shown in FIGS. 2A-2L and 3A-3M. These results show that respiratory droplet transmission occurred less frequently in baloxavir-treated subjects as compared to oseltamivir- or placebo-treated subjects (i.e. 25% transmission vs. 100% transmission).

In addition, a delay in time to shedding was observed for sentinel animals exposed to donors treated with either oseltamivir of baloxavir compared to control. The mean time to virus shedding was 4.25 days, vs 5.5 days for direct contact sentinels exposed to donors treated with either oseltamivir or Baloxavir. For respiratory droplet exposed sentinels, the mean time to virus shedding was 4.5 days from untreated donor animals vs 9.3 days for oseltamivir treated animals and 8 days from the one baloxavir treated sentinel who acquired infection by the RD route.

Taken together this shows that baloxavir treatment of donor ferrets infected with a pH1N1 2009 virus delayed transmission to cohoused sentinel ferrets and decreased the likelihood of transmission by the respiratory droplet route.

Example 2: Baloxavir Marboxil Prevents Direct Contact Transmission

Materials and Methods

Antivirals and Drug Administration

The active form baloxavir acid (S-033447, hereafter BXA) and pro-drug oseltamivir phosphate (hereafter OST) was kindly provided by Shionogi & Co., Ltd., Japan. The vehicle for BXA delivery was methyl cellulose (Sigma-Aldrich, Australia) in 0.5 w/v % aqueous solution prepared with sterile water (hereafter MC solution). BXA in suspension with MC solution (1 mg/mL) was prepared using an agate mortar and pestle, and was delivered to reversibly anaesthetised animals in a single treatment consisting of 4 subcutaneous injections at 4 locations on the dorsal region (total dose 4 mg/kg per animal). Animals in the placebo group were dosed identically using MC solution (1 mL/kg) alone. OST doses (10 mg/mL) were prepared in sugar solution (1 g/mL) and delivered bis in die (8 hr interval) to non-sedated ferrets by the oral route (total dose 10 mg/kg/day).

Cells and Virus

Madin-Darby Canine Kidney (MDCK) cells were maintained in Dulbeco's modified Eagle's medium (DMEM, Gibco) supplemented with 10% (v/v) foetal bovine serum, 2 mM GlutaMAX, 0.05% sodium bicarbonate, 100 μM MEM non-essential amino acid, 20 mM HEPES and 50,000 U penicillin-streptomycin (full mixture termed 'growth media').

Influenza A/Perth/265/2009 H1N1pdm09 virus was used for animal inoculation. This virus was isolated from a clinical specimen (Lab #910894) at the World Health Organisation Collaborating Centre for Reference and Research on Influenza (WHOCCRRI, Melbourne, Australia). Viruses were plaque purified and propagated in MDCK cells.

Animals

Outbred male and ferrets (*Mustela purtorius furo*)>12 weeks old and weighing between 600-1800 g were obtained from independent breeders, and confirmed to be seronegative against recently circulating influenza antigens (A/Michigan/45/2015, A/Singapore/INFIMH-16-0019/2016, B/Phuket/3073/2013, B/Brisbane/60/2008) by haemagglutination-inhibition (HI) assay. Identification/temperature monitoring chips (LifeChip, Bio-Thermo) were implanted subcutaneously on the dorsal region of each ferret. Animals were monitored at least once daily for temperature and weight changes, had ad libitum access to pellet feed (Eukanuba) and water, and were provided with supplementary wet food (Hill's Pet Nutrition, Australia) as ethically required (below 90% baseline weight). Routine sample collection was performed under sedation using intramuscular injection of xylazine (5 mg/kg) (Troy Laboratories), whereas virus inoculation and subcutaneous drug delivery was performed under reversible anaesthesia by intramuscular injection of ketamine (10 mg/kg) (Troy Laboratories) in combination with midazolam (0.5 mg/kg) (Troy Laboratories) and medetomidine (0.02 mg/kg) (Troy Laboratories), which was antagonised by atipamezole (0.01 mg/kg) (Troy Laboratories). Ferrets at endpoint were injected i.m. with a non-reversible anaesthetic consisting of ketamine (up to 25 mg/kg) and xylazine (up to 5 mg/kg), before sacrifice by sodium pentobarbitone (Troy Laboratories) overdose (up to 1,000 mg/kg) by intracardiac injection.

Ferret studies were performed in the Bio-Resources Facility (Physical Containment Level 2) at the Peter Doherty Institute (Melbourne, Australia), according to the Australian Government, National Health and Medical Research Council Australian code of practice for the care and use of animals for scientific purposes (8th Edition). Study procedures were approved (AEC #1714278) by the Biochemistry & Molecular Biology, Dental Science, Medicine, Microbiology & Immunology, and Surgery Animal Ethics Committee of The University of Melbourne.

Virology

Nasal wash samples were stored with 1% w/v bovine serum albumin (BSA) at −80° C. before determination of viral titre by $TCID_{50}$ assay. In brief, samples were serially diluted 10-fold in serum-free growth media containing TPCK-treated trypsin (4 µg/mL; Sigma-Aldrich) and added in triplicate to flat-bottom 96-well plates containing a confluent monolayer of MDCK cells in each well. Following infection, cells were maintained in serum-free growth media (containing 4 µg/mL TPCK-treated trypsin) for 96 h at 37° C., 5% CO2, before assessment of viral growth by haemagglutination assay using 1% turkey red blood cells (RBCs). $TCID_{50}$ titres were calculated by the Reed and Muench (1938) method (Reed, L. J., and Muench, H. (1938), *American Journal of Epidemiology* 27, 493-497).

Quantitative Real-Time RT-PCR

Viral RNA was extracted from 200 µL nasal wash samples using the NucleoMag VET isolation kit (Macherey Nagel) on the KingFisher Flex (ThermoFisher Scientific) platform according to manufacturer's instructions. Influenza virus M gene copy number in 4 µL RNA was determined by quantitative real-time RT-PCR performed using the SensiFAST Probe Lo-ROX One-Step qRT-PCR System Kit (Bioline) on the ABI 7500 Real Time PCR System (Applied Biosystems) under the following cycling conditions: 45° C. for 10 min, 1 cycle; 95° C. for 2 min, 1 cycle; 95° C. for 5 sec then 60° C. for 30 sec, 40 cycles. Sample RNA was quantitated using influenza A RNA standards of known copy number, kindly provided by Seqirus, Australia. Universal influenza A real-time primer/probe sets were kindly provided by CDC Influenza Branch (Atlanta, USA) (sequences available upon request). Results were analysed by 7500 Fast System SDS software v1.5.1.

Serology

Sera were collected from endpoint recipient blood samples by centrifugation, and non-specific inhibitors of agglutination were removed by treatment with receptor-destroying enzyme (RDE) (Denka Seiken) according to manufacturer's instructions. Treated sera were adsorbed with turkey RBCs prior to HI assay to remove non-specific agglutination factors. Briefly, sera (initially 1:20 dilution) were serially diluted twofold in PBS in V-bottom 96-well plates (final row left as PBS negative control). A/Perth/265/2009 virus adjusted to 4 haemagglutination units in 25 µL was mixed to all sample wells for 1 hr incubation at room temperature, followed by 45 min incubation of 1% turkey RBC. Positive inhibition was defined as the appearance of a running 'teardrop' pattern comparable to the PBS negative control. HI titre was calculated as the reciprocal of the highest serum dilution at which agglutination was inhibited.

Antiviral Pharmacokinetic Analysis

Endpoint BXA and placebo-treated donor blood samples were collected in heparinised tubes, and plasma isolated by centrifugation. Plasma samples were stored at −80° C. until transport to analytical facilities at Shionogi & Co., Ltd.

Statistical Analyses

Data analysis was performed using Graphpad Prism (GraphPad Software, v5.01). Nasal wash viral titres of all ferrets on each day post inoculation/exposure were compared by a matched two-way analysis of variance (ANOVA) followed by Tukey's multiple comparisons test. Quantitative real time RT-PCR was performed on influenza control RNA of known copy number to generate a standard curve (linear regression of influenza cycle threshold (Ct) values vs. copy number). Viral copy numbers present in nasal wash RNA samples on the same assay were calculated using the formula of the standard curve. Influenza A copy numbers for each group of ferrets were compared by a matched two-way ANOVA followed by Tukey's multiple comparisons test. $p<0.05$ was considered statistically significant.

Study Design

The time course of Experiments 1-3 is shown in FIGS. 4, 8 and 11.

Experimental Groups and Treatment Schedules

This study consisted of three separate Experiments using different schedules of antiviral treatment and timing of naïve animal co-housing. In each experiment, twenty-four ferrets were randomly assigned to three groups (n=8): BXA, OST and placebo. Within each group, n=4 ferrets were designated as treated donor ferrets, and n=4 as naïve recipients. On 0 DPI (days post inoculation) for each experiment, all donor ferrets (each individually housed) were intranasally inoculated with influenza A/Perth/265/2009 at $10^3$ 50% tissue culture infective doses ($TCID_{50}$) in 40 µL of phosphate-buffered saline (PBS). As described above, donors in the BXA and placebo groups received a single antiviral treatment, whereas OST-group donors were treated daily until endpoint (excluding cull day). At the designated time point, naïve recipient ferrets were co-housed with treated donor ferrets (1:1 per cage) for a contact exposure period of 48 hr.

Experiment 1: Antiviral treatment for all donors commenced at 1 DPI, and naïve recipient ferrets were co-housed immediately following treatment. Body weight and temperature were monitored daily from all animals. Daily nasal wash samples were collected 1 mL of PBS from 1 DPI to 3 DPI for donor animals, and 1 day post exposure (DPE) to 10 DPE for recipient animals. Donors were sacrificed at 3 DPI (2 DPE), and blood was collected from BXA- and placebo-treated ferrets by cardiac puncture. Recipients were sacrificed at 10 DPE.

Experiment 2: Antiviral treatment commenced at 1 DPI, and recipient co-housing was delayed until 24 hr following treatment (2 DPI). Body weight and temperature were monitored daily from all animals. Daily nasal wash samples were collected using 1 mL of PBS from 1 DPI to 4 DPI for donor animals, and 1 DPE to 10 DPE for recipient animals. Donors were sacrificed at 4 DPI (2 DPE), and blood was collected from BXA- and placebo-treated ferrets by cardiac puncture. Recipients were maintained until 16 DPE, at which time blood was collected by cardiac puncture.

Experiment 3: Antiviral treatment commenced at 2 DPI, and recipients were co-housed immediately afterwards. Body weight and temperature were monitored daily from all animals. Daily nasal wash samples were collected using 1 mL of PBS from 1 DPI to 4 DPI for donor animals, and 1 DPE to 10 DPE for recipient animals. Donors were sacrificed at 4 DPI (2 DPE), and blood was collected from BXA- and placebo-treated ferrets by cardiac puncture. Recipients were maintained until 16 DPE, at which time blood was collected by cardiac puncture.

Results and Discussion

In three independent experiments, a single BXA treatment of H1N1pdm09-infected ferrets significantly reduced the infectious virus titers in the URT compared to both placebo and oseltamivir (FIG. 14). The mean viral titres of the baloxavir-group were significantly reduced compared to the placebo-group 24 hours following treatment in all experiment conditions ($p \leq 0.05$). Whereas high infectious titers were maintained at donor endpoint for oseltamivir-group and placebo-group donors, no (i.e. 0/4) baloxavir-treated donors were TCID50-positive at the endpoint in all experiment schedules. The effect of baloxavir is superior to oseltamivir in the treated donors (FIG. 15). All (i.e. 4/4) oseltamivir-treated donors were TCID50-positive at endpoint in all conditions—there was no reduction compared to all (i.e. 4/4) placebo-treated donors.

In the ferret model used, the placebo-group recipients demonstrate that the frequency of contact transmission of A/Perth/265/2009 to naïve ferrets is 100% (FIGS. 14-15). Placebo-group recipients demonstrate robust virus kinetics measured by both $TCID_{50}$ and qRT-PCR, and serum antibody responses of high titre (>1280) at recipient endpoint (FIGS. 7A-7B, 10A-10C, and 13A-13C). We observed that oseltamivir-treatment does not reduce contact transmission to naïve ferrets. 100% of oseltamivir-recipients demonstrated infection parameters that are highly similar to placebo, regardless of timing of antiviral treatment (FIGS. 7A-7B, 10A-10C, and 13A-13C). In contrast, baloxavir treatment within 24 hr of infection resulted in a 75% reduction of transmission. In both Exp. 1 and 2, only 1/4 baloxavir-group recipient displayed a $TCID_{50}$-virus kinetic curve indicating infection similar to placebo (FIGS. 7A-7B and 10A-10C). When baloxavir treatment was administered 48 hr post infection, a 50% reduction in transmission was still observed (FIGS. 13A-13C).

The abundance of viral RNA in the URT of baloxavir-treated ferrets does not correlate with the changes in infectious virus titer measured by cell culture.

While viral RNA was detected in 2/4 baloxavir-group recipients in Exp. 1, the copy numbers are approaching the threshold of positive detection, and the virus kinetics do not resemble a placebo-group virus curve (FIGS. 7A-7B).

Despite the presence of virus shedding in the URT detected by qRT-PCR, these viruses do not appear capable of producing detectable infection in cell culture.

Antibody responses were detected in $TCID_{50}$-negative baloxavir-group recipients in Exp. 2 (FIGS. 10A-10C, 15563) and 3 (FIGS. 13A-13C, 96642, 14779), but were reduced by 16-32 fold compared to titres in placebo-group recipients.

The mean plasma concentration of baloxavir reached the maximum 3 hours postdose (26.1 ng/mL), and then gradually declined toward the last sampling point (168 hours postdose, 9.08 ng/mL). This result indicated that the single subcutaneous administration of a baloxavir suspension at 4 mg/kg (4 locations, 1 mg/kg per location) could maintain the plasma concentration of baloxavir for a week or more in ferret.

In addition, the data clearly show that baloxavir-treatment reduces contact transmission.

Example 3: Flu Transmission Modeling for Baloxavir

Based on the surprising finding that baloxavir marboxil is able to prevent transmission of the influenza virus, a simulation which shows the effect of baloxavir-treatment on influenza outbreaks could be performed. Also considered for this simulation was the impact of baloxavir on the time to cessation of viral shedding (Tshed) observed in a Phase 3 clinical trial (NCT02954354).

The simulation was done by providing the expected percentage of infected patients during flu epidemics and flu pandemics by developing a specific model accounting for
    the flu/social characteristics
    the different treatment effects
    About the Model
Examples 1 and 2 as described above show that baloxavir treatment does not only reduce viral shedding, but surprisingly also reduces transmission. The surprising and unexpected information that baloxavir marboxil can be used for reducing transmission is the prerequisite for the simulation performed below, which simulates the effect of baloxavir marboxil treatment during an (emerging) influenza epidemic or influenza pandemic.

For this simulation the epidemiological SEIR Model has been used. First described early in the 20th Century (Kermack and McKendrick), such model characterizes the number of infections in a population by integrating different types of individuals: susceptibles, exposed, infected and recovered individuals. Such model is actually widely utilized for influenza pandemic planning, policy decisions regarding stockpiling and deployment of antivirals and other interventions and is described, e.g., in Murillo, *J Theor Biol.* 2013. 332:267-290.

Assumptions
1) Viral shedding is correlated to infectiveness with a constant infectiveness during the viral shedding period.
2) Phase 3 results provide correct estimations of the expected time of shedding for baloxavir and oseltamivir treatments
3) All the patients will have:
    the same latency period
    the same natural disease duration
    the same infectious rate over the disease period
    No specific intervention other than treatment
    No age, geography or health status effects on susceptibility Results and Discussion Significant reduction of the percentages of infected patients with baloxavir as compared to placebo or oseltamivir in both seasonal (see FIG. 15) and pandemic (see FIG. 16) scenarios.

The results show that the % of treated patients required to reduce by half the number of infected patients is approximately 15% treated or 30% treated in epidemic or pandemic respectively. The exact threshold for classifying an influenza outbreak as "epidemic" or "pandemic" changes every year. However, in view of the obtained results it is highly likely that treating at least 15% or at least 30% of the infected persons with baloxavir marboxil would prevent an influenza epidemic, or influenza pandemic, respectively.

Example 4: Sequence-Based Identification of Transmission

A phylogenetic analysis (whole genome tree with bootstrap support of tree topology or clustering) and/or measurement of genetic distance between paired populations (L1-Norm) can be conducted for identifying transmission paris. Two factors influence the outcome of the analysis: first, the amount of available sequence data. To maximize this whole genome next-generation sequencing (WGNGS) can be conducted to increase granularity and discriminatory power (compared to Sanger sequencing and/or single gene sequencing). Second, the diversity in the community/meta-population sampled, such that the assessment that viruses from within household pairs are more similar to each other compared to an outgroup can be done with high confidence. More sequences obtained from a community increase diversity in this group and thus facilitate identification of real transmission pairs. Since sequencing for persons not enrolled in the study cannot be conducted, the inventors will do this analysis for a subgroup of patients, focusing on sites which have enrolled an adequate number of index patients (IP) with unique sequences. In addition, the inventors will try to obtain sequences from community databases for the same season (this route is expected to yield little, but will be pursued).

In a previous study investigating the evolution of influenza virus in the HIVE cohort, 47 transmission pairs were analyzed and could be distinguished based on sequence. Thirty four pairs thereof were from one season (H3N2, 2014/2015). Based on these results it is expected that ≥15 index patients (IP), preferably at least 30-40 index patients (IP) will be sufficient to develop a community distribution of pair wise distances, reflecting the community diversity, such that one can infer true household transmission events with sequence data as described in McCrone, John T., et al. "Stochastic processes constrain the within and between host evolution of influenza virus." Elife 7 (2018): e35962. The methods as described in McCrone (Elife 7 (2018): e35962), such as the Method which is described therein for the sequencing may be used. In the context of the present invention the analysis is preferably focused on the analysis of influenza A virus samples.

In order to better understand the method which was used for identifying transmission pairs as well as the background considerations of this method, the content of the document McCrone (Elife 7 (2018): e35962) is briefly discussed below.

In McCrone (Elife 7 (2018): e35962) both epidemiologic linkage and the genetic relatedness of viruses in households was used to define transmission pairs and to exclude confounding from the background diversity in the community.

More specifically, in McCrone (Elife 7 (2018): e35962) it is described that studies of influenza A virus (IAV) populations in animal and human systems suggest that most intrahost single nucleotide variants (iSNV) are rare and that intrahost populations are subject to strong purifying selection. In McCrone (Elife 7 (2018): e35962) next generation sequencing of within-host influenza virus populations was used to define the evolutionary dynamics of IAV within and between human hosts. A benchmarked analysis pipeline was applied to identify iSNV and to characterize the genetic diversity of H3N2 and H1N1 populations collected over five post-pandemic seasons from individuals enrolled in a prospective household study of influenza. In McCrone (Elife 7 (2018): e35962) the authors find that intrahost populations are dynamic and constrained by genetic drift and purifying selection. In the study of McCrone (Elife 7 (2018): e35962) positive selection rarely amplified a beneficial de novo variant to a frequency greater than 2%. Contrary to what has been previously reported for human influenza transmission, but consistent with what has been observed in many other viruses with distinct modes of transmission, a very tight effective transmission bottleneck that limits the transmission of low-frequency variants was identified in McCrone (Elife 7 (2018): e35962).

In McCrone (Elife 7 (2018): e35962) individuals within a household were considered an epidemiologically linked transmission pair if they were both positive for the same subtype of influenza virus within 7 days of each other. Several households had 3 or four symptomatic cases within this one-week window, suggestive of longer chains of transmission.

Intrahost single nucleotide variants (iSNV) were identified in McCrone (Elife 7 (2018): e35962) 2014) using their empirically validated analysis pipeline. Consistent with previous studies of natural infections and those of others, the authors of McCrone (Elife 7 (2018): e35962) found that the within-host diversity of seasonal influenza A virus (IAV) populations is low. Two hundred forty-three out of the 249 samples had fewer than 10 minority iSNV (median 2, IQR 1-3). The number of minority iSNV identified was not affected by the day of infection, viral load, subtype, or vaccination status.

In McCrone (Elife 7 (2018): e35962) single nucleotide variants were distributed evenly across the genome. Minority variants were rarely shared among multiple individuals. Ninety-eight percent of minority iSNV were only found once, 2.3% were found in two individuals, and no minority iSNV were found in three or more individuals. The low level of shared diversity suggests that within-host populations explore distinct regions of sequence space with little evidence for parallel evolution. The ratio of nonsynonymous to synonymous variants was 0.75, and given the excess of nonsynonymous sites across the genome and within the HA gene, these data suggest significant purifying selection within hosts.

It was found in McCrone (Elife 7 (2018): e35962) that the majority of iSNV (68%) found in the second sample were either new or previously present below the 2% limit of detection. Taken together, the data of McCrone (Elife 7 (2018): e35962) suggest that the population present in the upper respiratory tract is highly dynamic while maintaining a stable consensus, and that the positive selection of novel variants within hosts is inefficient and rarely amplifies a newly generated variant to a frequency greater than 2%.

The within-host data of McCrone (Elife 7 (2018): e35962) suggest that newly arising iSNV with positive fitness effects are likely to be present at low frequencies (<2%) during an acute infection. The maintenance of these mutations in host populations is therefore highly dependent on the transmission bottleneck.

In McCrone (Elife 7 (2018): e35962) all individuals in a household with symptom onset within a 7 day window were considered to be epidemiologically linked. The donor in each putative pair was defined as the individual with the earlier onset of symptoms. A transmission event was disregarded if there were multiple possible donors with the same day of symptom onset. Donor and recipients were not allowed to have symptom onset on the same day, unless the individuals were both index cases for the household. Based on these criteria, the cohort of McCrone (Elife 7 (2018): e35962) had 124 putative household transmission events over five seasons. Of these, 52 pairs had samples of sufficient quality for reliable identification of iSNV from both individuals.

Next, sequence data were used in McCrone (Elife 7 (2018): e35962) to determine which of these 52 epidemiologically linked pairs represented true household transmission events as opposed to coincident community-acquired infections. The genetic distance between influenza populations from each household pair was measured by L1-norm and these distances were compared to those of randomly assigned community pairs within each season.

In McCrone (Elife 7 (2018): e35962) only individuals were considered to be a true transmission pair if they had a genetic distance below the 5th percentile of the community distribution of randomly assigned pairs. Forty-seven household transmission events met this criterion. Among these 47 sequence-validated transmission pairs, three had no iSNV in the donor and one additional donor appeared to have a mixed infection. These four transmission events were removed from the bottleneck analysis, as donors without iSNV are uninformative and mixed infections violate model assumptions of site independence. The transmission bottleneck in the remaining 43 high-quality pairs (37 H3N2, 6 H1N1) was estimated.

A transmission bottleneck restricts the amount of genetic diversity that is shared by both members of a pair. It was found in McCrone (*Elife* 7 (2018): e35962) that few minority iSNV were polymorphic in both the donor and recipient populations. Minority iSNV in the donor were either absent or fixed in the recipient. The lack of shared polymorphic sites suggests a stringent effective bottleneck in which only one allele is passed from donor to recipient.

The authors of McCrone (*Elife* 7 (2018): e35962) conclude that acute influenza infections are characterized by low diversity, limited positive selection, and tight transmission bottlenecks. Because viruses collected over five influenza seasons from individuals enrolled in a prospective household cohort were used, these dynamics are likely to be broadly representative of many seasonal influenza infections in temperate regions. The data of McCrone (*Elife* 7 (2018): e35962) suggest that even if selection acts below the level of detection, such rare variants are unlikely to transmit. Given the size of the estimated bottleneck, the probability of transmission is approximately 1.7% for a variant at 1% frequency and 3.3% for a variant at 2% frequency.

Example 5: Pharmacokinetic Analysis in Ferret

Materials, Methods and Results for Animals

Outbred female and ferrets 28 months old and weighing between 650-802 g were obtained from Japan SLC, Inc. Identification was conducted by labeling sequential number in front of each cage. Animals were monitored at least once daily for their clinical observations, and had ad libitum access to pellet feed (LabDiet High Density Ferret Diet, Lab Supply, USA) and water. Ferrets at endpoint were euthanized by exsanguination under anesthesia by inhalation with isoflurane (Pfizer). Ferret studies were performed in Shionogi Pharmaceutical Research Center, Shionogi & Co., Ltd. (Osaka, Japan), according to the animal study protocol which was approved by the Institutional Animal Care and Use Committee in Shionogi.

Drug Administration and Blood Samplings

The active form baloxavir acid (S-033447, hereafter BXA) was provided by Test Substance Control Personnel, Shionogi & Co., Ltd., Japan. The vehicle for BXA delivery was methyl cellulose (Fuji-Film Wako, Japan) in 0.5 w/v % aqueous solution prepared with sterile water (hereafter MC solution). BXA in suspension with MC solution (1 mg/mL) was prepared using an agate mortar and pestle, and was delivered to reversibly anaesthetised animals in a single treatment consisting of 4 subcutaneous injections at 4 locations on the dorsal region (total dose 4 mg/kg per animal). After a dosing, the needlestick lead to bleeding from the hindlimb vein for blood sampling, and then the blood (approximately 60-100 μL) samples were collected from bleeding part using heparinized capillary tubes (Drummond Scientific Company, USA) at the scheduled time, and the plasma was obtained by centrifuging. The plasma samples were stored in a freezer at approximately −80° C. until use for the analysis by liquid chromatography with tandem mass spectrometry (LC-MS/MS) system.

Determination of BXA in Plasma

The plasma concentration of BXA was determined by LC-MS/MS, consisting of LC-20A system (Shimadzu Corporation, Japan) and API 5000 (AB SCIEX, USA). The plasma samples were prepared by protein precipitation. Chromatographic separation was performed on L-column 2 ODS metal free (3 μm, 2.0 mm i. d.×50 mm, Chemicals Evaluation and Research Institute, Japan) at 40° C. The binary mobile phases, 0.1% formic acid in water and 0.1% formic acid in acetonitrile, were delivered at the total flow rate of 0.6 mL/min in gradient mode. The mass spectrometer was operated in electrospray ionization (ESI) positive polarity mode using multiple reaction monitoring (MRM). Precursor/product transitions (m/z) of 484/247 and 490/247 were monitored for BXA and internal standard, BXA-racemate-$d_4$$^{18}$O, respectively. Calculations were based on peak area ratios of BXA to internal standard. The analytical method was validated across the calibration range 0.5 to 500 ng/mL with respect to selectivity, recovery, accuracy, precision, and stability under a variety of conditions.

Pharmacokinetic Analysis

The plasma concentrations of BXA for each individual ferret were calculated by Analyst software (AB SCIEX, USA). The mean value and standard deviation were also calculated using individual data by Microsoft Excel (Microsoft Co., USA).

Result and Discussion

The mean plasma concentration reached the maximum 3 hours postdose (26.1 ng/mL), and then gradually declined toward the last sampling point (168 hours postdose, 9.08 ng/mL). This result indicated that the single subcutaneous administration of BXA suspension at 4 mg/kg (4 locations, 1 mg/kg per location) could maintain the plasma concentration of BXA for a week or more in ferret.

The present invention refers to the following nucleotide and amino acid sequences:

```
SEQ ID NO: 1:
Forward primer for real-time PCR
5'GACCRATCCTGTCACCTCTGA 3'

SEQ ID NO: 2:
Reverse primer for real-time PCR
5' AGGGCATTYTGGACAAAKCGTCTA3'

SEQ ID NO: 3:
Probe for real-time PCR ("FAM" means fluorescein amidite,
i.e. the fluorescent dye to lable oligonucle-
otides; "BHQ1" means
Black Hole Quencher 1, i.e. the quencher; BHQ1 and FAM together
are not fluorescent, only after probe is cleaved FAM will be
fluorescent)
5' FAM-TCGAGTCCTCGCTCACTGGGCACG-BHQ1 3'
```

-continued

SEQ ID NO: 4:
Influenza A virus (A/WSN/1933(H1N1)): GenBank: X17336.1,
comprising the I38T mutation. The I38T mutation is
underlined and shown in bold face.
MEDFVRQCFNPMIVELAEKAMKEYGEDLKIETNKFAATCTHLEVCFMYSDFHFIDEQGESI

VVELGDPNALLKHRFEIIEGRDRTIAWTVINSICNTTGAEKPKFLPDLYDYKKNRFIEIGVTR

REVHIYYLEKANKIKSEKTHIHIFSFTGEEMATKADYTLDEESRARIKTRLFTIRQEMASRGL

WDSFRQSERGEETIEERFEITGTMRKLADQSLPPNFSSLENFRAYVDGFEPNGYIEGKLSQM

SKEVNARIEPFLKSTPRPLRLPDGPPCSQRSKFLLMDALKLSIEDPSHEGEGIPLYDAIKCMR

TFFGWKEPNVVKPHEKGINPNYLLSWKQVLAELQDIENEEKIPRTKNMKKTSQLKWALGE

NMAPEKVDFDDCKDVGDLKQYDSDEPELRSLASWIQNEFNKACELTDSSWIELDEIGEDA

APIEHIASMRRNYFTAEVSHCRATEYIMKGVYINTALLNASCAAMDDFQLIPMISKCRTKE

GRRKTNLYGFIIKGRSHLRNDTDVVNFVSMEFSLTDPRLEPHKWEKYCVLEVGDMLLRSAI

GHVSRPMFLYVRTNGTSKIKMKWGMEMRRCLLQSLQQIESMIEAESSVKEKDMTKEFFEN

KSETWPVGESPKGVEEGSIGKVCRTLLAKSVFNSLYASPQLEGFSAESRKLLLIVQALRDNL

EPGTFDLGGLYEAIEECLINDPWVLLNASWFNSFLTHALR

SEQ ID NO: 5:
Sequence fraction of the influenza A virus (A/WSN/1933(H1N1)):
GenBank: X17336.1, comprising the I38T mutation. The I38T
mutation is underlined and shown in bold face.
FAATCTH

---

What is claimed:

1. A method of reducing the rate of transmission of an influenza virus infection comprising administering an effective amount of a compound to an index patient infected with the influenza virus, wherein the compound has the formula (II):

(II)

[chemical structure]

or a pharmaceutically acceptable salt thereof; and
wherein the method reduces the rate of transmission of the influenza virus from an index patient to at least one contact person as compared to the rate of transmission of the influenza virus from a control patient to at least one contact person.

2. The method of claim 1, wherein the control patient has the influenza virus infection, and wherein the control patient has not been administered with an anti-influenza drug, or has been administered with an anti-influenza drug except for the compound of formula (II) or its pharmaceutically acceptable salt thereof.

3. The method of claim 1, wherein the method reduces transmissibility of the influenza virus of the index patient as compared to the transmissibility of the influenza virus of a control patient.

4. The method of claim 1, wherein the rate of transmission of the influenza virus from the index patient is reduced within one hour to 32 hours from the administration of the compound.

5. The method of claim 1, wherein the rate of transmission of the influenza virus from the index patient is reduced to 70% or less as compared to the rate of transmission of the influenza virus from a control patient.

6. The method of claim 2, wherein the at least one contact person had personal contact to the index patient within a period of time starting with the administration of the compound and ending 10 days after the administration of the compound, and wherein the at least one contact person had personal contact to the control patient within a period of time starting with the administration of the anti-influenza drug to the control patient and ending 5 to 10 days after the administration of the anti-influenza drug to the control patient; or starting and ending at the corresponding time points in view of the disease process of influenza if no anti-influenza drug is administered to the control patient.

7. The method of claim 1, wherein the transmission is airborne transmission or direct contact transmission.

8. The method of claim 1, wherein the transmission from the index patient or from the control patient has occurred when an influenza virus can be detected in the respective at least one contact person.

9. The method of claim 8, wherein transmission from the index patient has occurred if the influenza virus can be detected in the at least one contact person of the index patient within 15 days from the administration of the compound to the index patient, and wherein transmission from the control patient has occurred if the influenza virus can be detected in the at least one contact person of the control patient within 15 days from the administration of the other anti-influenza drug to the control patient; or within the corresponding period of time in view of the disease process of influenza if no anti-influenza drug was administered to the control patient.

10. The method of claim 8, wherein the influenza virus is detected via PCR or by using an influenza test kit.

11. The method of claim 1, wherein the transmission from the treated index patient has occurred when at least one contact person of the treated index patient has an influenza virus infection with an influenza virus strain which is identical with the influenza virus strain of the treated index patient, and wherein the transmission from the control patient has occurred when at least one contact person of the control patient has an influenza virus infection with an influenza virus strain which is identical with the influenza virus strain of the control patient.

12. The method of claim 1, wherein the compound is administered one time as single treatment.

13. The method of claim 1, wherein the effective amount is 40 mg for patients <80 kg, and 80 mg for patients ≥80 kg.

14. The method of claim 1, wherein the index patient has a reduced risk to trigger an influenza epidemic or an influenza pandemic as compared to a control patient.

15. The method of claim 1, wherein the influenza virus is an epidemic influenza virus strain or a pandemic influenza virus strain.

16. The method of claim 1, wherein the influenza virus is antigenically different as compared to the parent influenza virus strain as a result of antigenic drift and/or antigenic shift.

17. The method of claim 1, wherein the influenza strain is a recycling virus which had caused an epidemic or pandemic in the past.

18. The method of claim 1, wherein the influenza virus strain does not carry an I38X mutation.

19. A method for preventing an influenza epidemic or an influenza pandemic comprising administering an effective amount of a compound to at least 10% of all influenza infected population, wherein the compound has the formula (II):

(II)

[chemical structure]

or its pharmaceutically acceptable salt.

20. The method of claim 19, wherein the method comprises administering the compound to at least 25% of all influenza infected population, and wherein the method prevents an influenza pandemic.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Forward primer for real-time PCR

<400> SEQUENCE: 1
gaccratcct gtcacctctg a                                              21

<210> SEQ ID NO 2
<211> LENGTH: 24
<212> TYPE: DNA
<213> ORGANISM: Artificial Sequence
<220> FEATURE:
<223> OTHER INFORMATION: Reverse primer for real-time PCR

<400> SEQUENCE: 2
agggcattyt ggacaaakcg tcta                                           24

<210> SEQ ID NO 3
<211> LENGTH: 24
<212> TYPE: DNA
<213> ORGANISM: Artificial Sequence
<220> FEATURE:
<223> OTHER INFORMATION: Probe for real-time PCR

<400> SEQUENCE: 3
tcgagtcctc gctcactggg cacg                                           24

<210> SEQ ID NO 4
<211> LENGTH: 716
<212> TYPE: PRT

<213> ORGANISM: Influenza A virus (A/WSN/1933(H1N1))

<400> SEQUENCE: 4

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Thr Cys Thr His Leu Glu Val Cys Phe Met Tyr
        35                  40                  45

Ser Asp Phe His Phe Ile Asp Glu Gln Gly Glu Ser Ile Val Val Glu
50                  55                  60

Leu Gly Asp Pro Asn Ala Leu Leu Lys His Arg Phe Glu Ile Ile Glu
65                  70                  75                  80

Gly Arg Asp Arg Thr Ile Ala Trp Thr Val Ile Asn Ser Ile Cys Asn
                85                  90                  95

Thr Thr Gly Ala Glu Lys Pro Lys Phe Leu Pro Asp Leu Tyr Asp Tyr
            100                 105                 110

Lys Lys Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Ser Thr Pro Arg Pro Leu Arg Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
            405                 410                 415

Leu Thr Asp Ser Ser Trp Ile Glu Leu Asp Glu Ile Gly Glu Asp Ala
            420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
            485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
            530                 535                 540

Val Gly Asp Met Leu Leu Arg Ser Ala Ile Gly His Val Ser Arg Pro
545                 550                 555                 560

Met Phe Leu Tyr Val Arg Thr Asn Gly Thr Ser Lys Ile Lys Met Lys
            565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Val Gly Glu Ser
            610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
            645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
            675                 680                 685

Ala Ile Glu Glu Cys Leu Ile Asn Asp Pro Trp Val Leu Leu Asn Ala
690                 695                 700

Ser Trp Phe Asn Ser Phe Leu Thr His Ala Leu Arg
705                 710                 715

<210> SEQ ID NO 5
<211> LENGTH: 7
<212> TYPE: PRT
<213> ORGANISM: Artificial Sequence
<220> FEATURE:
<223> OTHER INFORMATION: Sequence fraction of Influenza A virus
      (A/WSN/1933(H1N1))

<400> SEQUENCE: 5

Phe Ala Ala Thr Cys Thr His
1               5